(12) United States Patent
Stevenson et al.

(10) Patent No.: US 6,999,818 B2
(45) Date of Patent: Feb. 14, 2006

(54) INDUCTOR CAPACITOR EMI FILTER FOR HUMAN IMPLANT APPLICATIONS

(75) Inventors: Robert A. Stevenson, Canyon Country, CA (US); Christine A. Frysz, Marriottsville, MD (US); Haytham Hussein, Woodstock, MD (US); Richard L. Brendel, Carson City, NV (US)

(73) Assignee: Greatbatch-Sierra, Inc., Carson City, NV (US)

( * ) Notice: Subject to any disclaimer, the term of this patent is extended or adjusted under 35 U.S.C. 154(b) by 85 days.

(21) Appl. No.: 10/825,900

(22) Filed: Apr. 15, 2004

(65) Prior Publication Data

US 2004/0257747 A1 Dec. 23, 2004

Related U.S. Application Data

(60) Provisional application No. 60/473,228, filed on May 23, 2003, provisional application No. 60/508,426, filed on Oct. 2, 2003.

(51) Int. Cl.
*A61N 1/375* (2006.01)
*A61N 1/16* (2006.01)

(52) U.S. Cl. .......................................... 607/37; 607/36
(58) Field of Classification Search ................ 607/2–5, 607/9, 36–58; 361/302, 306, 306.1
See application file for complete search history.

(56) References Cited

U.S. PATENT DOCUMENTS

| | | | |
|---|---|---|---|
| 2,756,375 A | 7/1956 | Peck | 361/302 |
| 3,235,939 A | 2/1966 | Rodriguez et al. | 29/25.42 |
| 3,920,888 A | 11/1975 | Barr | 174/152 GM |
| 4,083,022 A | 4/1978 | Nijman | 333/183 |
| 4,144,509 A | 3/1979 | Boutros | 333/181 |
| 4,148,003 A | 4/1979 | Colburn et al. | 333/181 |
| 4,152,540 A | 5/1979 | Duncan et al. | 174/152 GM |
| 4,220,813 A | 9/1980 | Kyle | 174/152 GM |
| 4,242,551 A | 12/1980 | Sorenson | |
| 4,424,551 A | 12/1980 | Stevenson et al. | 361/302 |
| 4,247,881 A | 1/1981 | Coleman | 361/302 |
| 4,314,213 A | 2/1982 | Wakino | 333/182 |
| 4,352,951 A | 10/1982 | Kyle | 174/152 GM |
| 4,362,792 A | 12/1982 | Bowsky et al. | 429/181 |
| 4,421,947 A | 12/1983 | Kyle | 174/152 GM |
| 4,456,786 A | 6/1984 | Kyle | 174/152 GM |
| 4,737,601 A | 4/1988 | Gartzke | 174/152 GM |
| 4,741,710 A | 5/1988 | Hogan | 439/620 |
| 5,032,692 A | 7/1991 | De Volder | 174/52.3 |
| 5,070,605 A | 12/1991 | Daglow et al. | 29/842 |
| 5,333,095 A | 7/1994 | Stevenson et al. | 361/302 |
| 5,751,539 A | 5/1998 | Stevenson et al. | 361/302 |
| 5,825,608 A | 10/1998 | Duva et al. | 361/302 |
| 5,905,627 A | 5/1999 | Brendel et al. | 361/302 |
| 5,959,829 A | 9/1999 | Stevenson et al. | 361/302 |

(Continued)

*Primary Examiner*—Carl Layno
(74) *Attorney, Agent, or Firm*—Kelly Lowry & Kelley, LLP

(57) ABSTRACT

A feedthrough terminal assembly for an active implantable medical device includes a conductive ferrule conductively coupled to a housing of the medical device, a feedthrough capacitor conductively coupled to the ferrule, an inductor closely associated with the capacitor in non-conductive relation, and a conductive terminal pin extending through the capacitor and the inductor. The terminal pin extends through the inductor in non-conductive relation and is conductively coupled to active electrode plates of the capacitor. In one preferred form, the terminal pin is wound about the inductor. Additionally, the inductor may be maintained in close association with the capacitor without forming a direct physical attachment therebetween.

252 Claims, 34 Drawing Sheets

U.S. PATENT DOCUMENTS

| | | | |
|---|---|---|---|
| 5,973,906 A | 10/1999 | Stevenson et al. | 361/302 |
| 6,008,980 A | 12/1999 | Stevenson et al. | 361/302 |
| 6,275,369 B1 | 8/2001 | Stevenson et al. | 361/302 |
| 6,349,025 B1 | 2/2002 | Fraley et al. | 361/302 |
| 6,424,234 B1 | 7/2002 | Stevenson | 333/182 |
| 6,529,103 B1 | 3/2003 | Brendel et al. | 333/182 |
| 6,566,978 B1 | 5/2003 | Stevenson et al. | 333/182 |
| 2003/0036776 A1 * | 2/2003 | Foster et al. | 607/9 |

* cited by examiner

FILTER L/C COMPONENTS

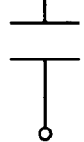

1. Capacitive Reactance, Xc (ohms)

$$Xc = \frac{-j}{2 \times PI \times f \times C}, \text{ where:}$$

C = Capacitance in Microfarads
f = Frequency in Megahertz

Example, 1 Microfarad "Ideal" Capacitor
    DC       infinite ohms (open ckt.)
    1 KHz    159.2 ohms
    1 MHz    0.159 ohms
    100 MHz  0.00159 ohms (short)

FIG. 7
PRIOR ART

FILTER L/C COMPONENTS

1. Inductive Reactance, $X_L$ (ohms)

$$X_L = atj \times 2 \times PI \times f \times L, \text{ where:}$$

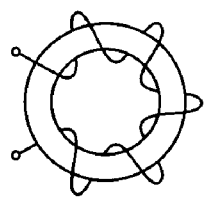

L = Inductance in Microhenries
f = Frequency in Megahertz

Example, 100 Microhenry "Ideal" Toroidal Inductor
    DC       0.0 ohms (short circuit)
    1 KHz    0.628 ohms
    1 MHz    628.0 ohms
    100 MHz  62.83 ohms

FIG. 8
PRIOR ART

Common EMI Filter Circuits
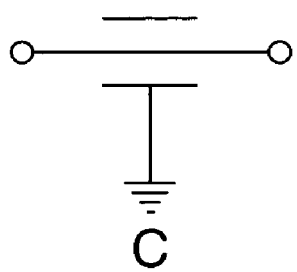
C
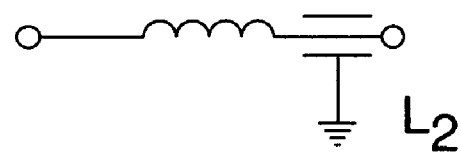
L₂
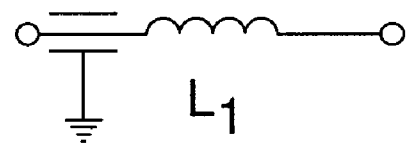
L₁
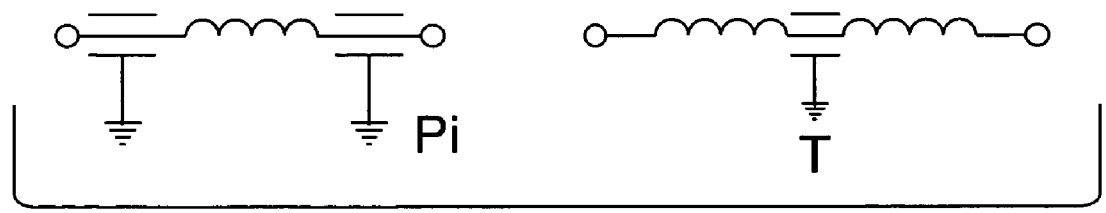
Pi    T
FIG. 9
PRIOR ART

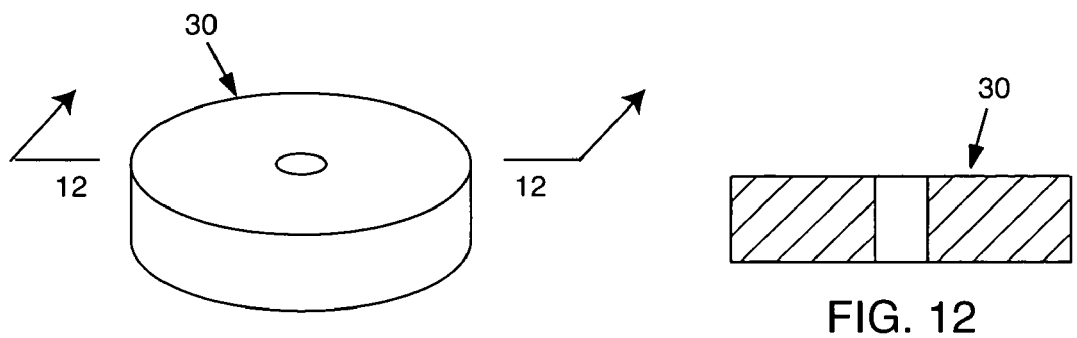
FIG. 11
PRIOR ART
FIG. 12
PRIOR ART
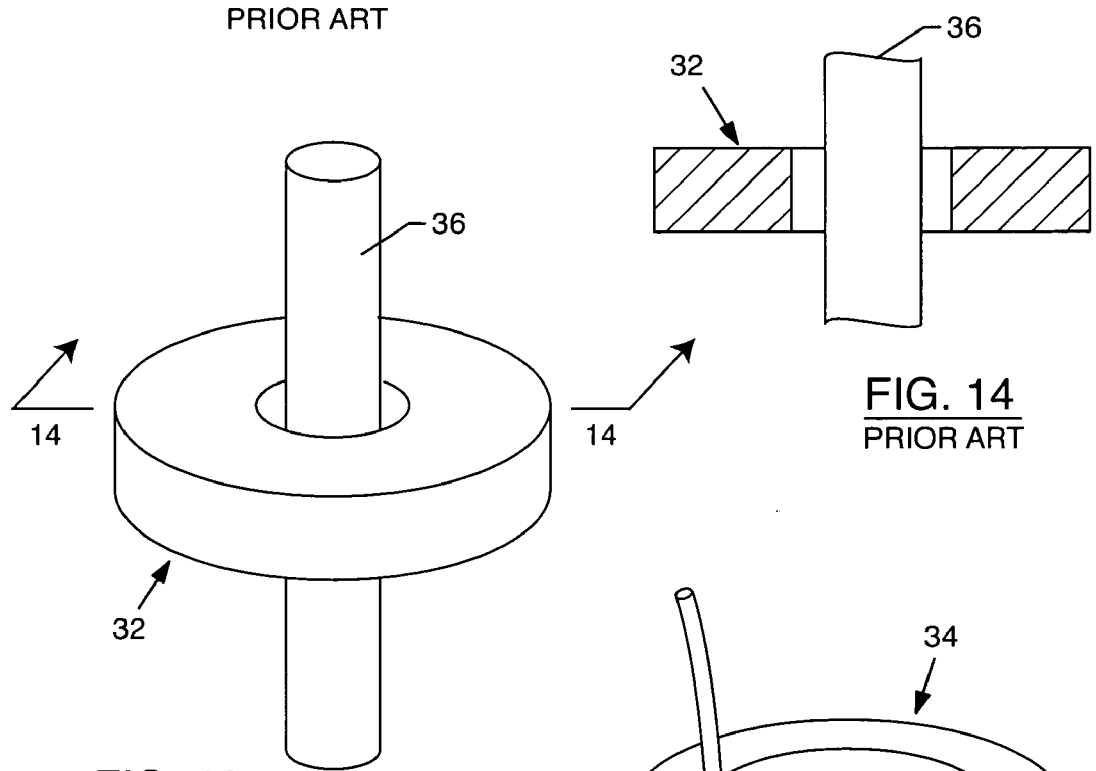
FIG. 13
PRIOR ART
FIG. 14
PRIOR ART
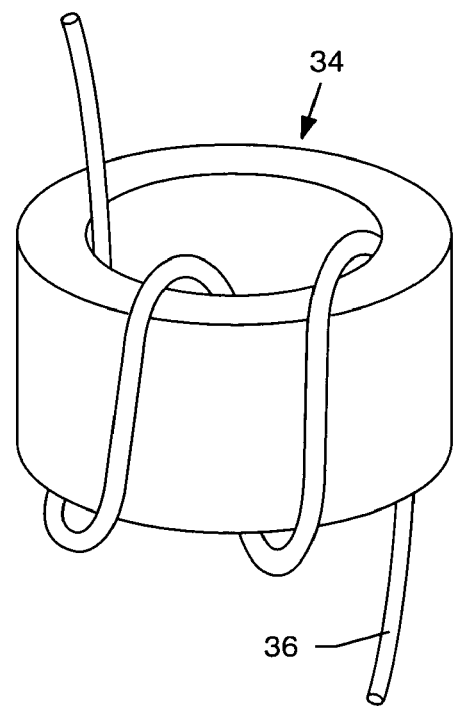
FIG. 15
PRIOR ART

THERMOPLASTIC POLYIMIDE SUPPORTED TAPE ADHESIVE

| MECHANICAL PROPERTIES | TEST METHOD |
|---|---|
| 90° Peel Strength - 250 mil (6.3 mm) width<br>Alloy 42 substrate @ 25°C: 5.0 lb$_r$ (2.3 kg$_r$) peak<br>@ 230°C: 1.4 lb$_r$ (0.64 kg$_r$) peak<br><br>PI Coated Si Substrate @ 25°C: 5.5 lb$_r$ (2.5 kg$_r$) peak<br>@ 230°C: 1.2 lb$_r$ (0.55 kg$_r$) peak | MT-8 |
| Flatwise Tensile Strength - 250 mil² (6.3 mm²)<br>Alloy 42 substrate @ 25°C: 3300 psi (93 kg)<br>@ 230°C: 450 psi (13 kg) | MT-1 |

(1) TH exposure - 16 hours, 85°C/85% RH

FIG. 16

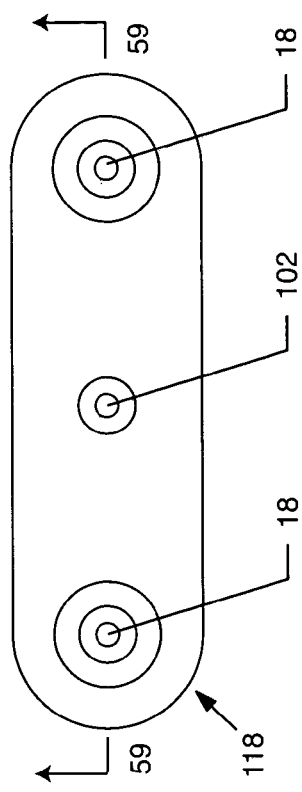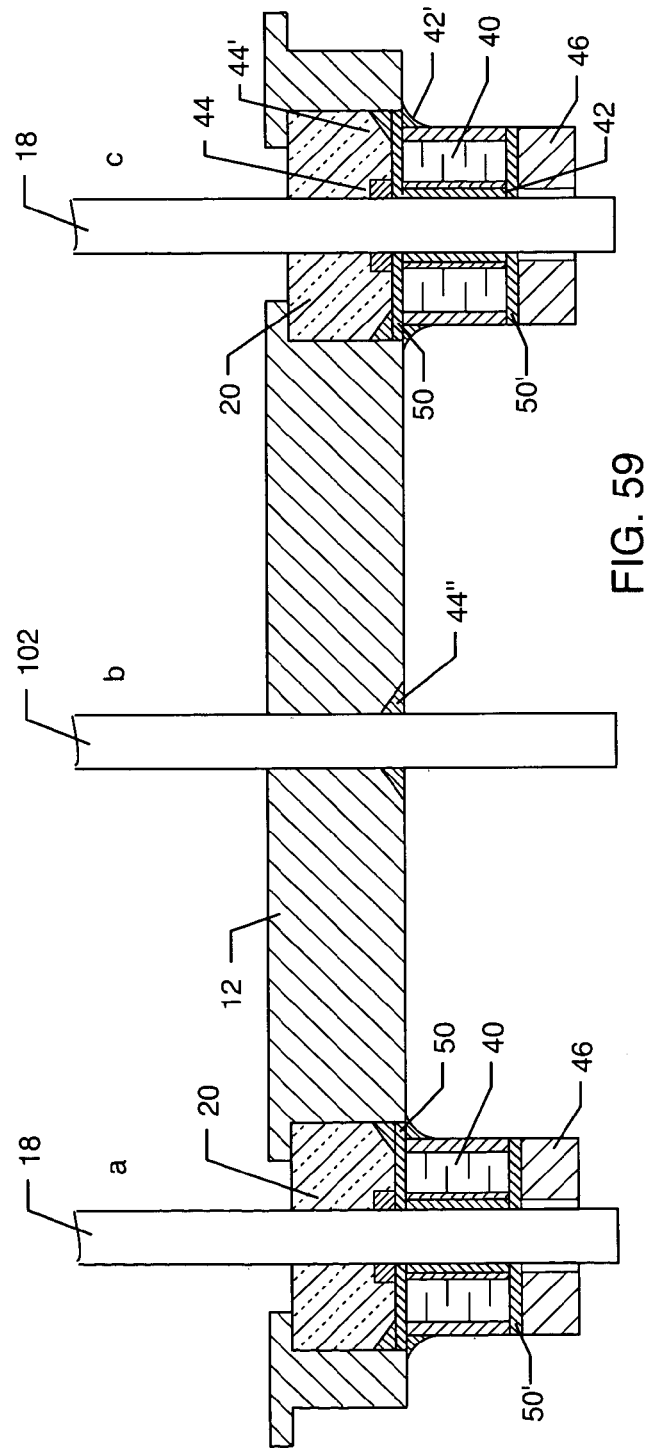
FIG. 58
FIG. 59

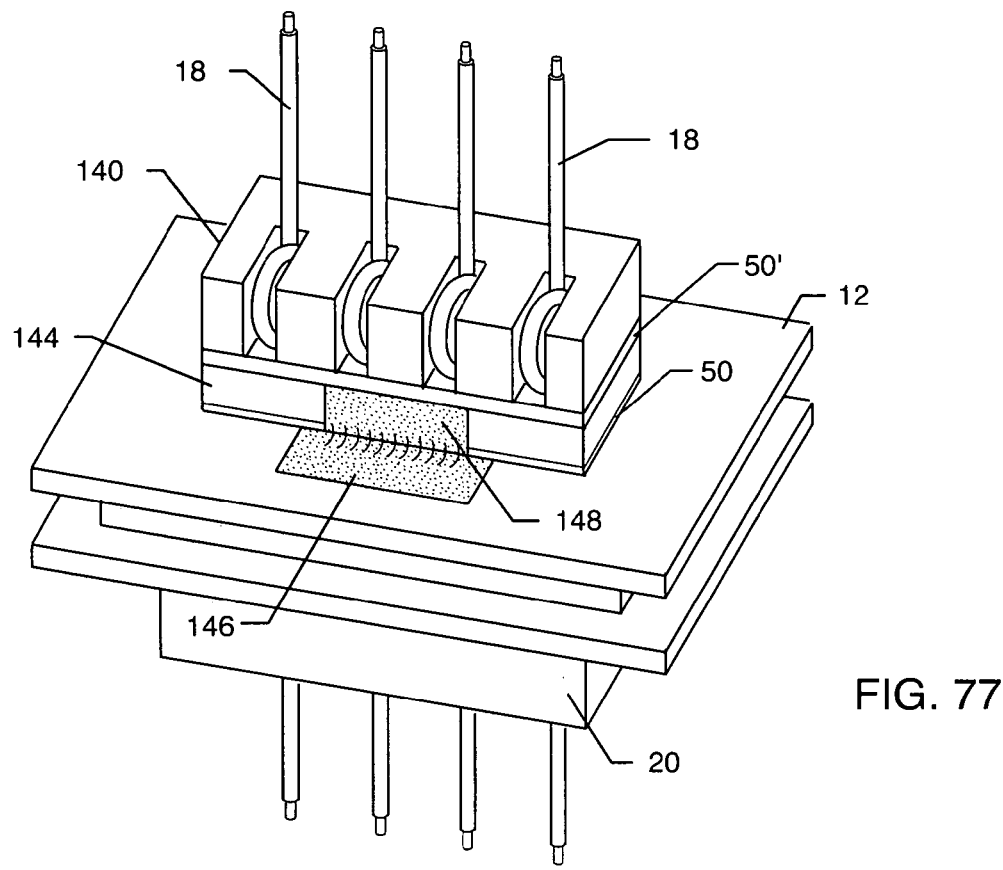
FIG. 77
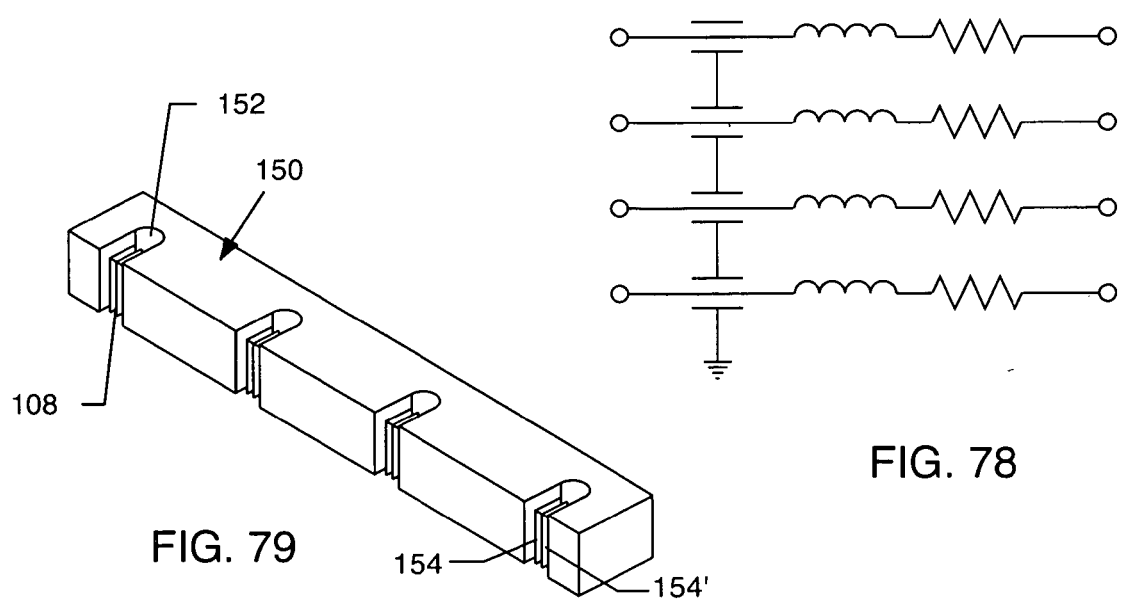
FIG. 78
FIG. 79

INDUCTOR CAPACITOR EMI FILTER FOR HUMAN IMPLANT APPLICATIONS

RELATED APPLICATION

This application claims priority to U.S. Provisional Patent Application Ser. No. 60/473,228, filed May 23, 2003 and U.S. Provisional Patent Application Ser. No. 60/508,426, filed Oct. 2, 2003.

BACKGROUND OF THE INVENTION

This invention relates generally to feedthrough capacitor terminal pin subassemblies and related methods of construction, particularly of the type used in implantable medical devices such as cardiac pacemakers, implantable defibrillators, cochlear implants, and the like. Such terminal pin subassemblies form EMI filters designed to decouple and shield undesirable electromagnetic interference (EMI) signals from an associated device. Specifically, the present invention relates to an improved EMI filter that includes an inductive element, making the EMI filter a two element (2-pole) or three element (3-pole) device, or even higher order device. Feedthrough terminal assemblies are generally well known for connecting electrical signals through the housing or case of an electronic instrument. For example, in implantable medical devices, such as cardiac pacemakers, defibrillators, or the like, the terminal pin assembly comprises one or more conductive terminal pins supported by an insulator structure for feedthrough passage from the exterior to the interior of the medical device. Many different insulator structures and related mounting methods are known for use in medical devices wherein the insulator structure provides a hermetic seal to prevent entry of body fluids into the housing of the medical device. In a cardiac pacemaker, for example, the feedthrough terminal pins are typically connected to one or more lead wires within the case to conduct pacing pulses to cardiac tissue and/or detect or sense cardiac rhythms.

However, the lead wires can also effectively act as an antenna and thus tend to collect stray electromagnetic interference (EMI) signals for transmission into the interior of the medical device. Studies conducted by the United States Food and Drug Administration, Mt. Sinai Medical Center in Miami and other researchers have demonstrated that stray EMI, such as that caused by cellular phones, can seriously disrupt the proper operation of the pacemaker. It has been well documented that pacemaker inhibition, asynchronous pacing and missed beats can occur. All of these situations can be dangerous or life threatening for a pacemaker-dependant patient.

In prior devices, such as those shown in U.S. Pat. Nos. 5,333,095 and 4,424,551 (the, contents of which are incorporated herein), the hermetic terminal pin subassembly has been combined in various ways with a ceramic feedthrough capacitor filter to decouple electromagnetic interference (EMI) signals into the housing of the medical device. FIG. 1 is a cross-sectional view of the feedthrough terminal assembly disclosed is U.S. Pat. No. 5,333,095. Within the drawings herein, functionally equivalent elements of structure shown in the drawings will be referred to by the same reference number irrespective of the embodiment shown. The assembly 10 includes a conductive ferrule 12 which is conductively connected to a housing or casing 14 of a human implantable device, such as a cardiac pacemaker, an implantable defibrillator, or a cochlear implant or the like. The assembly 10 includes a feedthrough capacitor 16 having a grounding portion 24 which is conductively coupled to the ferrule 12. At least one terminal pin or lead wire 18 extends through the ferrule 12, in non-conductive relation, and through the capacitor 16 in conductive relation. Typically, an alumina insulator 20 is disposed between the terminal pin 18 and the ferrule 12 or other conductive substrate through which the terminal pin 18 passes through in non-conductive relation. The capacitor 16 may be bonded to the insulator 20 or separated from the insulator 20 thereby forming an air gap depending on the assembly method used. Typically, the outside diameter metallization 24 of the capacitor 16 is installed in conductive relation with the conductive substrate or ferrule 12 so that the ground electrodes of feedthrough capacitor 16 are properly grounded. An alternative arrangement is shown in U.S. Pat. No. 5,905,627, the contents of which are incorporated herein.

FIG. 2 illustrates the uni-polar monolithic ceramic feedthrough capacitor 16 of FIG. 1, which is typical in the prior art described by the U.S. Pat. Nos. 5,333,095 and 4,424,551 patents and many others. Both inside diameter and outside diameters 22 and 24 are metallized using a conductive termination which puts the respective electrode plate sets in parallel. The feedthrough capacitor is designed to have the lead wire 18 pass through the center of it. The lead wire or terminal pin 18 is conductively coupled to the inner diameter metallization 22 so as to be conductively coupled to a first set of active electrodes 26. A second set of ground electrodes 28 are conductively coupled to the outer diameter metallization 24 for grounding to the conductive substrate or ferrule 12.

FIG. 3 is the schematic diagram of the feedthrough capacitor of FIG. 2. As shown, feedthrough capacitors are three terminal devices which offer broadband performance and are best modeled by transmission line equations. Feedthrough capacitors are novel in that they act like broadband transmission lines and have very low inductance properties. This means that they can provide effective EMI filtering immunity over very broad frequency ranges. They do this by de-coupling high frequency noise and shunting it to the overall titanium or stainless shield housing 14 of the implantable medical device. This is in contrast to rectangular monolithic chip capacitors and other two terminal capacitors which have a substantial amount of series inductance. Two terminal capacitors tend to self resonate at very low frequency and thus make very poor EMI filters, particularly for high frequencies such as cell phones, microwave ovens, radars and other emitters.

FIGS. 4 and 5 illustrate another type of capacitor 16, which is a multi-hole micro-planar array quad-polar feedthrough capacitor. This has essentially the same properties as the previously described uni-polar feedthrough capacitor illustrated in FIGS. 2 and 3, and can accommodate multiple terminal pins therethrough. FIG. 6 is the schematic drawing of the quad-polar capacitor of FIGS. 4 and 5.

FIG. 7 describes the capacitor reactance equation and illustrates how the capacitor reactance varies in ohms vs. frequency for an ideal capacitor. At DC, capacitors look like open circuits (in other words, like they are not there). At high frequencies, well-designed capacitors tend to look like a very low reactance in ohms (or short circuit). In this way, capacitors are frequency selective components and can be used to short out or bypass undesirable high frequencies thereby acting as low pass filter devices.

In the past few years, a number of new devices have been introduced to the active implantable medical device market. These include implantable cardioverter defibrillators, which not only offer high voltage shock therapy to the heart, but also provide monitoring, anti-tachycardia pacing and conventional atrial and ventricular pacing. Very recently introduced are congestive heart failure devices, also known on the market as biventricular pacemakers. All of these new devices have a need for an increased number of lead wires to be implanted within the heart or outside the vasculature of the heart. This has greatly complicated the loop coupling and antennae coupling areas for EMI induction. This also means that more lead wires must ingress and egress the implantable medical device. Accordingly, it is now common for 8-pin, 12-pin or even 16-pin devices to be present in the marketplace, all of which have unique filtering needs.

There have also been new developments in sensor technology. Lead based sensors are under investigation as well as new telemetry methods. The Federal Communications Commission has recently opened up higher frequency telemetry channels (402 MHz) to meet the demands for more bandwidth on the part of physicians (better access to stored data, recovery of historical cardiac waveforms, etc.). Most modern pacemakers and implantable defibrillators store a substantial amount of data and can download cardiac waveforms for later investigation by the physician.

There has also been an increase in the number of emitters generally in the marketplace. An example of this is the new Blue Tooth System, which is rapidly gaining acceptance. Blue Tooth is a method of interconnecting computers and the peripheral devices in a wireless manner. This also increases the number of digital signals to which an implantable device patient is exposed. Accordingly, there is an ever-increasing need for better EMI immunity of implantable medical devices over wider frequency ranges.

As mentioned, there has been a substantial amount of research into the interaction of implantable medical devices with cellular phones, theft detectors and other emitters. This research is ongoing today, particularly in the area of cardiac pacemakers and ICDs. Recently, high-gain cellular telephone amplifiers combined with high-gain antennas have become available in consumer markets. This creates a concern because the single element EMI filters presently designed into pacemakers and ICDs are based on research when cellular telephone maximum output power was limited to 0.3 or 0.6 watts. When a cellular phone is combined with these new amplifiers and high-gain antennas, the output power increases by a factor of 20 to 30 dB. This is equivalent to a 23.8-watt cell phone.

Prior art EMI filters for medical implant applications have generally consisted of single pole devices consisting of a single feedthrough capacitor element on each lead wire. It is possible to increase the amount of attenuation of a single element feedthrough capacitor by raising the capacitance value. This also desirably lowers the frequency at which the capacitor starts to become effective. This is known as the feedthrough capacitor's 3 dB cutoff point. Unfortunately, raising the capacitance also has a number of undesirable side effects. First of all, too much capacitance can start loading down the output of an implantable medical device thereby degrading its operation. Too much capacitance can also be a problem in that excess energy dissipation can occur as the capacitor must be charged and discharged during cardiac pacing or digital signal processing in a hearing device.

In an EMI filter design of a low pass filter, a single element filter consisting of a feedthrough capacitor increases in attenuation at 20 dB per decade. This is a consequence of the mathematics of computing the capacitive reactance as described in FIG. 7 and its behavior as a low pass filter circuit. The capacitive reactance $X_c$ in ohms varies inversely as the capacitance value and also inversely with frequency.

An inductor performs the opposite function in that the inductive reactance $X_L$ in ohms, as shown in FIG. 8, varies directly with the frequency and the inductance in microhenries. This formula is applicable not only to multi-turn toroids, but single turn ferrite beads as well. The inductive reactance $X_L$ is the opposite of capacitance reactance $X_c$ in that inductive reactance increases with increasing frequency. As illustrated, inductive reactance is zero ohms at DC and goes up to a very high value at high frequency.

Therefore, when placed in series with a line, inductance can raise the impedance of the line thereby also acting as a low pass filter. Common prior art EMI filter circuits are shown in FIG. 9 consisting of single element feedthrough capacitors "C", "double element $L_1$" and "reverse $L_2$" filters, which combine an inductor and a capacitor, and other elements or other configurations including "PI" and "T" configurations. The commonly used prior art filter circuit for medical implant applications has been the "C" circuit or feedthrough capacitor. All of the cited patent references are based on a single element feedthrough capacitors bonded directly to or in close proximity to the hermetic terminal of an implantable medical device. However, using inductance in combination with a feedthrough capacitor increases the filter's effectiveness.

Of particular interest are the graphs shown in FIG. 10. The horizontal or X axis is frequency in MHz and the vertical or Y axis is the filtering efficiency measured as insertion loss in dB. For a one component feedthrough capacitor filter "C", the insertion loss increases with frequency at a slope of 20 dB per decade. However, when one adds an inductive component this makes the low pass filter into a two-element "L" filter. A two element filter like an "L" filter goes up at a slope of 40 dB per decade. This means that its filtering effectiveness at high frequency is much greater than a single element filter. If one were to add inductors on both sides of the capacitor, it would become a three component filter, which would increase at 60 dB per decade and so on.

A single element feedthrough capacitor is limited to an attenuation increase of 20 dB per decade. This is a linear function on semi log paper in the region that is well above the 3 dB cutoff point. In other words, for a single element feedthrough capacitor filter that offers 20 dB of attenuation at 10 MHz, that same filter would offer 40 dB at 100 MHz which is one frequency decade above. If one were to take the same feedthrough capacitor and combine with it an inductor element, thereby making it into an L section filter, this now becomes a 2-element filter. A 2-element filter will increase its attenuation effectivity by 40 dB per decade. Using the example as previously illustrated, if an L section filter, which is well above cutoff, exhibits 20 dB of attenuation at 10 MHz, it will exhibit 60 dB of attenuation at 100 MHz which is a very dramatic increase in filtering effectivity.

This is uniquely advantageous in an implantable medical device in that one can greatly increase the amount of attenuation of the EMI filter in frequency ranges at 1 MHz and above where many problem emitters transmit. For example, in the 22 and 72 MHz frequency ranges, hand held or chest strap transmitters are commonly used to control model airplanes, model helicopters and remote control boats. These sophisticated devices produce powerful digitally controlled signals which can be in very close proximity to an implanted medical device. Accordingly, a two element EMI filter can be designed such that it offers very low attenuation in the cardiac sensing and telemetry ranges of the implantable medical device, but increases the attenuation curve very steeply above these frequencies. Accordingly, there is a need to provide multi-element filters for implantable medical devices.

As described herein, adding inductance in series with pacemaker or implantable defibrillator leads is dramatically effective. It has been found that the input impedance $Z_{IN}$ in pacemaker biological signal sensing circuits is relatively high at low frequencies ($Z_{IN}$ above 10,000 ohms) but can be quite low and, parasitically variable at high frequencies ($Z_{IN}$ well below 5). It is a novel feature of the present invention that the addition of inductive element to the feedthrough capacitor raises and stabilizes the input impedance of the active implantable medical device (AIMD), particularly at these certain parasitic frequencies. In a two element "L" filter, it is important that the inductor element be placed on the side of the capacitor toward the internal electronic circuitry of the AIMD. By thereby raising and stabilizing the AIMD input impedance, the feedthrough capacitor, which is oriented toward the body fluid side, first intercepts and thereby becomes much more effective in bypassing high frequency EMI signals to the overall equipotential shield or housing of the AIMD. This shunting of undesirable signals prevents EMI signals from entering into the AIMD housing where they could interfere with proper AIMD circuit and therapy functions.

Exemplary ferrite beads and wire-wound inductors 30–34 are illustrated in FIGS. 11–15. FIG. 15 illustrates placing multiple turns of wire 36 through a ferrite or iron-core inductor element 34. This is highly efficient because the inductance of the component goes up as the square of the number of turns. In other words, if one were to place a single turn or a straight lead wire 36 through the ferrite bead element or ferrite core 32, this would be defined as one turn (FIGS. 13 and 14). However, if one were to place additional turns, the inductance would go up as the square of the number of turns. FIG. 15 illustrates a three-turn inductor as counted by three passes of the wire 36 through the center hole of the toroidal inductor core 34. This would have 9 times the inductance of the device as shown in FIG. 13, which has one pass of wire 36 through the center hole. The toroidal inductor material can be made of ferrite, powdered iron, molypermalloy or various other materials which affect inductive properties.

Another major trend affecting active implantable medical devices is the ever-increasing need for smaller size devices. Just a few years ago, implantable cardioverter defibrillators (ICD's) were over 100 cubic centimeters in volume. Today, ICDs are being designed below 30 cubic centimeters. Thus, the size of all components within the active medical device must be as small as possible. Therefore, it is not practical to add inductive or ferrite elements if they are to take up additional space inside the implantable medical device.

Typical values for filter feedthrough capacitors used in medical implant applications range from 390 picofarads all the way up to 9000 picofarads. The average feedthrough capacitor, however, is not very volumetrically efficient. Since only a few electrode plates are required to reach the desired capacitance value (due to the high dielectric constant), typical feedthrough capacitors used in medical implantable devices incorporate a number of blank cover sheets. A typical ceramic feedthrough capacitor used in an active implantable medical device would have a thickness between 0.040 and 0.050 inches. Of that, only about ⅓ to ½ of the total height is actually used to provide capacitance. The rest is used to provide mechanical strength.

Implantable medical device hermetic terminals also pose another unique problem for providing substantial inductance in EMI filters. This comes from the nature of providing a hermetic seal to protect against intrusion of body fluids. A typical multi-turn inductor as described in many prior art applications (and as illustrated herein as FIG. 15) can be held loosely in one's hands. One can grasp a length of wire 36 and pass it back and forth through the center forming a multi turn inductor 34, as shown in FIG. 15. There are also a number of automatic winding device hermetic terminal, the lead wire is solidly captured at one end by the nature of the hermetic terminal (usually by a gold braze or the like). The capacitor must be mounted to the hermetic terminal in accordance with one of the many prior art references. A dilemma exists in how to make multiple turns with a bonded ferrite or a bonded ferrite slab.

Accordingly, there is a need to provide multi-element filters for implantable medical devices such that the EMI filter is designed to offer a very low attenuation in the cardiac sensing and telemetry ranges of the implantable medical device, but increase the attenuation curve very steeply above these frequencies to take into account the EMI produced by environmental emitters. Such filters should be volumetrically efficient so as to be the smallest possible size while having sufficient mechanical strength. Such filters should also be able to be hermetically sealed to protect against intrusion of body fluids into the implantable medical device. The present invention fulfills these needs and provides other related advantages.

SUMMARY OF THE INVENTION

The present invention resides in a feedthrough terminal assembly which advantageously incorporates an inductor in the feedthrough capacitor assembly. Incorporating inductors in accordance with the present invention renders the EMI filter a two element (two-pole) or three element (three-pole) device and improves the EMI filter over wider frequency ranges. In particular, the filtering efficiency measured as insertion loss (dB) is greatly improved. Such assemblies are particularly suitable for human implantable device applications, such as cardiac pacemakers, implantable defibrillators, cochlear implants and the like.

Broadly, the invention comprises a feedthrough terminal assembly that includes a conductive ferrule, a feedthrough capacitor, and an inductor closely associated with the capacitor in non-conductive relation. The feedthrough capacitor includes first and second sets of electrode plates. The second set of electrode plates are conductively coupled to the ferrule. A conductive terminal pin extends through the capacitor such that it is conductively coupled to the first set of electrode plates, and through the inductor in non-conductive relation.

Preferably, the feedthrough terminal assembly is configured for use in an active implantable medical device. Under such circumstances, the conductive ferrule is conductively coupled to a housing for the active implantable medical device. Typically, such devices comprise a cardiac pacemaker, an implantable defibrillator, a cochlear implant, a neurostimulator, a drug pump, a ventricular assist device, a gastric pacemaker, an implantable sensing system, or a prosthetic device.

In some embodiments, the inductor is bonded directly to the capacitor utilizing a non-conductive polyimide, glass, ceramic bonding material, epoxy, silicone, or a thermal plastic supportive tape adhesive.

The inductor typically comprises a high permeability ferrite material. Such a material may be selected from scintered alloys of cobalt zinc ferrite, nickel zinc ferrite, manganese zinc ferrite, powdered iron, or molypermally.

A conformal coating is typically provided over the inductor. In the preferred embodiment, the coating disclosed comprises Paralyne. Further, an insulator is typically disposed between the inductor and the terminal pin. The insulator may comprise an epoxy, a thermal-setting non-conductive adhesive, a non-conductive polyimide, or a silicone material.

In an alternative embodiment, a second inductor is provided through which the terminal pin extends in non-conductive relation. The first and second inductors may be disposed adjacent to one another or on opposite sides of the capacitor. In this regard, at least one additional inductor may be stacked onto another one of the inductors, and such inductors may each be comprised of materials having different physical and electrical properties. Alternatively, the inductors may each be comprised of materials having the same physical properties. Further, the capacitor and the inductor may be housed within the ferrule, and an insulative cap may be disposed over the inductor opposite the capacitor.

When the inductors are disposed on opposite sides of the capacitor, various configurations are possible. In one, at least one of the inductors may be disposed on a body fluid side of the feedthrough terminal assembly. Further, the second inductor may be disposed adjacent to the ferrule. Alternatively, the inductors may be bonded to opposing surfaces of the capacitor. In an illustrated embodiment wherein a pair of inductors are disposed on opposite sides of the capacitor, the capacitor and the inductors are disposed within and conductively isolated from the ferrule.

In another illustrated embodiment, first and second feedthrough capacitors are associated with the inductor in non-conductive relation. The first and second feedthrough capacitors may be disposed on opposing surfaces of the inductor and, further, each capacitor may be internally grounded. The first and second capacitors each include a first set of electrode plates conductively coupled to the terminal pin, and a second set of electrode plates conductively coupled to the ferrule. The first capacitor comprises an internally and externally grounded capacitor, and the second capacitor comprises an internally grounded capacitor. The feedthrough terminal assembly further includes a conductive material extending through both the first and second feedthrough capacitors to conductively couple the second set of electrode plates to the second capacitor with the second set of electrode plates of the first capacitor. The conductive material may comprise a thermal setting conductive adhesive, a solder or a solder paste. Alternatively, the conductive material may comprise a conductive pin. Moreover, the conductive pin may comprise a nail head pin or a pin attached to an underlying hermetic insulator.

The hermetic insulator is typically disposed between the terminal pin and the ferrule, and the capacitor is typically disposed adjacent to the hermetic insulator.

In another illustrated embodiment, the inductor includes an aperture aligned with an aperture of the capacitor through which a leak detection gas can be detected.

The capacitor's second set of electrode plates may be externally grounded to the ferrule, or, alternatively, internally grounded to a ground pin which is conductively coupled to the ferrule.

The terminal pin may be wound about the inductor to form multiple turns. In this case, adjacent portions of the wound terminal pin are electrically insulated from one another. The adjacent portions of the wound terminal pin are encased in a non-conductive material such as a non-conductive sleeve.

The inductor may include a notch for receiving the wound terminal pin. The notch may include a ramp for accommodating the terminal pin, and further the inductor may include multiple notches, each for accommodating a separate terminal pin therein. In some embodiments, the notch includes multiple slots for receiving corresponding multiple turns of the terminal pin. The notch may further comprise contoured corners for accommodating the terminal pin.

In several embodiments, means are illustrated for maintaining the conductor in close association with a capacitor without forming a direct physical attachment therebetween. The inductor maintaining means comprises a lock between the terminal pin and the inductor. The lock typically comprises a mechanical lock such as a swage, a clamp or an epoxy. The lock may, alternatively, simply comprise a deformation in the terminal pin.

The inductor maintaining means may further comprise a wire bond pad attached to the terminal pin. When a wire bond pad is provided, it may or may not be physically attached to the underlying structure of the hermetic terminal assembly apart from the terminal pin itself.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 7 describes the capacitor reactance equation and illustrates how the capacitor reactance varies in ohms vs. frequency for an ideal capacitor;

FIG. 8 illustrates the equation for the inductive reactance;

FIG. 9 illustrates schematic diagrams of common EMI filter circuits;

FIG. 11 is a perspective view of a prior art ferrite slab toroidal inductor;

FIG. 12 is a cross-sectional view taken generally along line 12—12, of FIG. 11;

FIG. 13 is a perspective view of a prior art toroidal ferrite inductor with one turn or a single pin going through the center thereof;

FIG. 14 is a cross sectional view of the toroid of FIG. 13 taken generally along line 14—14;

FIG. 15 is a perspective view of a prior art toroidal inductor with multiple lead wire turns;

FIG. 16 is a chart giving the mechanical properties of a thermal plastic polyimide supportive tape adhesive which can be used in accordance with the present invention;

FIG. 58 is a plan view of an inline multi-polar EMI filter with a grounded pin;

FIG. 59 is a cross-sectional view taken generally along line 59—59 of FIG. 58;

FIG. 77 is a perspective view illustrating the mounting of the inline quad-polar ferrite bead of FIG. 76 to a hermetic terminal;

FIG. 78 is the schematic drawing of the quad-polar "L" section filter shown in FIG. 77;

FIG. 79 is a perspective view of a ferrite slab embodying the present invention and having novel slots so that an additional turn can be added making the unit into a two-turn inductor;

DETAILED DESCRIPTION OF THE PREFERRED EMBODIMENTS

As shown in the accompanying drawings for purposes of illustration, the present invention resides in an EMI filter feedthrough terminal assembly which incorporates an inductive element in order to increase attenuation of EMI as the frequency of the EMI increases. The invention is particularly suited for use in human implantable medical devices, as described above.

Figure 17:
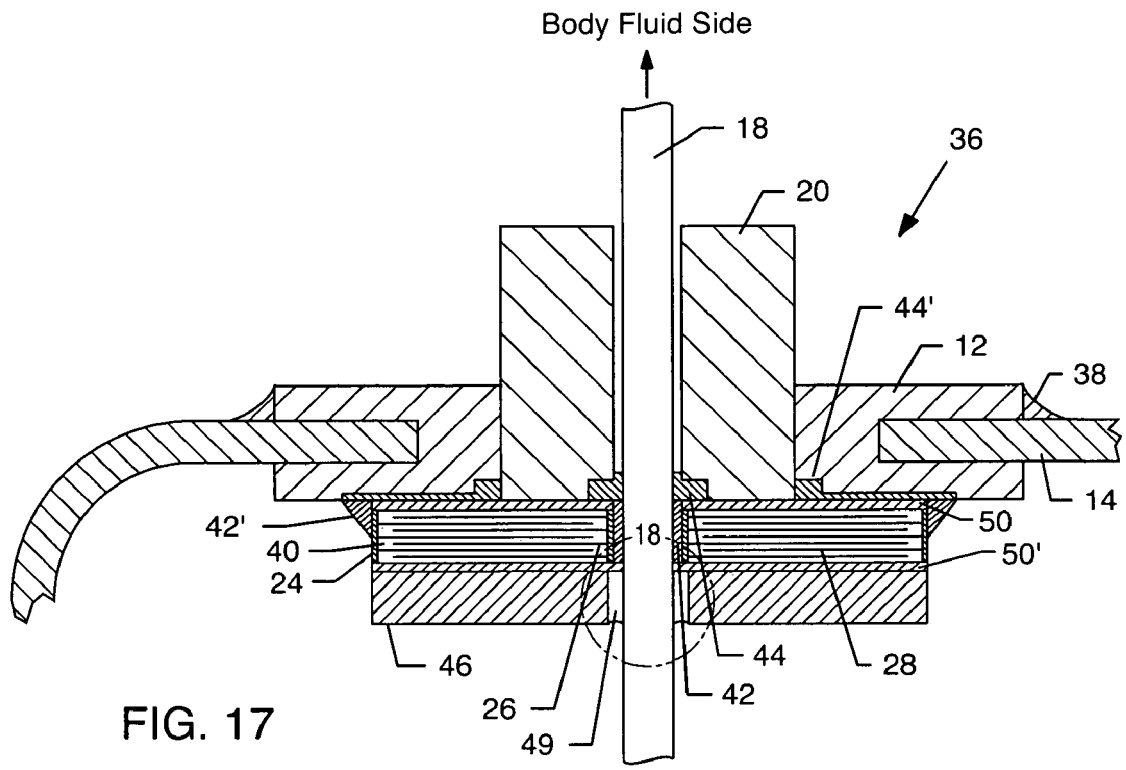
FIG. 17 is a cross-sectional view of an EMI filter embodying the present invention.

With reference now to FIG. 17, an EMI filter feedthrough terminal assembly 36 embodying the present invention is illustrated. Similar to typical implantable device application assemblies, the assembly 36 includes a conductive substrate in the form of a ferrule 12 which is conductively coupled to the housing or casing 14 of an implantable medical device using a laser weld, braze 38 or other appropriate conductive connection as is well-known in the art. A feedthrough capacitor 40 is conductively coupled to the ferrule 12 using a conductive thermal setting material, braze, solder, etc. 42'. A lead wire or terminal pin 18 extends through apertures formed in the ferrule 12 and capacitor 40. Active electrodes 26 of the capacitor 40 are conductively coupled to the terminal pin 18, by solder, conductive thermal setting material, braze 42 or other means that are well-known in the art. Ground electrodes 28 of the capacitor 40 are conductively coupled to the ferrule 12, in this instance between outer metallization 24 of the capacitor 40 and its conductive connection 42' to the ferrule 12. An insulator 20, such as an alumina ceramic, is disposed between the conductive ferrule 12 and the terminal pin 18 so that the terminal pin 18 is in non-conductive relation thereto. The terminal pin 18 may be adhered or otherwise fixed to the insulator 20 by means of gold braze 44 or a glass compression or fusion seal or the like.

The present invention advantageously incorporates an inductor 46 into the assembly 36. The ferrite slab inductor 46 is co-bonded to the capacitor 40 so as to be in non-conductive relationship therewith. The capacitor element 40 is schematically oriented towards the body fluid side and the inductor element 46 is desirably oriented toward the inside of the implantable medical device 14. The reason it is desirable to have the feedthrough capacitor C oriented towards the body fluid side from an electrical circuit point of view is that the cardiac lead wire system represents a fairly stable source impedance. Studies indicate that the source impedance of implanted lead wires tend to be around 80 ohms. This does vary somewhat with frequency, but this is a reliable average. On the other hand, the input impedance of a cardiac pacemaker or other implantable medical device is highly variable with frequency. At low frequencies the input impedance of a cardiac pacemaker tends to be relatively high, on the order of 10 Kohms or more. However, as the frequency increases, the input impedance of the cardiac pacemaker can vary dramatically. At very high frequencies above 20 MHz, the AIMD input impedance ($Z_{IN}$) can shift due to parasitic resonances and coupling between stray capacitance and stray inductance of circuit traces and other components. Accordingly, at certain frequencies the input impedance of the pacemaker might be hundreds of ohms and at a nearby or adjacent frequency the input impedance could plummet drastically to less than 2 ohms. A feature of the inductor L as described in the present invention is that the inductive element stabilizes the input impedance of the cardiac pacemaker. By using the inductor element properties, that is, both its inductive reactance and resistive properties to raise and stabilize the input impedance of the cardiac pacemaker, the feedthrough capacitor C becomes much more effective as a bypass element. In other words, when EMI is induced on the cardiac lead wires, that EMI comes from a source impedance of approximately 80 ohms. It then encounters the feedthrough capacitor C which represents a very low impedance to ground. The inductive element L also blocks the EMI from getting into the input circuits of the implantable medical device because, by representing a relatively high impedance, the EMI is desirably shunted to ground through the feedthrough capacitor C.

Figure 20:
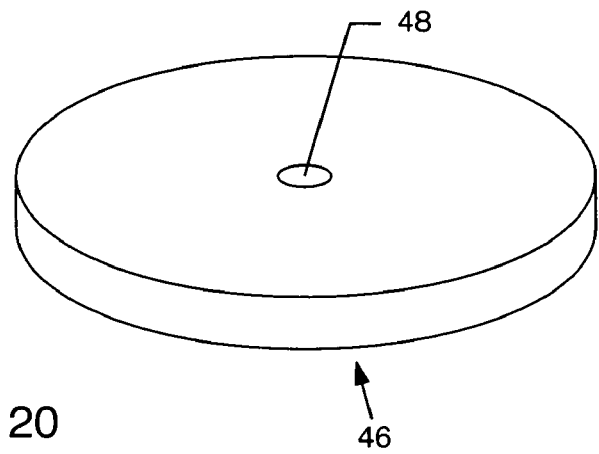
FIG. 20 is a perspective view of the ferrite slab inductor 46 of FIG. 17.

With reference to FIG. 20 and FIG. 17, the terminal pin 18 extends through an aperture 48 of the inductor 46. The space between the lead wire 18 and the inside diameter of the inductor 46 defines an air gap 49. This air gap is desirable in that there is no electrical connection at all required between the inductor 46 and the lead wire 18. In fact, it is preferable that the inductor 46 be maintained in insulative relationship with all of the surrounding elements, including lead wire 18, the ceramic capacitor 40 and the ferrule 12. In a low voltage device, the air gap 49 does not present a problem. However, in high voltage devices such as implantable cardioverter defibrillators, air gap 49 needs to be controlled.

Figure 10:
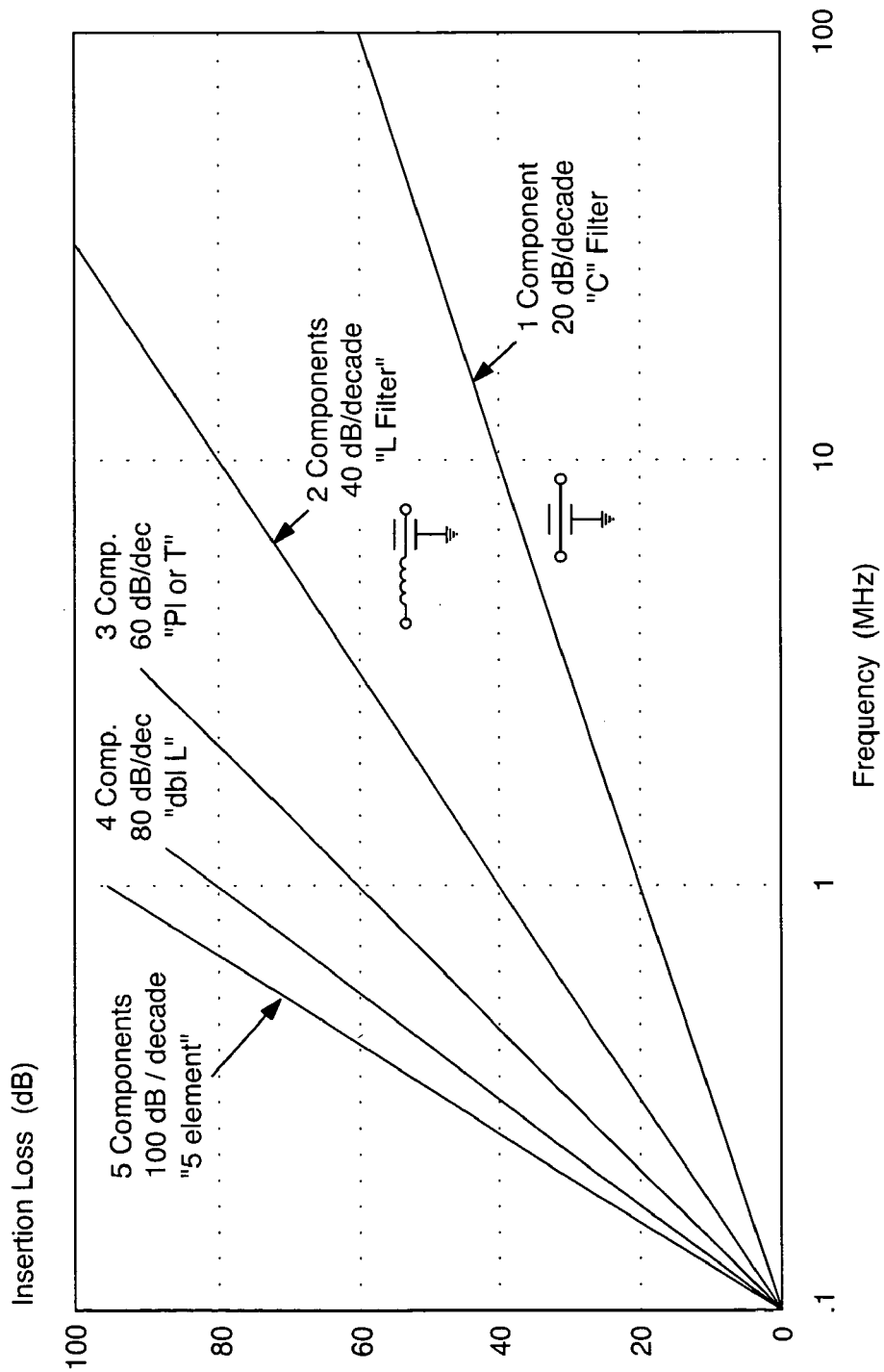
FIG. 10 is a comparison chart of insertion loss vs. number of components in a low pass EMI filter.

The aperture 48 is aligned with apertures in the capacitor 40 and ferrule 12. As can be seen in the schematic diagram FIG. 19, the assembly 36 becomes a two element "L" circuit EMI filter. As shown in FIG. 10, this has the desired effect of greatly increasing the insertion loss or filtering efficiencies throughout the frequency range. Whereas a single component "C" filter, such as that illustrated in FIG. 1, has an insertion loss slope of 20 dB per decade, the two component "L" filter circuit of FIG. 17 has a 40 dB per decade slope, which is highly desirable.

Figure 1:
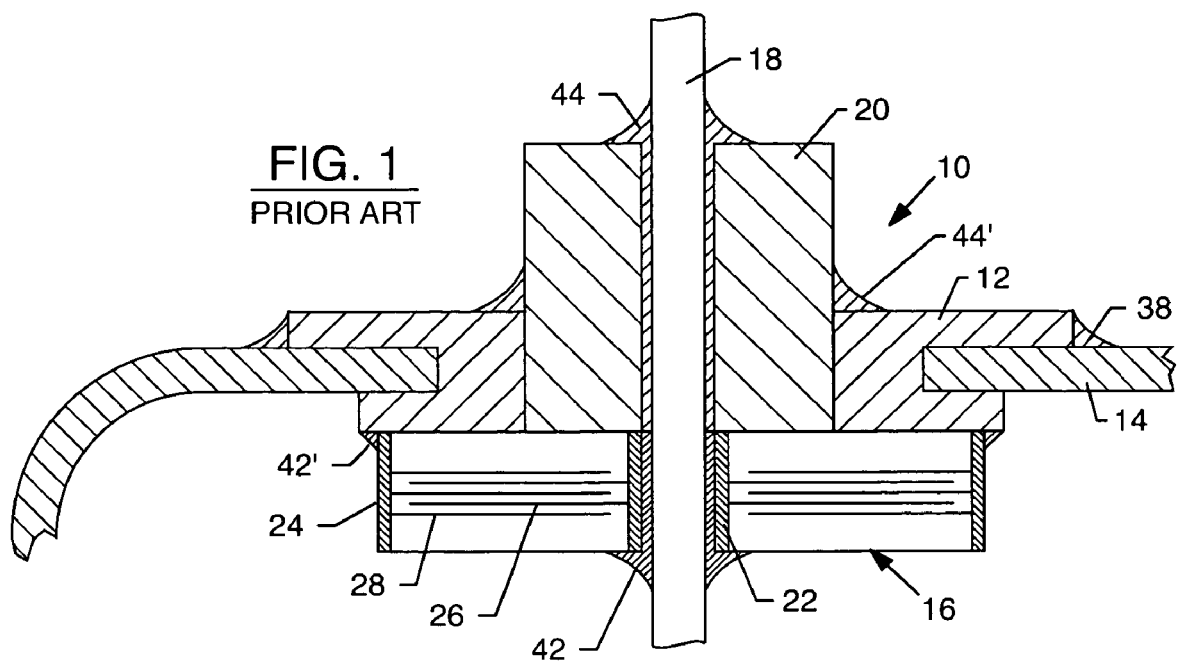
FIG. 1 is a cross-sectional view of a surface prior art mounted discoidal capacitor in an EMI filter assembly.
Figure 2:
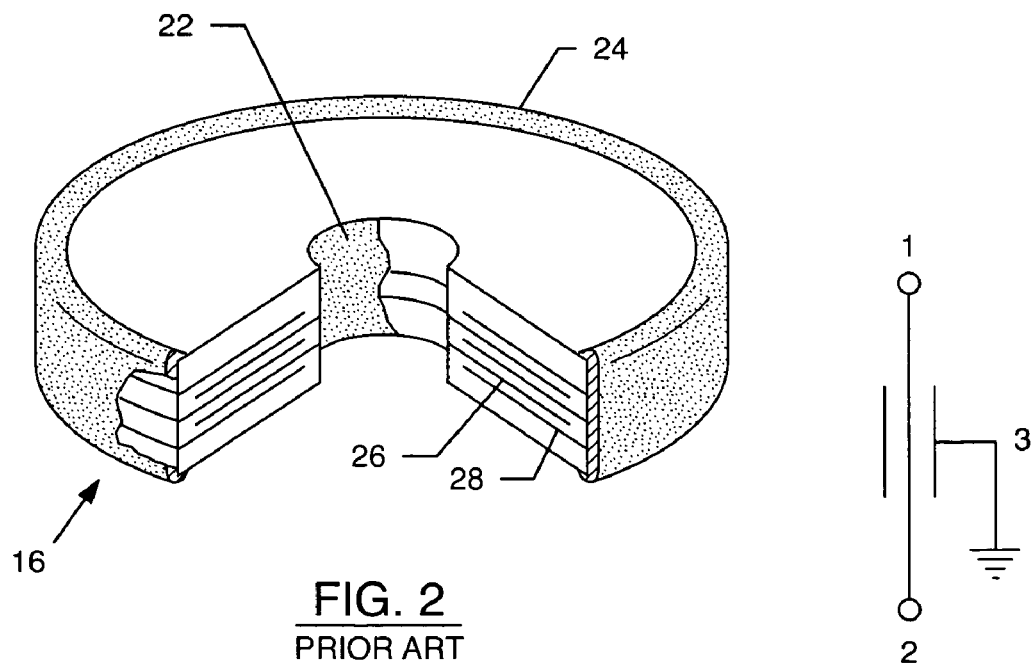
FIG. 2 is a partially sectioned prior art uni-polar discoidal feedthrough capacitor of FIG. 1.
Figure 3:
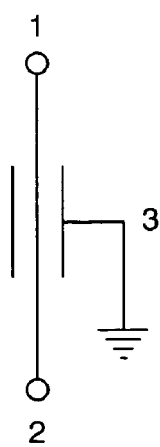
FIG. 3 is a schematic drawing of the feedthrough capacitor of FIG. 2.
Figure 4:
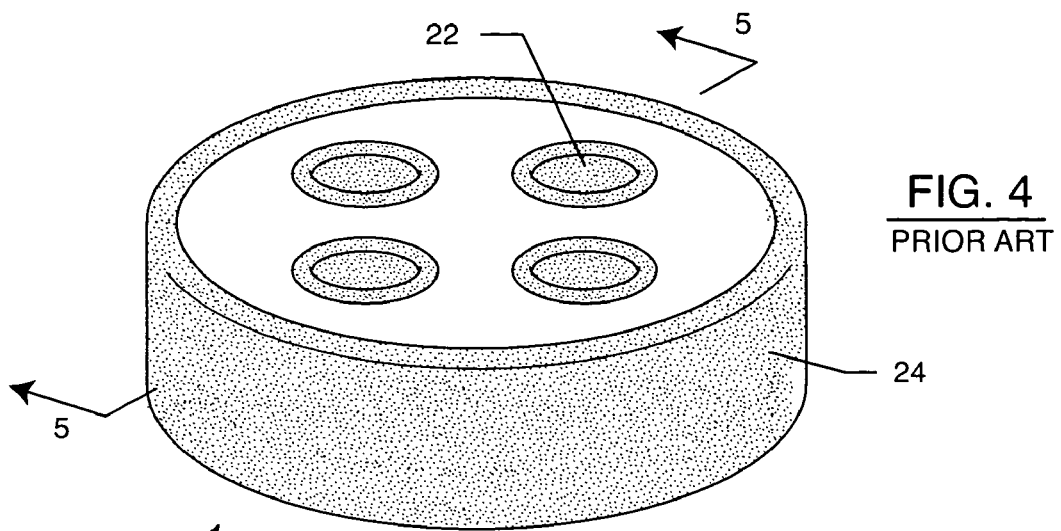
FIG. 4 is a perspective view of a prior art quad-polar feedthrough capacitor.
Figure 5:
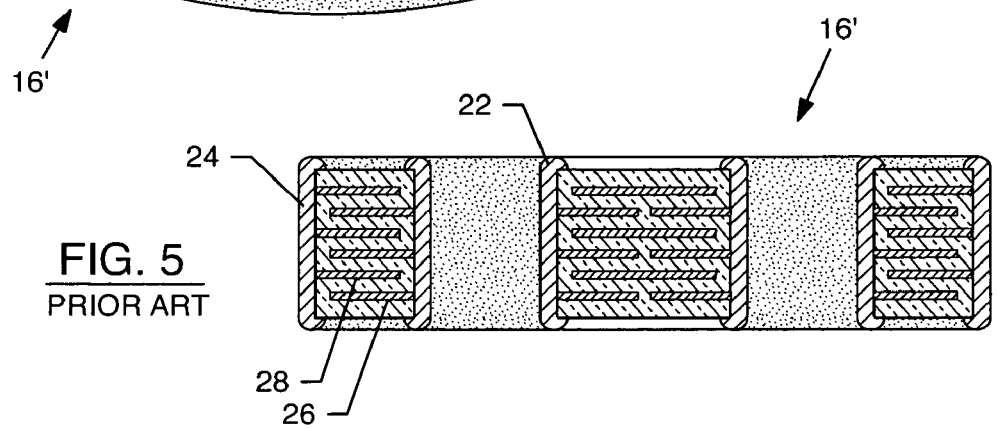
FIG. 5 is a cross-sectional view taken on the line 5—5 in FIG. 4.
Figure 6:
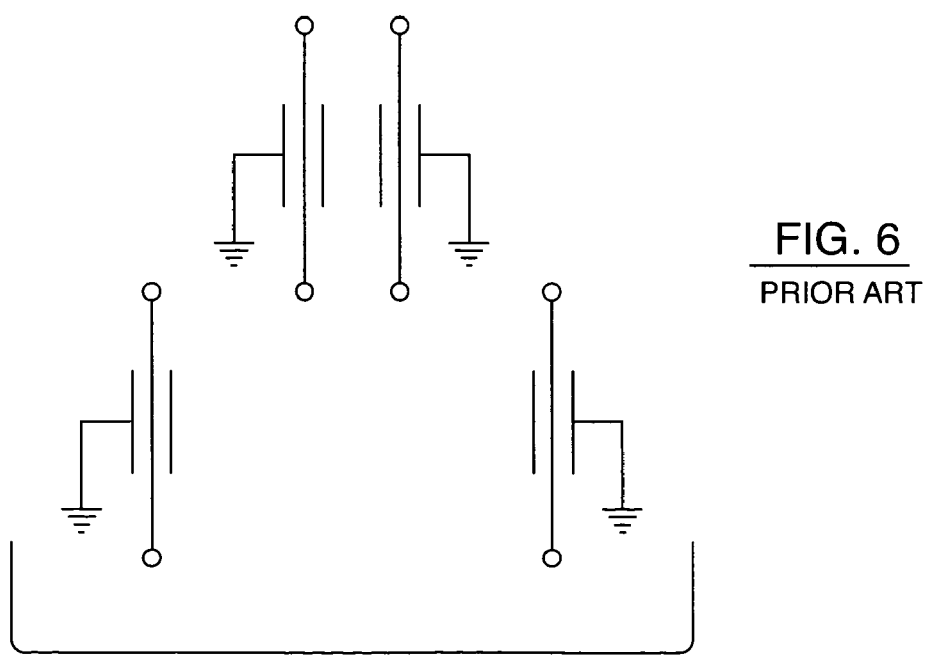
FIG. 6 is a schematic drawing of the quad-polar capacitor of FIG. 4.

Comparing the assemblies 10 and 36 of FIGS. 1 and 17, it will be appreciated that the volumetric efficiency of the capacitor 40 in the invention is enhanced as the co-bonding of the inductor element 46 creates a monolithic structure which has sufficient height for mechanical strength of handling and construction. Referring now back to FIG. 1, one can observe the height of the typical capacitor 16 illustrated. Now referring to FIG. 17, one can see the composite structure consisting of the thinner capacitor 40 and the co-bonded ferrite slab 46, which composite structure has approximately the same height as the original capacitor 16 shown in FIG. 1. This is because the internal electrode plates of the capacitor 16 of FIG. 1 are very efficient and do not require the entire height of the ceramic capacitor 16. Cover sheets or layers are typically added on the top and bottom of the capacitor 16 as shown in FIG. 1, to increase its structural integrity. Another way of saying this is that it is really not possible to build ceramic feedthrough capacitors that are too thin. That is, if they are designed below 0.030 inch in thickness, warpage and cracking during sintering become major factors (this is known in the industry as the potato chip effect). Accordingly, cover sheets are built up to strengthen the ceramic capacitor. In the structure shown in FIG. 17, the co-bonding of the ferrite inductor provides the required strength. Accordingly, the capacitor 40 can be made much thinner.

With continuing reference to FIG. 17, the insertion of the lead wire or terminal pin 18 directly through the inductive element 46 creates a single turn inductor. As shown in FIG. 10, this single turn increases the attenuation rate of the assembly 36 from 20 dB/decade to 40 dB/decade. The inductor 46 capacitor 40 combination, as illustrated in FIG. 17, is desirably on the inside of the ferrule 12. That is on the inside of the pacemaker or implantable medical device housing 14 that is protected from body fluids by the hermetic seal 20. In general, the electronic components of an active implantable medical device are preferably placed inside the hermetic terminal to protect them from the corrosive and conductive effects of body fluid intrusion.

Figure 18:
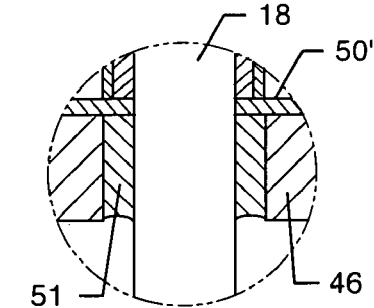
FIG. 18 is an enlarged view of the area 18 taken from FIG. 17, illustrating an alternative embodiment.

In FIG. 17, one can see that there is an air gap 49 between the lead wire 18 and the inside diameter of the ferrite slab 46. This is not a problem in a low voltage application such as for an implantable cardiac pacemaker. However, in a high voltage application such as that of an implantable cardioverter defibrillator, this air gap 49 can present a problem. That is because micro-coulomb or arc type discharges can occur in the high voltage field generated around the lead wire 18 and the inside diameter of the ferrite slab 46. This can occur even though the ferrite slab 46 has been conformally coated with a material such as Paralyne or equivalent insulating materials. The high voltage field that surrounds lead wire 18 tends to relax into the air space surrounding it. The presence of the inductor slab 46 tends to concentrate these equipotential lines of force which can result in the aforementioned micro-coulomb discharges. These would appear during high voltage testing of the device as sudden interruptions in the charging current of the capacitor. This is a particularly undesirable situation in a component for human implant applications because if such discharge occurs in an area of high electric field stress, it could lead to a catastrophic breakdown or avalanche of the device. FIG. 18 illustrates this same air gap 49 which has been back filled with an insulating material 51. This insulating material can be a polymer including an epoxy, a thermal-setting non-conductive adhesive, a non-conductive polyimide, a silicone, a glass, a ceramic or or air holes. The presence of the filling material 51 puts a high dielectric strength material into the previously mentioned air gap 49. This prevents the formation of micro coulomb discharges or arcing.

The inductor 46 is typically in the form of a ferrite slab, as illustrated in FIG. 20. Ferrite beads and slabs are typically formed during a powder pressing and sintering manufacturing process (extrusion or machining techniques can also be used). Proprietary powders, including powdered iron, manganese zinc ferrite, nickel zinc ferrite, cobalt zinc ferrite, etc. are formed into the beads or slabs of the final toroidal inductor configuration. The inductor 46 may be comprised of other materials such as a molypermalloy material or other high permeability ferrite material. There are commercially available ferrite materials that have both high permeability and high resistivity properties, making them ideal for medical implant EMI filter applications.

Ferrites are hard ceramic materials which can abrade wire insulation films during winding. The inductor slab 46 is ordinarily tumbled so that sharp edges are rounded. However, if a higher level of insulation protection is desired, a smooth insulative conformal coating can be provided. This coating should be soft to prevent stressing and cracking the core upon curing or during any temperature cycling or temperatures due to bonding. The coating should have a low coefficient of friction and withstand normal environments. Therefore, in an embodiment of the invention, such ferrite bead or ferrite slab 46 is coated with suitable insulation materials such as Paralyne C, Paralyne D, Paralyne E or Paralyne N or other suitable conformal coating material. A conformal coating material also desirably increases the electrical insulation resistance of the inductor 46 to a very high value (within the Megohm or Gigohm range). Accordingly, the conformal coating will also serve to prevent premature battery drain of the implantable medical device.

There are a number of materials that are ideal for co-bonding the ceramic capacitor 40 to the ferrite bead or the ferrite slab 46. In this regard it is important to note that there is actual reference to two bonds. First, there is the bond between the conformal coating to the ferrite slab 46. Second, there is the bond between the conformal coatings, such as Paralyne or the like, and the adhesive material 50. Therefore, it is also important that the conformal coating be well adhered to the ferrite material itself.

It should be noted that these conformal coatings are typically quite thin. A typical Paralyne coating thickness would be 0.001 to 0.005 inches. Coatings that are excessively thick can be problematic in that they would mismatch the coefficient of expansion of the underlying ferrite material. Because the coatings are so thin, they are generally not shown in any of the drawings. In some of the embodiments that are depicted in the figures herein, it would be possible to use a ferrite inductor without a conformal coating. However, in all of the preferred embodiments, a conformal coating such as a Paralyne coating is incorporated, but not shown.

FIG. 16 illustrates the properties of a thermal plastic polyimide supportive tape adhesive 50 or 50' which can be used as shown in FIG. 17 to co-bond the inductor 46 to the capacitor 40. This tape adhesive 50 or 50' is ideal for bonding the capacitor 40 to the ferrite slab inductor 46. This material has unique properties and it can be di-cut or laser-cut to any desired shape with a variety of through holes. It adheres well to the ceramic capacitor 40, alumina 20, inductor conformal coating, and other surrounding materials, thereby providing a convenient bonding methodology. There are a number of suitable alternative materials described as follows: co-curing 3M one and two part epoxies, Master Bond one or two part epoxies, glasses approved for implantable devices, all ceramics approved for implantable body devices and all non-conductive polymers including polyimides. The important feature is that these materials when bonded and cured are capable of handling the shear stresses that occur in a laminated beam structure as the beam deflects. For example, if the beam deflects downward, the bottom fibers of the beam tend to elongate. The center or neutral access to the beam is where the maximum shear stresses occur. This is where the bending stresses are zero. Accordingly, in order to raise the moment of inertia (I) of the beam, a co-bonding material is required which is capable of handling these substantial shear stresses. Fortunately, the unique geometry of the inductor slab co-bonded to the ceramic capacitor provides ample surface area between the two mating surfaces. Accordingly, a variety of materials are available which can handle the shear stresses that develop in this composite structure.

Figure 19:
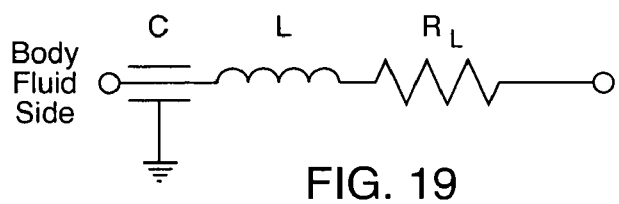
FIG. 19 is a schematic drawing of the EMI filter of FIG. 17.

Referring to the FIG. 19 schematic diagram, we can see that the inductor slab 46 has both an inductive property L and series resistance property $R_L$. It is a property of ferrite materials that both the inductance and the resistive properties vary with frequency. In general the inductance tends to be higher at low frequency and goes down with elevating frequency. On the other hand $R_L$ tends to be a very low number at lower frequencies and tends to get higher in its ohmic value at higher frequencies. This is particularly desirable in an implantable medical device where biologic signals at very low frequencies are being detected by pacemaker sense circuitry. It is a feature of the present invention that $R_L$ be quite low at biologic frequencies so that sensing such frequencies is not impaired. At higher frequencies, $R_L$ acts dramatically to increase the EMI filter performance of the L section filter as shown on the schematic diagram in FIG. 19. The way an L section filter works is that EMI is shunted to ground through the feedthrough capacitor 40. However, if the impedance of the cardiac pacemaker is relatively low, the inductive reactance $X_L$ and the resistance of the ferrite slab $R_L$ both act to raise the input impedance of the implantable medical device. This makes the operation of the feedthrough capacitor assembly 36 much more effective. In other words, the attenuation of the EMI filter capacitor assembly 36 is dramatically improved as both L and $R_L$ go up. Therefore, it is a feature of the present invention that inductor slab 46 have two desirable properties including the property of inductance and high frequency resistance $R_L$.

To maximize the inductance and the resistance of the ferrite slab 46, it is desirable that the inside diameter hole 48 of the ferrite slab 46 fit relatively tightly to the feedthrough lead wire 18. As mentioned, it is desired to have the inductance L and the resistive property $R_L$ to be as high as practicable. This can be done by increasing the overall height of the ferrite bead 46. However, practical manufacturing restrictions exist. These restrictions are based on the fact that, in general, the ferrite slab material 46 is created by a pressed and sintered powder system. The powder is pressed into a die with a central pin which is later extracted after sintering at high temperature. If the ferrite slab 46 gets too thick, it becomes virtually impossible to extract the fixture pin after sintering of the ferrite material into a hard structure.

Another factor that limits the height of the ferrite slab 46 is the amount of physical space that is available inside of the implantable medical device. It is extremely important that every component in an implantable medical device be kept very small, so that the size and weight of the overall medical device is comfortable for the patient and also convenient for surgical implant. However, in some devices there is considerable height that is available. Accordingly, it is preferred that the inductor slab 46 have as much height as possible for a given design.

Figure 21:
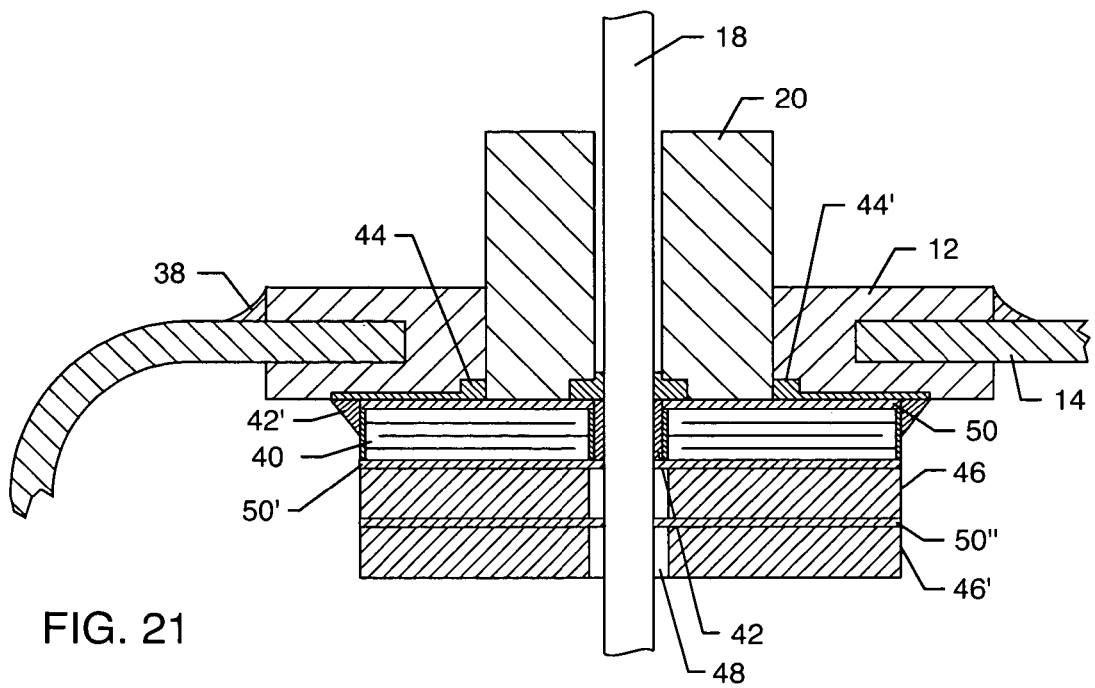
FIG. 21 is a cross-sectional view of an EMI filter assembly embodying the present invention, illustrating multiple inductors 46 and 46' in stacked or laminated relationship.
Figure 23:
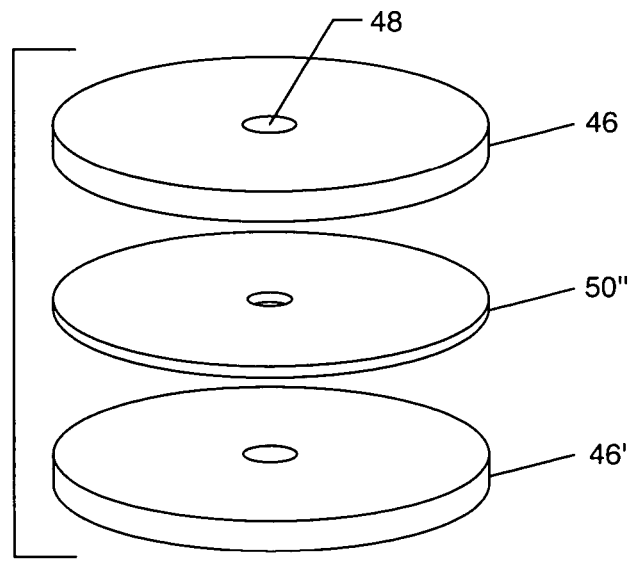
FIG. 23 is an exploded perspective view of the laminated inductors of FIG. 21.

FIGS. 21 and 23 illustrate a novel feature of the present invention in that ferrite slabs with a very small center hole can be manufactured and then layered to provide the overall height to optimize both the inductive and resistive properties. In FIG. 21 one sees that there are two ferrite slabs 46 and 46' which have been bonded together with a non-conductive insulating washer 50" (see FIG. 16). This allows one to increase the overall height of the ferrite slab without running into the fixturing problems if one tried to manufacture this as a single element. As previously mentioned, for a single inductor slab, the height and inside diameter ratio could be quite problematic in the manufacturing operation.

It will be obvious to one skilled in the art that two, three or a number of ferrite slabs 46 can be co-bonded together to achieve any desired height and total inductance that is required.

Figure 22:
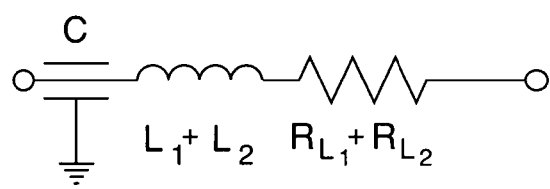
FIG. 22 is a schematic drawing of the EMI filter assembly of FIG. 21.

The schematic diagram shown in FIG. 22 illustrates the effect of having these two inductors 46 and 46' acting in series with their two resistive properties acting in series. These elements simply add up which increases the overall inductance and the overall resistance of the ferrite slab. However, this does not change the basic L circuit EMI filter configuration. In other words, the addition of a second ferrite slab 46' means that the EMI filter of FIG. 21 still acts as a two element L section filter. It is only when you separate the ferrite slabs by a capacitor element that you increase the number of poles or elements of the EMI filter, as described further herein.

Referring now back to FIG. 21, one can see that a plurality of ferrite slabs 46 and 46' can be co-bonded together. These slabs can be of various initial permeabilities and properties. For example, the first slab 46 could be of manganese zinc material and slab 46' could be of cobalt zinc material. These two materials have markedly different electrical properties. One material has higher inductance at low frequency whereas the other material has higher inductance at higher frequencies. By co-bonding beads or slabs 46 and 46' of various materials together, one can optimize inductance throughout wider frequency ranges. The same is true of the resistive property $R_{L1}$ and $R_{L2}$ Of the two ferrite slabs 46 and 46'. Each type of ferrite material has different resistance versus frequency properties. By combining various materials one can also optimize the amount of resistance versus frequency.

Figure 24:
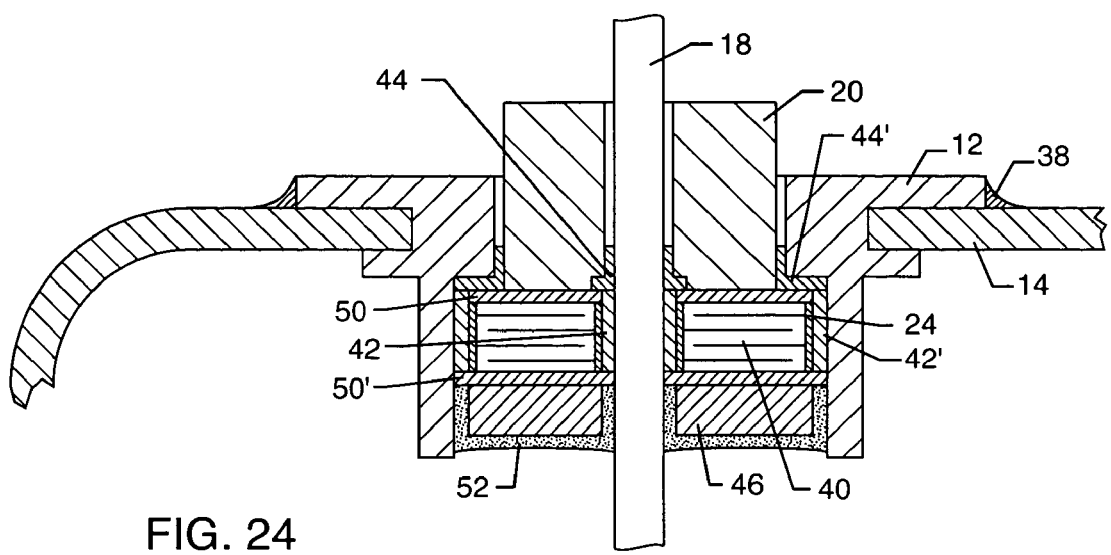
FIG. 24 is a cross-sectional view illustrating placement of the ceramic capacitor and inductor completely inside of a surrounding ferrule.
Figure 25:
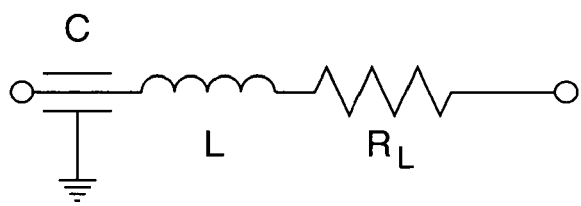
FIG. 25 is an electrical schematic drawing of the two-element inductor capacitor EMI filter of FIG. 24.

Another novel method of building an L circuit filter is the embedded approach, illustrated in FIG. 24. In this case, the ceramic capacitor 40 has been placed completely inside a surrounding ferrule 12. The inductor slab 46 is then co-bonded to the capacitor 40, preferably oriented toward AIMD circuitry as illustrated. This electrical connection from the capacitor outside diameter metallization 24 and gold braze 44' of ferrule 12 is performed using connection material 42' in accordance with U.S. patent application Ser. No. 10/377,086, the contents of which are incorporated herein, utilizing oxide resistant biostable conductive pads. An optional epoxy cap 52 can be placed over the top of the ferrite inductor 46, primarily for cosmetic purposes. The resulting L circuit is illustrated in the schematic diagram of FIG. 25, which as shown in FIG. 10 gives rise to an attenuation slope of 40 dB/decade.

Figure 26:
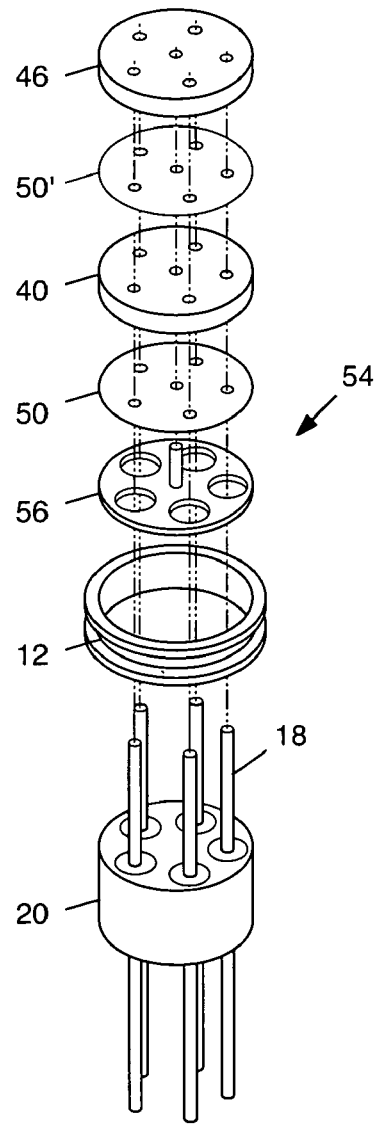
FIG. 26 illustrates an exploded perspective view of a five pole or penta polar capacitor assembly that is internally grounded embodying the present invention.

The present invention is not limited whatsoever in the number of terminal pins or the EMI feedthrough terminal assembly design. For example, FIG. 26 illustrates an exploded view of an internally grounded pentapolar feedthrough capacitor hermetic terminal 54 with mounted feedthrough capacitor 40, inductor 46, and alumina insulator 20 with five gold brazed leadwires 18 which are typically platinum, or platinum-iridium or the like. A ground plate 56 is typically attached to the ferrule 12 by laser welding or the like. An insulating washer 50 is then placed on top of the ground plate 56. An internally grounded feedthrough capacitor 40 in accordance with U.S. Pat. No. 5,905,627 is then placed and attached to the lead wires 18. Insulating washer 50' is then placed on top of capacitor 40 to which inductor 46 is assembled in accordance with the present invention. Accordingly this makes a very efficient pentapolar L section filter.

Figure 27:
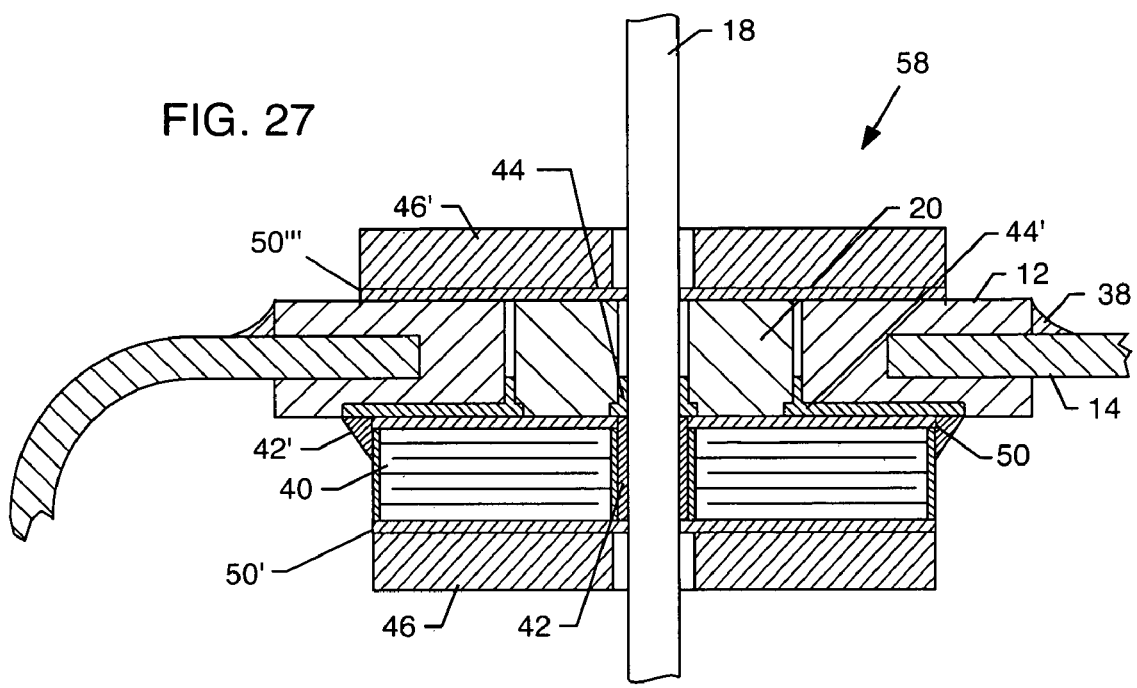
FIG. 27 is a cross-sectional view of an EMI filtered hermetic terminal assembly modified by shortening the alumina insulator thereof to provide a convenient bonding surface to install a second ferrite bead 46' on the body fluid side of the assembly.
Figure 28:
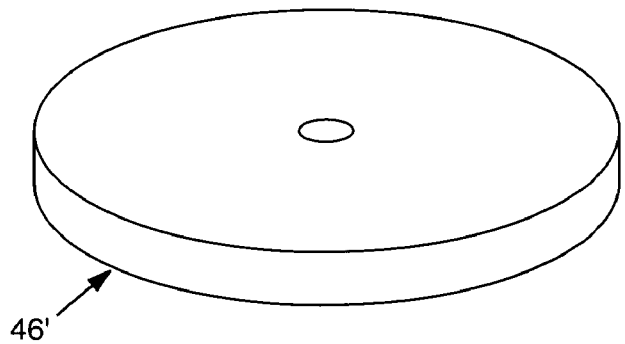
FIG. 28 illustrates the second ferrite slab of FIG. 27.
Figure 29:
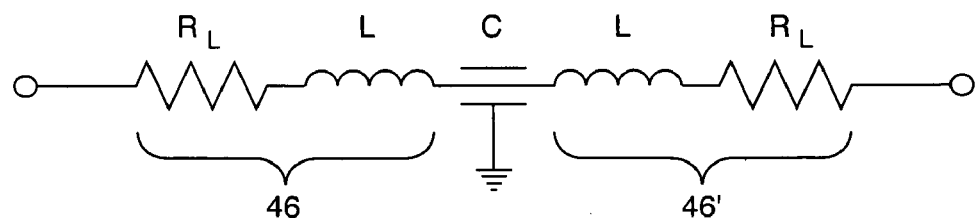
FIG. 29 is a schematic drawing of the filtered hermetic terminal assembly of FIG. 27.

Adding even more inductor elements to the EMI filter additionally increases its attenuation rate per decade. FIG. 27 illustrates a three element "T" section low pass filter assembly 58 wherein there are ferrite slab inductor elements 46 and 46' which appear electrically on both sides of the feedthrough capacitor 40. Such a three-element filter will have an attenuation rate of 60 dB per decade, as shown in FIG. 10, which is even more highly desirable. This is also shown as the T circuit schematic of FIG. 29. Another feature of the invention as shown in FIG. 27 is that there is a biocompatible conformal coating over the ferrite bead inductor element 46'. This provides an additional level of protection from intrusion of body fluid in the inductor element 46'. In addition, the inductor element 46' is encapsulated underneath the pacemaker or implantable defibrillator header block (not shown). This provides additional protection from the intrusion of body fluid.

In summary, placing the inductor 46' on the body fluid side is accomplished in three main ways. That is, the ferrite material is a hard fired material that in and of itself is not prone to leaching out and therefore has its own degree of biocompatibility. The adjunct conformal coating of silicone, Paralyne or other biocompatible coating assists in its biocompatibility as well as the placement of adjunct sealants in the header block.

With continuing reference to FIG. 27, a ferrite slab inductor 46 is co-bonded directly to the ceramic capacitor 40, such as by an adhesive washer 50'. In this regard, it is identical to the structure shown in FIG. 17. However, on the body fluid side, a second inductor slab 46' is bonded directly to the hermetic terminal 12, such as by an adhesive washer 50'''. In this case, the inductor ferrite bead or the inductor slab 46' is directly exposed to body fluid or on the body fluid side of the device 14. In a typical implantable medical device, a header or connector assembly (not shown) is placed over this area with some sort of a sealant such as silicone and the like. However, it is still possible for body fluids and electrolytes to penetrate down to the layer of the ferrite. A unique aspect of the invention is the use of ferrite material which during sintering is highly bound to various elements including iron. This makes the composite structure biocompatible. Examples of such ferrite material include Manganese Zinc, Nickel Zinc or Cobalt Nickel.

Figure 30:
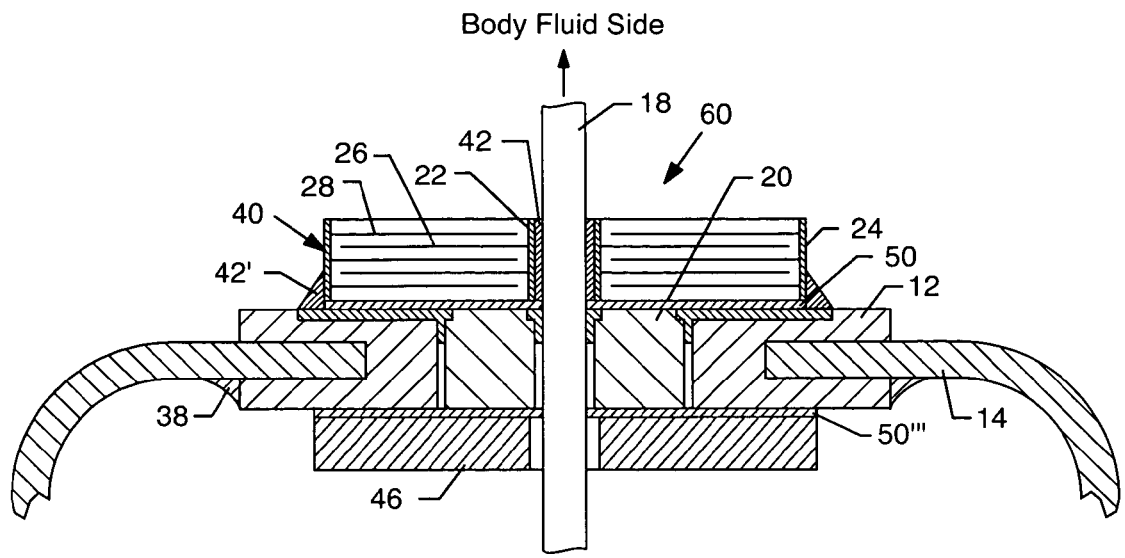
FIG. 30 is a cross-sectional view of an EMI filtered assembly having a ceramic capacitor disposed on the body fluid side and an inductor bonded to an internal insulator.

FIG. 30 illustrates a novel L section filter 60 of the present invention with the inductor slab 46 bonded to the inside of the hermetic terminal 12, such as by a washer 50'''. The ceramic feedthrough capacitor 40 is shown on the outside or body fluid side of the device. In this case there is no conformal coating over the top of the capacitor 40. The materials of the ceramic feedthrough capacitor 40 must all be biocompatible. That is the internal electrodes 26 and 28, the metallization 22 and 24 and the connections 42' from the ferrule 12 to the outside diameter metallization 24 and from the lead 18 to the inside diameter metallization 22 must be of suitable biocompatible materials, as described in U.S. patent application Ser. No. 10/778,954, filed Feb. 12, 2004.

Another advantage of designing with an L or T circuit has to do with the timing of the output circuitry of implantable cardioverter defibrillators. It has been noted that the presence of an EMI ceramic feedthrough capacitor in the high voltage output circuits of an implantable defibrillator can interfere with its timing or cause microprocessor re-sets. This is particularly true when the implantable defibrillator is fired into a no load situation. In other words, this is when the ICD lead wires would not be connected to cardiac tissue.

It is theorized that the leading edge from the implantable defibrillator's pulse causes excessive charging current into the feedthrough capacitor. The energy stored can then reflect back and disrupt implantable defibrillator timing circuitry. The presence of the slab inductor 46 as described throughout this patent application is an advantage in that the series inductance will slow the rise time of this leading edge pulse before it gets to the feedthrough capacitor. In this way, it is a novel aspect of the present invention that higher capacitance value feedthrough capacitors can be used in combination with an inductor without disrupting the sensitive output circuitry of the implantable defibrillator. This is because the series inductance decouples the feedthrough capacitor from the ICD's output circuitry.

Figure 31:
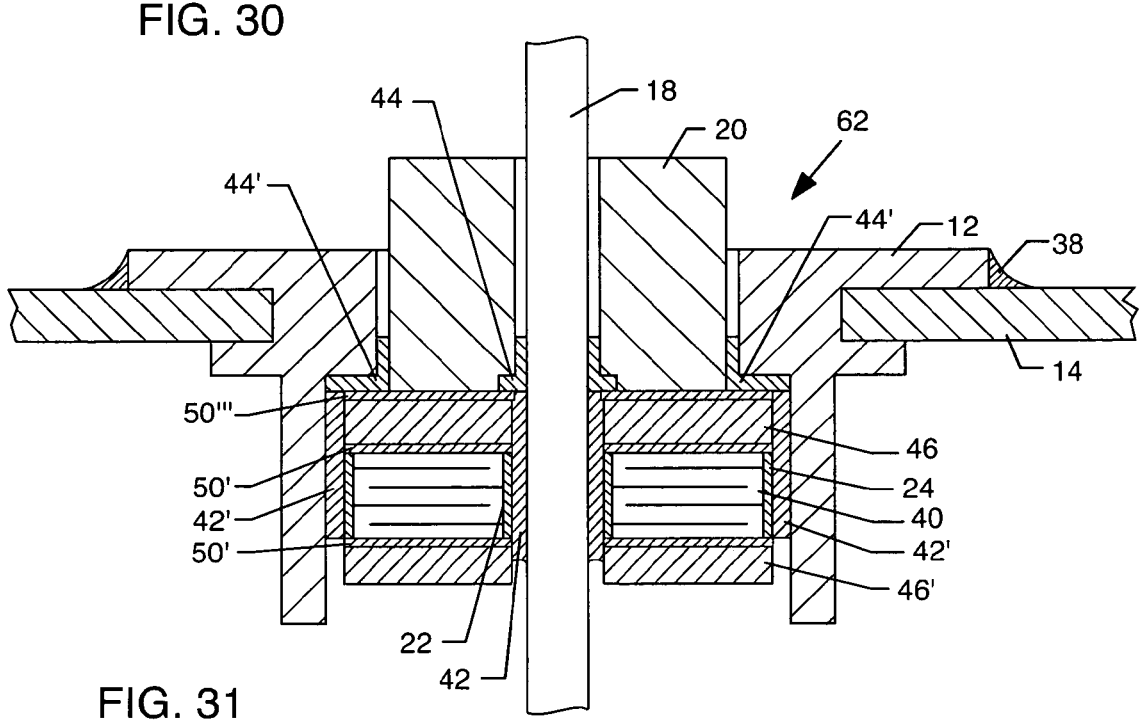
FIG. 31 is a cross-sectional view of an EMI filtered assembly embodying the present invention having inductors co-bonded to opposing surfaces of a ceramic capacitor.
Figure 32:
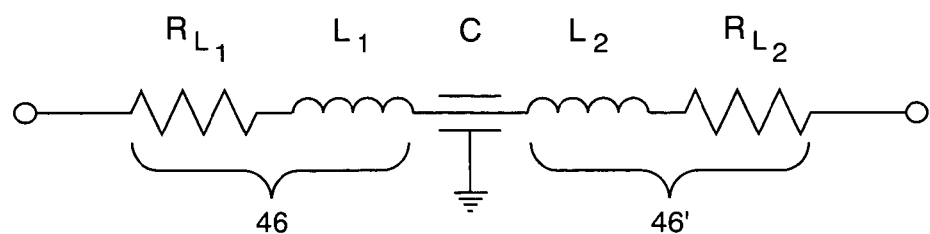
FIG. 32 is an electrical schematic drawing of the EMI filter terminal assembly of FIG. 31.

With reference now to FIGS. 31 and 32, a novel T filter assembly 62 includes two inductor ferrite slabs 46 and 46', which are co-bonded to opposing top and bottom surfaces of the ceramic capacitor 40 within the ferrule 12 such as by insulating washers 50 and 50'''. The schematic of the FIG. 31 "T" filter is shown in FIG. 32. This filter assembly 62 has an attenuation slope of 60 dB per decade, similar to the filter illustrated in FIG. 27.

Further describing the assembly shown in FIG. 31, insulating washer 50''' is first placed into the cavity formed by the ferrule 12. The inductor 46 is then placed on top of the adhesive layer of 50''' and cured in place. Then an insulative layer 50' and a capacitor 40 are placed and cured thereby forming a laminate structure. The electrical connections 42' between the capacitor outside diameter metallization 24 and the ferrule 12 and the capacitor lead wire 18 and the inside diameter metallization of the capacitor 22 are then formed, such as by the insertion of a conductive thermosetting polymer, a solder, liquid solder, solder paste, brazing or the like (42). The thermal setting conductive material 42 or 42 can be injected using a syringe into the annular space between the ferrule and the feed through capacitor-inductor stack and between the annular space surrounding lead wire 18 in the inside diameter of the capacitor and corresponding conductor stack. However, it is very difficult using small needle syringes to inject the relatively viscous conductive thermal setting materials. A preferred methodology of injecting the conductive material 42 and 42' is through centrifuge methods. This is best accomplished by inverting the assembly shown in FIG. 31 and injecting a thermal setting conductive adhesive in its liquid state flooding the entire surface of inductor 46. This material would fill the entire cavity that is formed above inductor 46 and within the inside diameter of ferrule 12. The entire assembly is then centrifuged which injects the thermal setting conductive material 42 and 42' down into the annular spaces as previously described. Typically, a cleaning operation would be followed after this step. At this point an insulating washer 50' with adhesive backing is placed and an inductor 46' is placed on top of the capacitor 40 and seated. There is a final curing operation which co-bonds the entire structure which results in a laminate beam consisting of the inductor 46, the capacitor 40 and the inductor 46'.

As one can see in FIG. 31, insulative washers 50' and 50'" are designed to be the same as dimensionally and to conform to the outside diameter of the capacitor 40 and the outside diameter of the ferrite slabs 46 and 46'. This is important because it allows the conductive thermal setting polyimide or solder 42 and 42' to directly contact the gold braze 44 and 44'. Directly contacting the gold braze as opposed to contacting the titanium is very important to avoid the formation of titanium oxides which can preclude the proper operation of the EMI filter capacitor. This is fully described in pending U.S. patent application Ser. No. 10/377,086. By having the conductive thermal setting polyimide or solder 42 contact the lead wire gold braze 44, this eliminates the necessity for a direct contact between the capacitor metallization 22 and the lead wire 18. This is also described in pending U.S. patent application Ser. No. 10/377,272. The lead wire 18 can then be of any biocompatible material including the group of niobium, tantalum and the like.

One can see that the conductive material 42 and 42' is also in direct contact with ferrite slab 46. It would be undesirable to have material 42 or 42' short out ferrite slab 46. Accordingly, ferrite slab 46 has been conformably coated with a suitable insulating material. This is done prior to assembling ferrite slabs 46 and 46' into the assembly shown in FIG. 31. Suitable conformal coating materials exist in the art and would consist of the group of thermal setting polymers and the like. Two preferred materials are Paralyne C or Paralyne D. These materials are vapor deposited and have excellent dielectric breakdown strength measured in volts per mil. Paralyne D has a higher temperature rating and is ideally suited for use in a hermetic terminal of an implantable medical device. This is important because these terminals are designed to be laser welded from the conductive ferrule 12 to the overall housing 14 of the implantable medical device. This laser weld forms a hermetic seal between the filtered terminal assembly 62 and housing 14 and also makes the ferrule of the hermetic assembly 12 become an overall part of the continuous electromagnetic shield 14 of the implantable medical device. During laser welding a heat pulse is generated which can travel to the ferrite slab 46 or 46' and the feedthrough capacitor 40. Accordingly, it is desirable for all connection materials to be of high temperature construction. Thus, Paralyne D would be preferred insulating material. Connective materials 42 and 42' are also desirably of high temperature ratings. For example, a high temperature solder such as SN10 can be used or a thermal setting conductive polyimide which can easily withstand temperature above 300 degrees centigrade.

Another important reason to use conformal coatings on the ferrite slabs 46 or 46' is for applications in a high voltage device such as an implantable cardioverter defibrillator. When high voltage therapy is applied to the lead wire 18, a very large electric field is generated across the surfaces of the ferrite slab 46 or 46. Paralyne coatings are preferred because they have voltage breakdowns in excess of 1000 volts per mil. A conformal coating of 2–3 mils allows the ferrite slab to withstand voltages of greater than 2000 volts.

Figure 33:
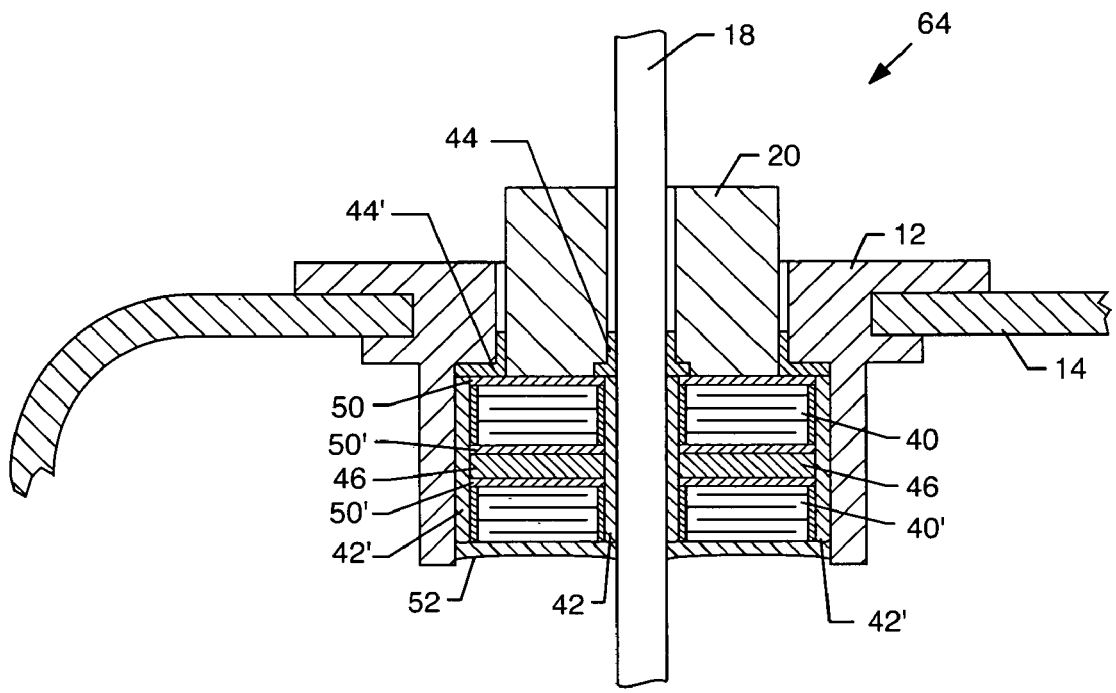
FIG. 33 is a cross-sectional view of a PI filter assembly embodying the present invention.
Figure 34:
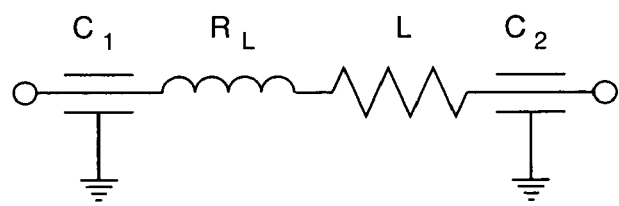
FIG. 34 is an electrical schematic drawing of the EMI filter of FIG. 33.

A novel PI filter 64 is shown in FIGS. 33 and 34. A PI circuit filter is a three-element filter which offers a three element attenuation slope of 60 dB per decade (see FIG. 10). This is the same as the slope for the T element filter that was previously described. In this case, a ferrite slab inductor 46, has been sandwiched between two feedthrough capacitors 40 and 40' as shown. Insulative washers 50' bond and prevent conductive contact between the inductor 46 and capacitors 40 and 40'. Conformal coating on all surfaces of inductor 46 prevents electrical contact between the pin 18, the pin electrical connection material 42, and the inductor 46. Space has been allowed so that the conductive thermal setting materials, such as a silver filled conductive polyimide, can directly contact the gold braze in accordance with pending U.S. patent application Ser. No. 10/377,086.

Figure 35:
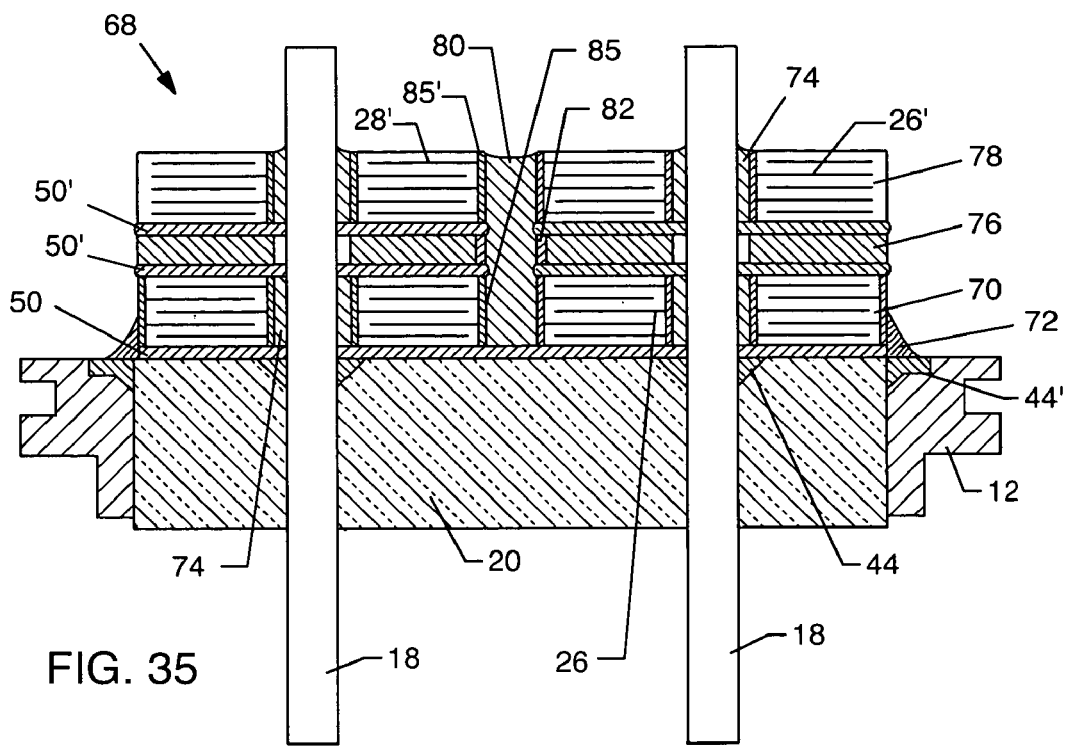
FIG. 35 is a cross-sectional view illustrating a novel PI section filter incorporating capacitors combining both external and internal ground technologies.
Figure 36:
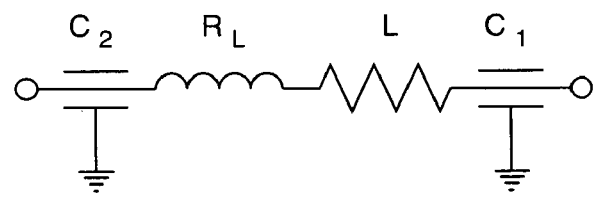
FIG. 36 is an electrical schematic view of the terminal of FIG. 35.

FIG. 35 illustrates a novel PI section filter 68 which incorporates surface mounting techniques. The bottom capacitor 70 is a special hybrid capacitor in that it combines both external ground and internal ground technologies. Externally grounded feedthrough capacitors are well known in the art. Internal grounding is described by U.S. Pat. No. 5,905,627. The schematic for this PI circuit device is shown in FIG. 36. As shown, it is a three element low pass EMI filter which, as shown in FIG. 10, offers 60 dB per decade of attenuation.

The special hybrid capacitor 70 is seated to the hermetic terminal 12 by way of an insulating washer 50. The hybrid capacitor 70 is externally grounded to the gold braze 44' of the ferrule by conductive material 72. The capacitor 70 active electrode plates 26 are also connected to leadwires 18 by conductive material 74. An inductor slab 76 is then bonded to the top of capacitor 70 by way of an insulating washer 50'. A top capacitor 78 is then placed on top of another insulating washer 50' and cured in place to form the laminated stack assembly 68 as shown. Capacitor 78 is a conventional internally grounded feedthrough capacitor, as described by U.S. Pat. No. 5,905,627, the contents of which are incorporated herein. The arrangement of FIG. 35 allows for the upper capacitor 78 to be grounded to the lower capacitor 70 by conductive material 80 so that it forms an effective PI circuit filter or three element filter capable of 60 dB per decade.

The conductive material 80 can be a variety of materials from the group of the thermosetting conductive adhesives such as a conductive epoxy or conductive polyimide, solder or solder paste, and a variety of other conductive materials. It should also be noted that there is an optional insulating surface 82 which prevents the conductive material 80 from shorting to the ferrite bead 76. This can be a conformal coat such as Paralyne C or Paralyne D which surrounds all surfaces of inductor 76 or can be an inserted insulating sleeve 82.

Figure 37:
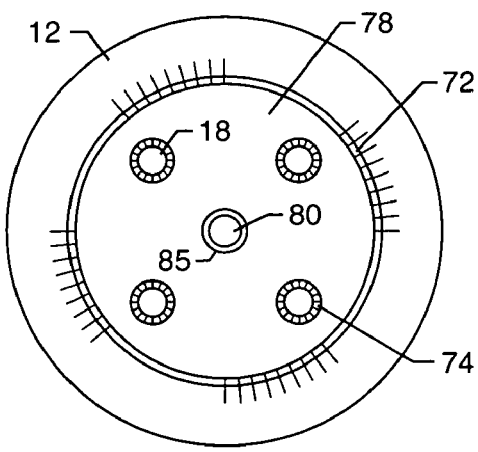
FIG. 37 is one possible top plan view of the assembly of FIG. 35.
Figure 38:
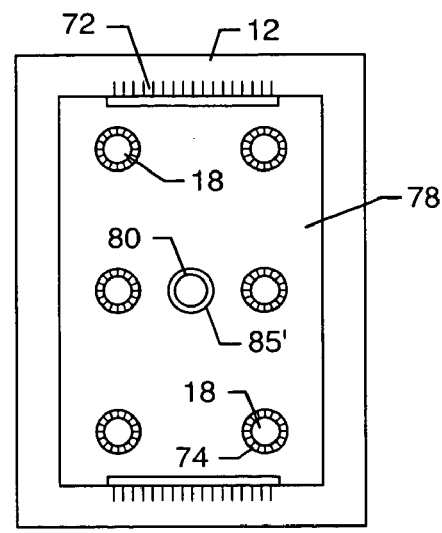
FIG. 38 is a top plan view of another possible configuration of the assembly of FIG. 35.

FIGS. 37 and 38 show two different top views of FIG. 35 illustrating that this technology can be manufactured in either round (discoidal), rectangular, or other geometries. The number of lead wires 18 can be varied in accordance with the intended application.

Figure 39:
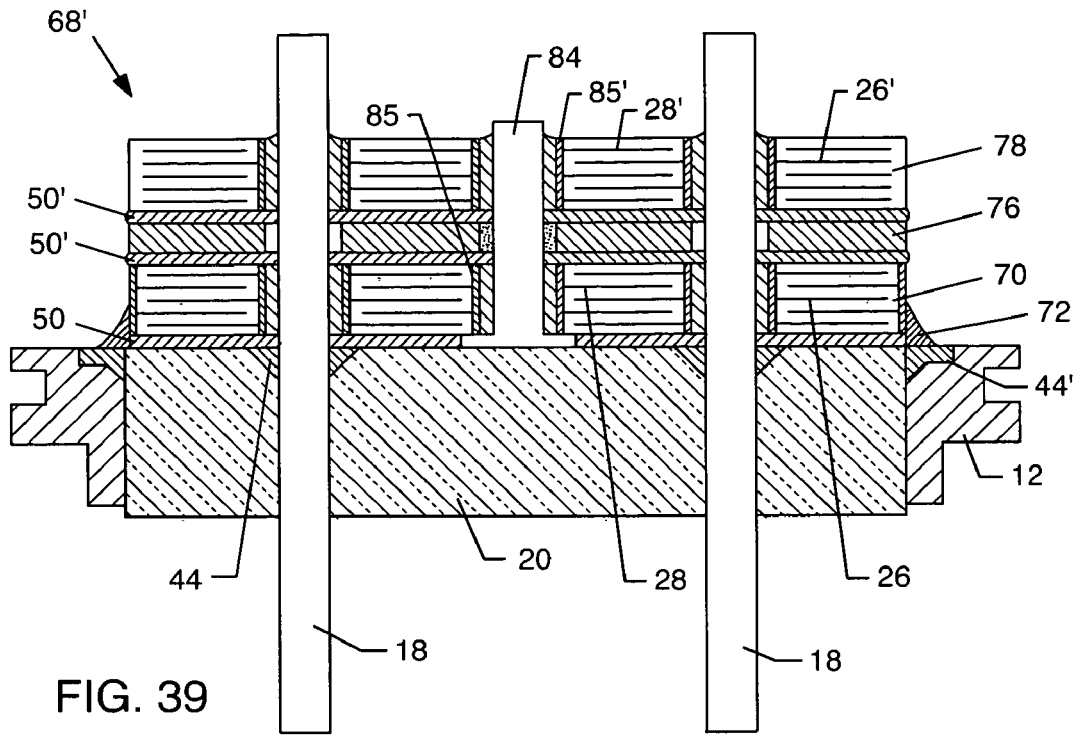
FIG. 39 is a cross-sectional view illustrating another PI filter assembly incorporating hybrid capacitors similar to FIG. 35.

FIG. 39 is a variation of FIG. 35 in that the fill material 80 has been replaced by a conductive pin 84. In the preferred embodiment, this pin 84 would have a nail head configuration as illustrated, which would increase its pull strength as it is captured by the surrounding solder or conductive thermosetting polymeric materials. However, it would be perfectly acceptable to have a straight leadwire without a nail head. The pin 84 could be comprised of a variety of materials including extruded copper, steel, titanium or the like. The pin would be electroplated with tin, silver or a similar solder wettable coating. Since this is on the inside (non-body fluid side) of the device, there is no need for any of the connection materials or the pin to be biocompatible.

Figure 40:
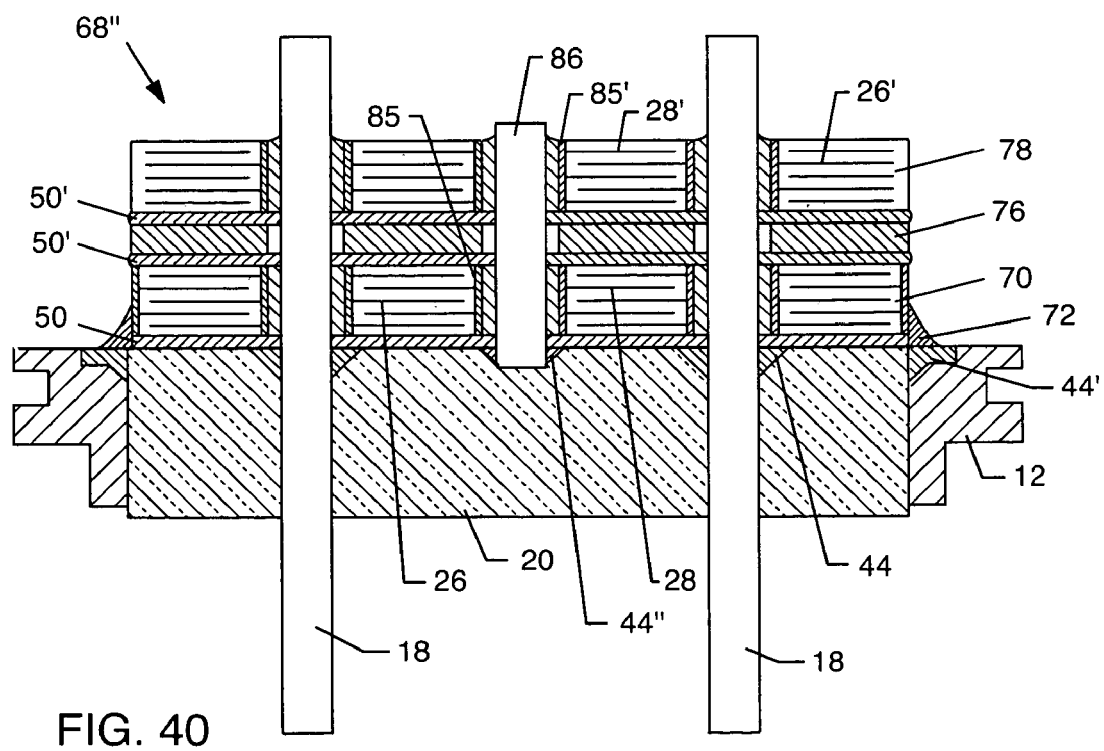
FIG. 40 is a cross-sectional view illustrating yet another novel PI filter assembly incorporating hybrid capacitors.
Figure 41:
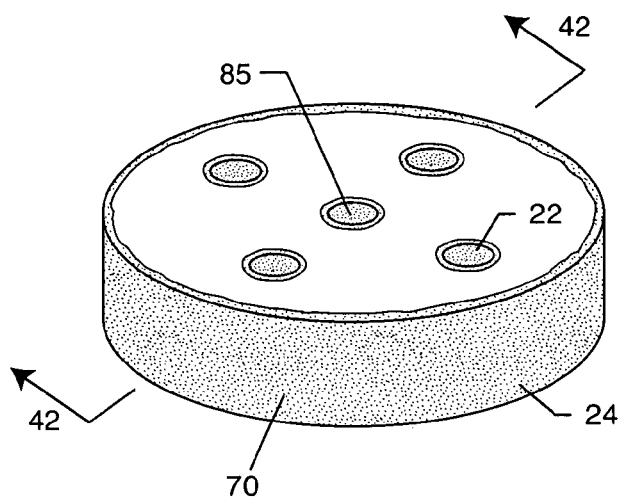
FIG. 41 is a perspective view of the bottom capacitor of FIGS. 35, 39 and 40.
Figure 42:
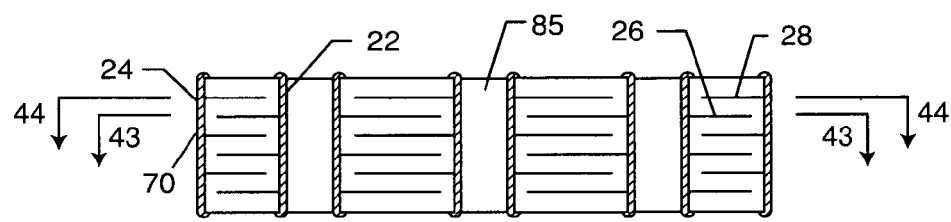
FIG. 42 is a cross-sectional view through the capacitor of FIG. 41 taken generally along line 42—42.
Figure 43:
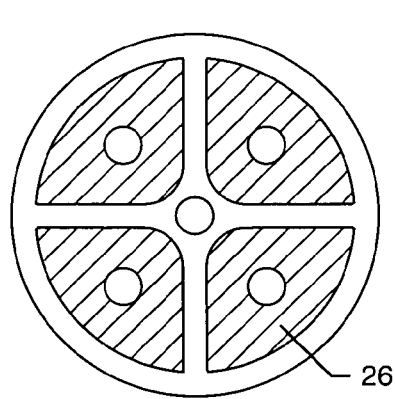
FIG. 43 is a cross-sectional view through the capacitor of FIG. 42 taken generally along line 43—43, illustrating the arrangement of active electrode plates.
Figure 44:
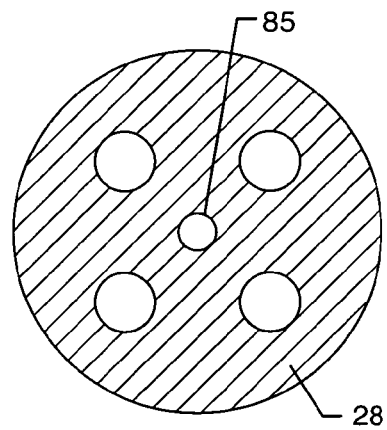
FIG. 44 is a cross-sectional view through the capacitor of FIG. 42 taken generally along line 44—44, showing the configuration of the ground electrode plates.

FIG. 40 is yet another modification of the principals of the PI circuit filter shown and previously described as FIG. 35. In this case, the center pin 86 connects the ground electrode plates 28 of the hybrid capacitor 70 with the ground electrode plates 28' of internally grounded capacitor 78. This pin 86 has the greatest pull strength of all the configurations in that the pin 86 is seated into the aluminum ceramic insulator 20 and mechanically attached to the insulator 20 along with the other pins in a co-brazing operation. Capacitor 70's ground electrode plates 28 connect to this pin 86 which grounds it. The pin 86 in turn couples with the capacitor 78 for grounding its internal electrode plates 28' thereby forming the PI circuit filter schematic shown in FIG. 36.

FIGS. 41–44 show the bottom capacitor 70 of FIG. 35. As can be seen, the ground electrode plates 28 electrically connect to both the centered inner diameter hole metallization 85 and the outside diameter metallization 24 of the capacitor.

Figure 45:
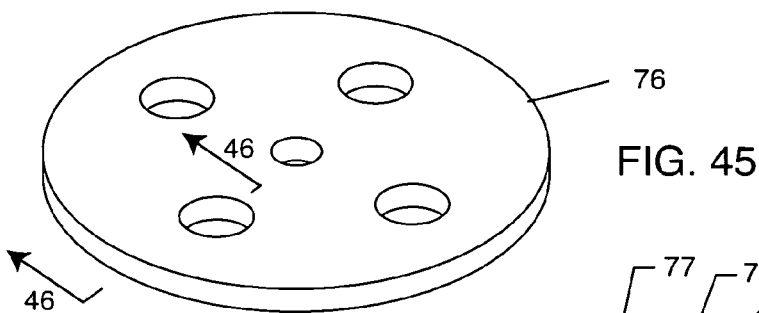
FIG. 45 is a perspective view of the ferrite inductor of FIG. 35.
Figure 46:
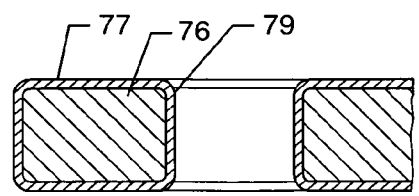
FIG. 46 is a cross-sectional view of the inductor of FIG. 45 taken generally along line 46—46.
Figure 47:
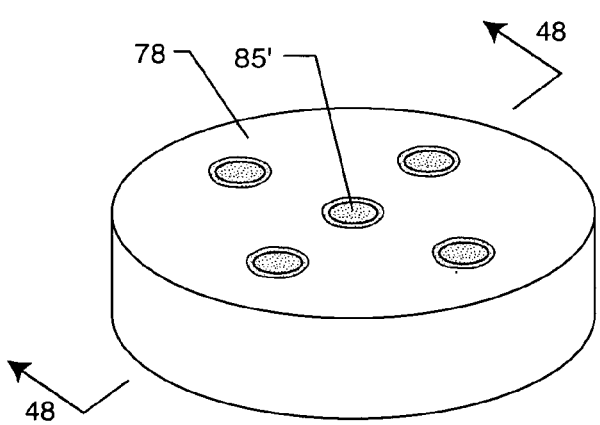
FIG. 47 is a perspective view of the upper capacitor of FIGS. 35, 39 and 40.
Figure 48:
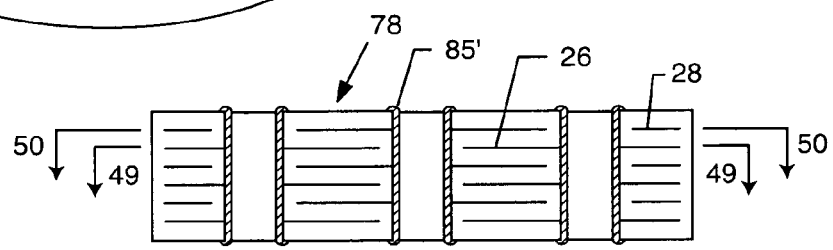
FIG. 48 is a cross-sectional view of the capacitor shown in FIG. 47 taken generally along line 48—48.
Figure 49:
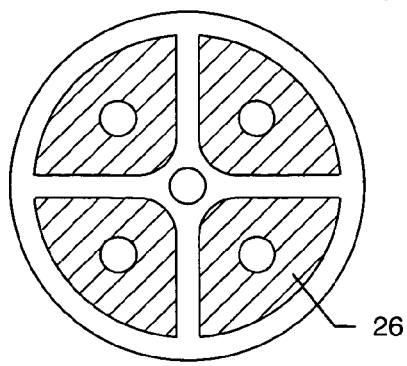
FIG. 49 is a sectional view of the capacitor of FIG. 48 taken generally along line 49—49, illustrating the arrangement of the active electrode plates.
Figure 50:
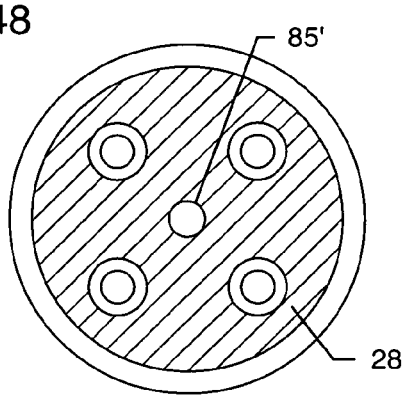
FIG. 50 is a cross-sectional view of the capacitor of FIG. 48 taken generally along line 50—50, showing the configuration of the ground electrode plates.

FIGS. 45 and 46 illustrate the solid ferrite slab inductor 76 which is sandwiched between capacitors 70 and 78 in FIG. 35. Referring to FIG. 46, one can see that a conformal coating 77 has been placed or vacuum deposited over all surfaces of the ferrite inductor slab 76. In a preferred embodiment, this would be done using Paralyne in a vapor deposition process. During original manufacture of the inductor slab 76 it is also desirable that it be tumbled forming radius corners on all edges 79. There are a number of advantages to doing this. One advantage is that by eliminating sharp corners, one reduces stress risers and thereby the potential for breakage or fracturing of the edges of the ferrite material. However, another important reason becomes obvious in conjunction with the present invention. When the conformal coating material 77 is applied by vapor deposition, it forms a more reliable and continuous surface when going around the radius 79 as shown. If the corner 79 was sharp, the conformal coating material 77, on curing, would shrink back away and expose a non-insulated edge at the corner. In an implantable cardioverter defibrillator, the insulation provided by the conformal coating material 77 is quite important.

When the conformal coating material 77 is of Paralyne or equivalent material, the dielectric strength of such material is very high. For example, a two mil or 0.002 inch coating of Paralyne D could provide over two thousand volts of dielectric breakdown strength. This is very important in the output of implantable cardioverter defibrillators where high electric field potentials exist either from the lead wire 18 to the ferrule 12, or between lead wires 18 of opposite polarity. Accordingly, high electric fields can occur across the surfaces of the ferrite inductor 76. The conformal coating material 77 grades these fields and prevents surface arcing. It should also be noted throughout all of the preferred embodiments illustrated, the ferrite slab inductors are preferably conformally coated. This increases the insulation resistance of the ferrite bead and also prevents it from shorting out either to lead wires 18 or to ferrules 12.

FIGS. 47–50 illustrate the top capacitor 78 in FIG. 35. This is a conventional internally grounded capacitor, such as that described by U.S. Pat. No. 5,905,627.

Previously, it was not possible to form a surface-mounted PI circuit filter. However by electrically connecting the two inside diameter metallizations 85 and 85 on the two stacked capacitors together with the connection, shown as 80, 84 or 86, this grounds the electrode plate set 28' of capacitor 78. Therefore, true PI circuit performance is achieved.

Figure 51:
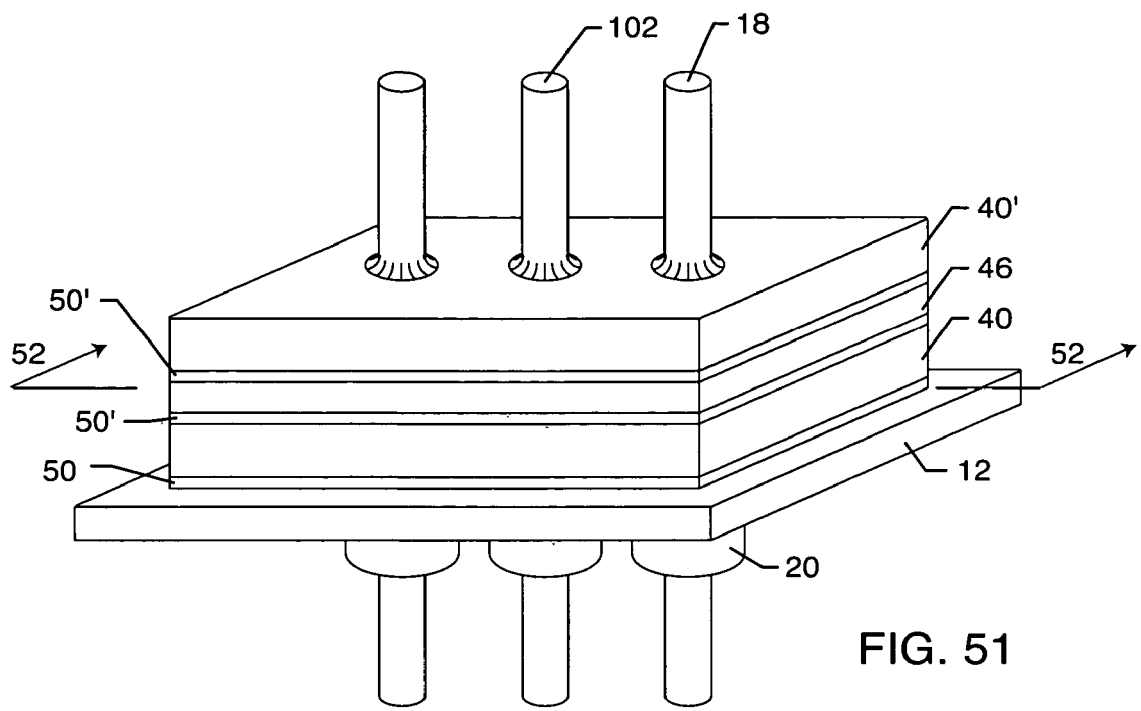
FIG. 51 is a perspective view of an internally grounded three-element PI circuit hermetic terminal embodying the present invention.
Figure 52:
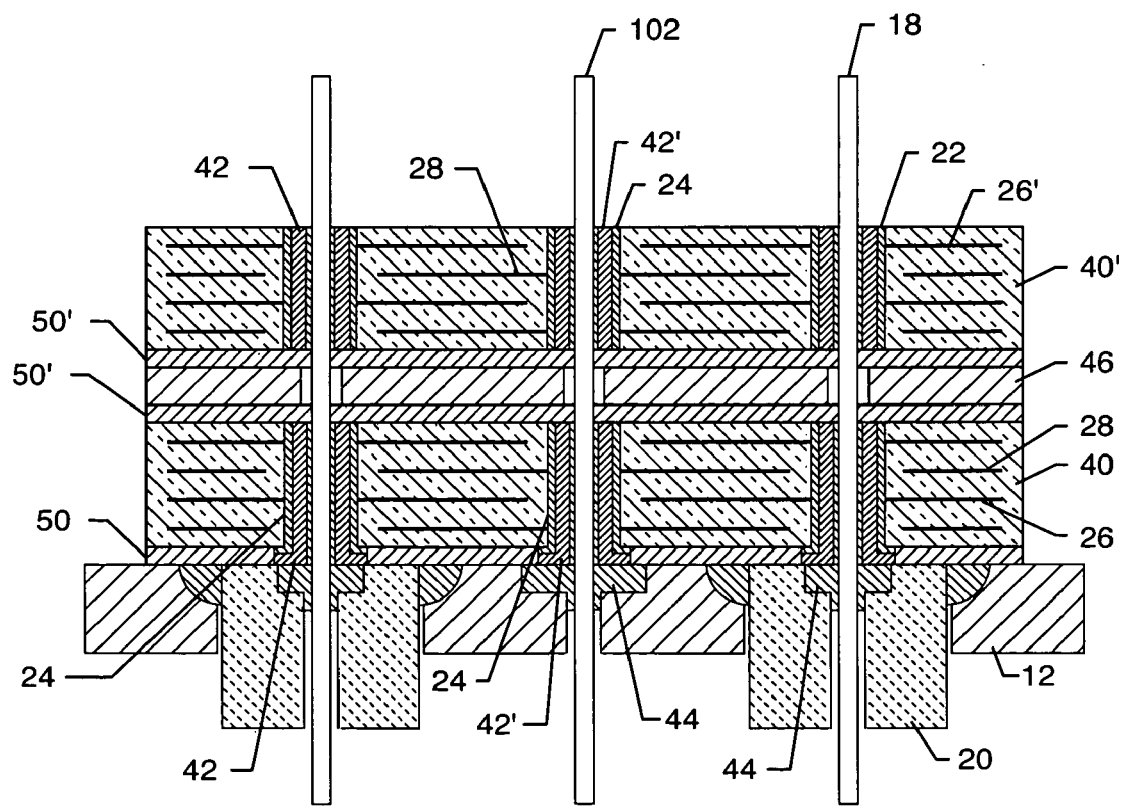
FIG. 52 is a sectional view taken generally along line 52—52 of FIG. 51.

FIGS. 51 and 52 show an internally grounded three element PI circuit configuration of the present invention. A ground lead wire 102 is electrically connected to the ferrule 12 of the hermetic terminal assembly. This is accomplished by gold-brazed material 44. Accordingly, after installation into the housing of an implantable medical device, pin 102 is at ground potential of the housing of the medical device. Lower capacitor 40 is an internally grounded capacitor which is well known in the art (see U.S. Pat. Nos. 5,905,627 and 6,529,103).

A thermal setting conductive polymer or solder 42 and 42' makes electrical connection between the lead wires 18 and 102 and the inside diameter metallization 24 of feedthrough capacitors 40 and 40'. In the case where the pins 102 and 18 are of an oxidized material such as niobium or tantalum an oxide layer builds up and electrically insulates said pins. This oxide layer prevents a reliable electrical connection between the capacitor inside diameter metallization 24 and the pins 102 or 18. However, as shown in FIG. 52, such connection is not required because the conductive material 42 and 42' makes direct contact with gold brazed material 44. This direct connection to gold is described in U.S. patent application Ser. No. 10/377,018.

The grounded pin 102 couples electrically to the internally grounded electrode plates 28 of capacitor 40. Pins 18 are conductively coupled to the active electrode plates 26 of capacitor 40. Both pins 18 and 102 pass through the center holes of the inductor slab 46 in accordance with the present invention. The inductor slab 46 has been previously conformally coated with Paralyne C or D. A non-conductive thermal setting polymer 50' is used to bond the ferrite slab 46 to the lower capacitor 40. A top internally grounded capacitor 40' is then bonded with a second insulating washer 50'. The capacitors 40 and 40' are both internally grounded. Grounded lead wire 102 in turn connects to the ground electrode plates 28' of top capacitor 40'. Lead wires 18 also connect to the active electrode plate set 26' of top capacitor 40'. It should be noted that it is not necessary that the capacitance value of capacitor 40 and 40' be of the same value. For example, capacitor 40 could be a 4000 picofarad capacitor and capacitor 40' could be a 900 picofarad capacitor. By staggering the capacitance values, one can make adjustments to the resonance of the PI circuit below its 3 dB cut-off point. This can be important so that gain does not occur at low frequencies in the low pass filter function.

Figure 53:
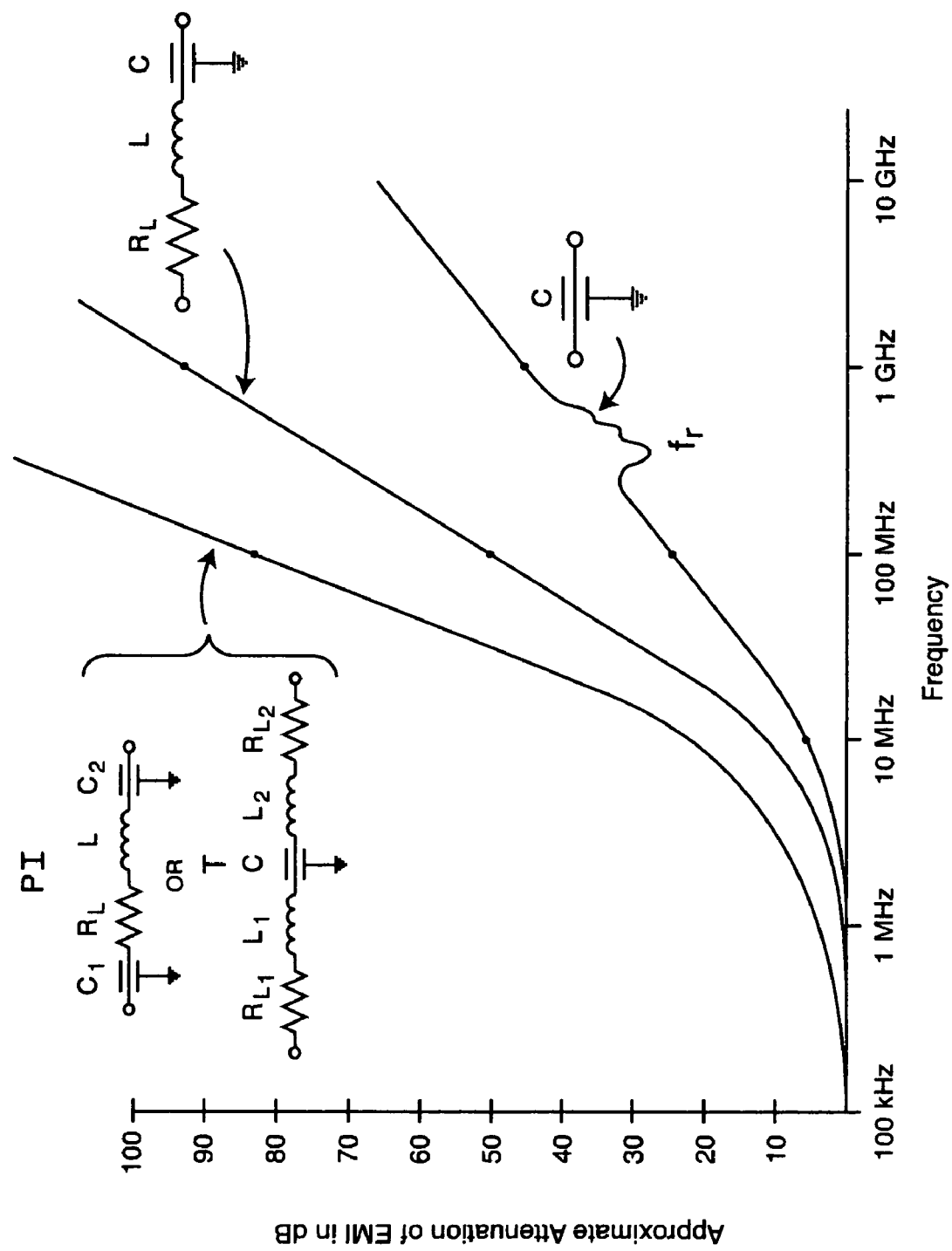
FIG. 53 is a family of performance curves illustrating the advantages of adding the inductor filter elements of the present invention.

With reference now to FIG. 53, more accurate (in comparison to the generic curves shown in FIG. 10) EMI filter performance (attenuation) curves versus frequency graphs illustrate the advantages of adding filter elements. As can be seen, there is substantial difference between the single element (feedthrough capacitor or C), the L circuit and the PI circuit configurations. One will notice that the curves become non-linear at lower frequency. Accordingly, if the PI circuit filter is properly designed (so that it does not resonate) it can offer substantially higher attenuation at lower frequencies. As previously mentioned, the slope of the PI circuit is 60 dB per decade. The slope of the L circuit is 40 dB per decade, and the slope of the C circuit is 20 dB per decade.

In FIG. 53, one can see a resonant dip $f_r$ in the performance curve of the single element C-section filter. This self-resonance phenomenon is typical of all feedthrough capacitors. Feedthrough capacitor devices resonate far differently than standard monolithic ceramic chip capacitors (MLCCs). In an MLCC, the resonance is caused by parasitic inductance, which in the equivalent circuit, is in series with the capacitor. For an MLCC at resonance, the attenuation actually increases dramatically. However, above resonance the attenuation rapidly falls off as the MLCC capacitor becomes increasingly inductive. The opposite tends to happen in a feedthrough capacitor as illustrated in FIG. 53. This is a more complicated type of parallel transmission line resonance. The feedthrough capacitor continues to function above its self-resonant frequency and is still an effective EMI filter. However, as one can see from the single element C-filter graph of FIG. 53, there is a drop in attenuation at the actual resonant frequency $f_r$. This is undesirable, particularly if the drop in attenuation occurs at the frequency of an EMI emitter such as a cellular telephone. This means that at that particular frequency $f_r$, the implantable medical device, like a cardiac pacemaker, is more susceptible to outside interference. The addition of the inductor slab element as described herein not only increases the attenuation slope as shown in FIG. 53, but also minimizes or eliminates the resonant dip phenomenon $f_r$ as previously described. The inductor slab, therefore, compensates for problems associated with the self-resonance characteristic of the feedthrough capacitor.

As previously described for an L section filter, it is desirable to have the inductor element point towards the AIMD input circuits. For similar reasons, it is desirable to have a PI section filter as illustrated in FIG. 35, as opposed to a T section filter. This has to do with the novel impedances that are present in an implanted medical device. In general, lead wires that are implanted within the human body are electrically dampened by the surrounding body tissue. Additionally body tissue also acts to reflect and absorb high frequency EMI signals. Because of this, the source impedance of implanted lead wires tends to be stable and approximate 80 ohms. Adding additional resistance or inductance in series with this resistance does not do much to improve the attenuation of an EMI filter. Accordingly, the PI circuit or L section configurations as described are preferred.

Figure 54:
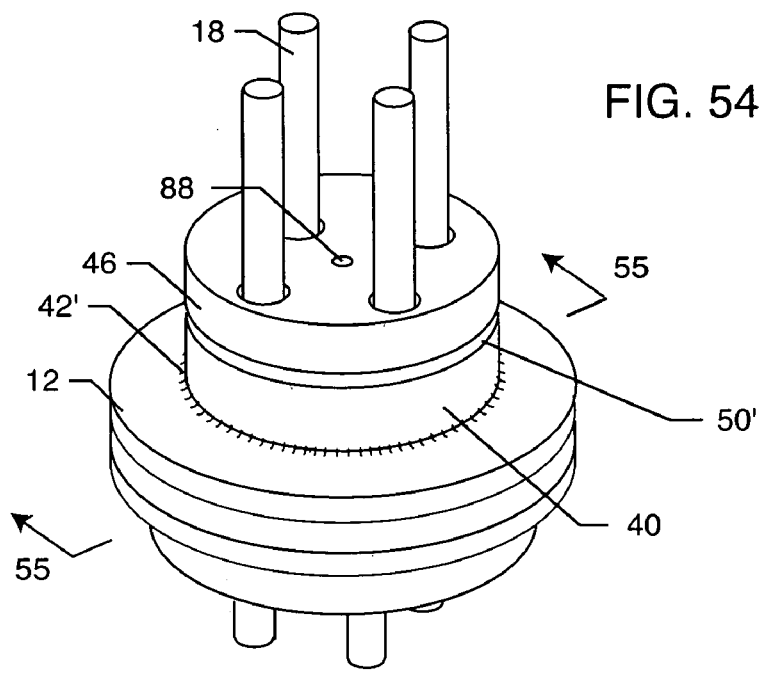
FIG. 54 is a perspective view illustrating an alternative embodiment of a ceramic capacitor and inductor mounted to a hermetic terminal and having a center hole therethrough, which allows for ready passage of a gas during hermetic seal testing.

Another novel aspect of the ferrite slab inductor is the ability to combine it with helium leak detection vent holes, as described in U.S. Pat. No. 6,566,978 (the contents of which are incorporated by reference herein). FIG. 54 illustrates a novel ferrite slab quad-polar inductor 46 with a small hole 88 in the center which is designed to line up with a small centered hole 90 (not shown) in the ceramic feedthrough capacitor 40. As described in U.S. Pat. No. 6,566,978 (the contents of which are incorporated herein), a defective gold braze 44 or 44' or defective hermetic seal 20 could be readily detected by the centered through-hole passage whereby helium leak gas could freely flow. A ferrite slab inductor 46 can be bonded using a polyimide matrix washer 50' directly to the ceramic capacitor 40. In this case, the inductor 46 has been specially modified so that it has a center hole 88 which lines up with the helium vent hole 90 of the capacitor 40. The center hole 88 in the ferrite slab 46 can be manufactured during initial pressing or by drilling before or after sintering. If the hole in the center of the ferrite slab 46 is very small it can also be added by laser or water cutting techniques.

Figure 55:
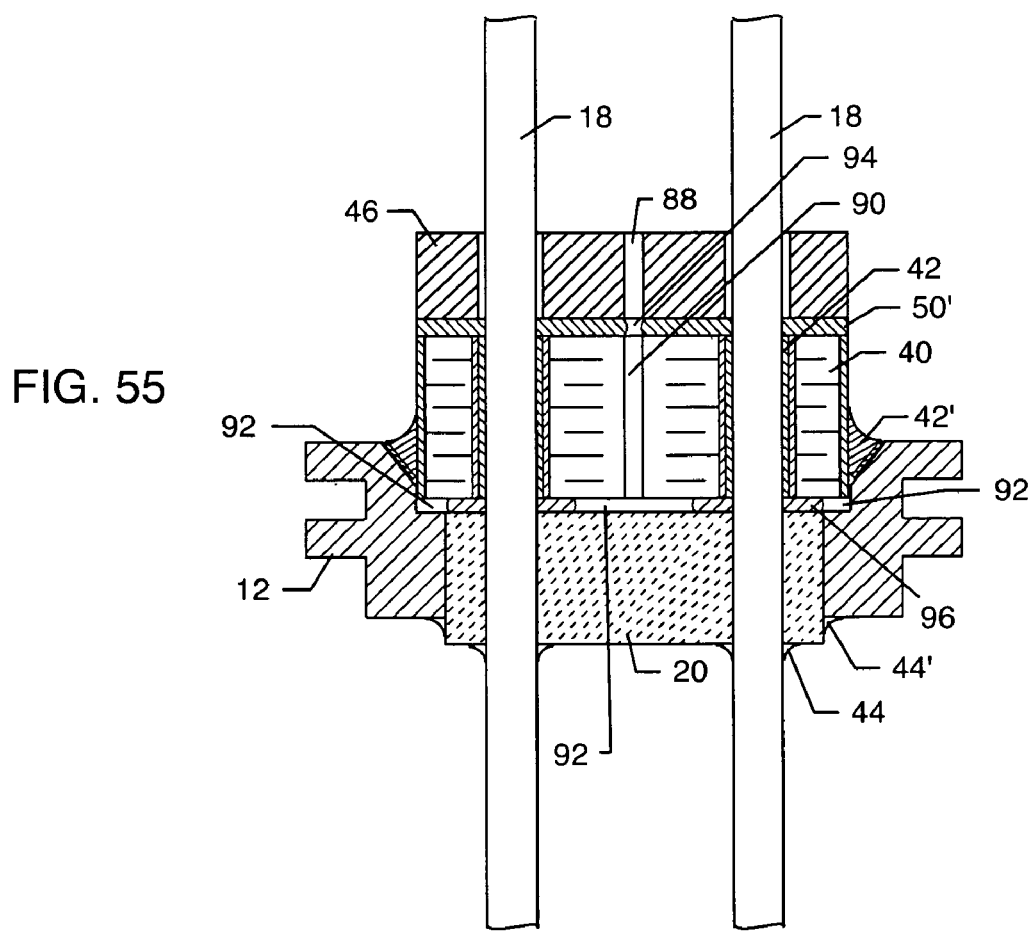
FIG. 55 is a cross-sectional view of the assembly of FIG. 54 taken generally along line 55—55, showing the inductor bonded to the capacitor with the aligned center hole for helium leak detection.

FIG. 55 illustrates a cross-section of this assembly showing an air gap 92 between the ceramic capacitor 40 and the insulative hermetic seal 20. The air gap 92 facilitates detection of a defective hermetic seal 20 or defective braze 44 or 44'. For example, in a typical implantable medical device hermetic feedthrough terminal assembly, seal 44 or 44' would be a gold braze which is attached to a sputtered surface of the alumina insulator 20. In the case where there is a pinhole or defect in such gold braze 44 or 44', body fluid could penetrate. In the case where body fluid penetrates to the inside of the implantable medical device, catastrophic failure is usually the result. The electronic components that are inside of an implantable medical device, such as a cardiac pacemaker and the like, typically consist of sensitive electronic circuits including hybrid chips and other components. Even a slight amount of moisture can cause the insulation resistance to degrade on such components which can either lead to immediate catastrophic failure or premature battery failure of the device. Accordingly, it is very important that hermetic seal testing, including helium leak testing detect any such defect. In this regard, it has been shown that installation of the feedthrough capacitor 40 along with its surrounding electrical connection and bonding materials 42 and 42' can mask, for a period of time, a defective gold braze 44 or 44'. Helium leak testing as presently done in the industry is effected very rapidly. There is typically not sufficient time for penetration of helium through bulk polymers. Thus, it is highly desirable to provide such passage holes through the center of the feedthrough capacitor that are described in U.S. Pat. No. 6,566,978.

A novel feature of the L-circuit filter of the present invention as shown in FIGS. 54 and 55 is that the co-bonded ferrite slab 46 also has a corresponding leak detection vent hole 88 which lines up with the vent hole 90 in the ceramic capacitor 40. Accordingly, the laminating washer 50' also has a corresponding hole 94 which aligns with the previously mentioned vent holes 88 and 90. This provides a convenient space for helium to escape from the entrapped air spaces 92 underneath the capacitor 40 and be readily detected during a helium leak test through vent holes 90, 94 and 88.

There is a small round insulative washer 96 placed around each leadwire 18 before the capacitor 40 is inserted into and seated against the bottom of the ferrule 12. These insulating washers 96 prevent the conductive material 42 that is used to connect the capacitor leadwire 18 to the capacitor 40 inside diameter termination, from penetrating into the air gap 92. It would be undesirable to have conductive materials floating around in this air gap 92 as this could lead to short circuits or a decrease in the insulation resistance of the device.

Figure 56:
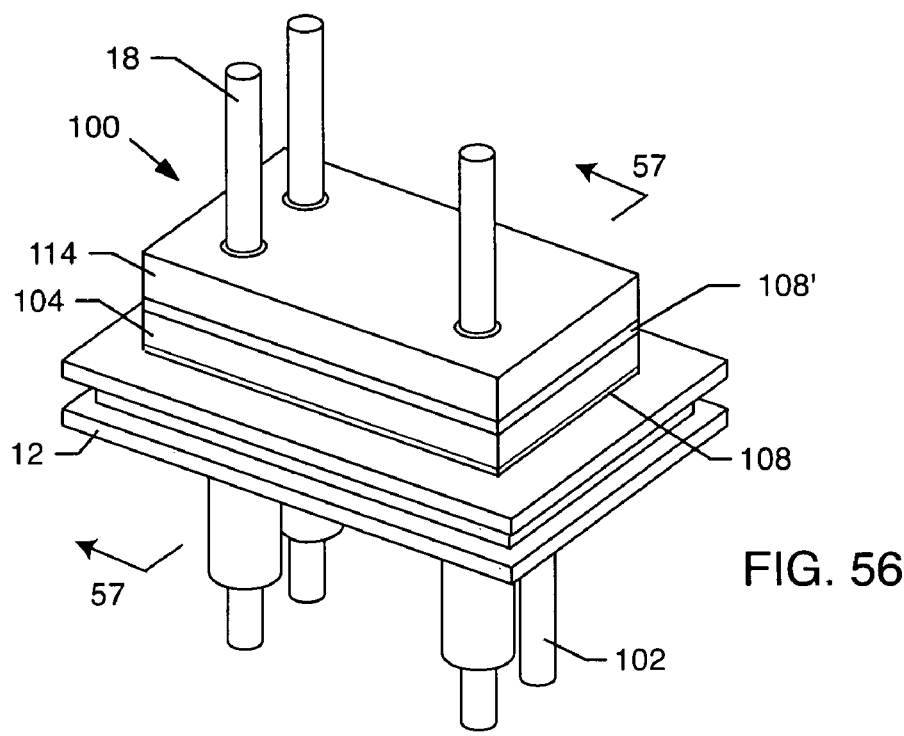
FIG. 56 illustrates an internally grounded tri-polar capacitor.
Figure 57:
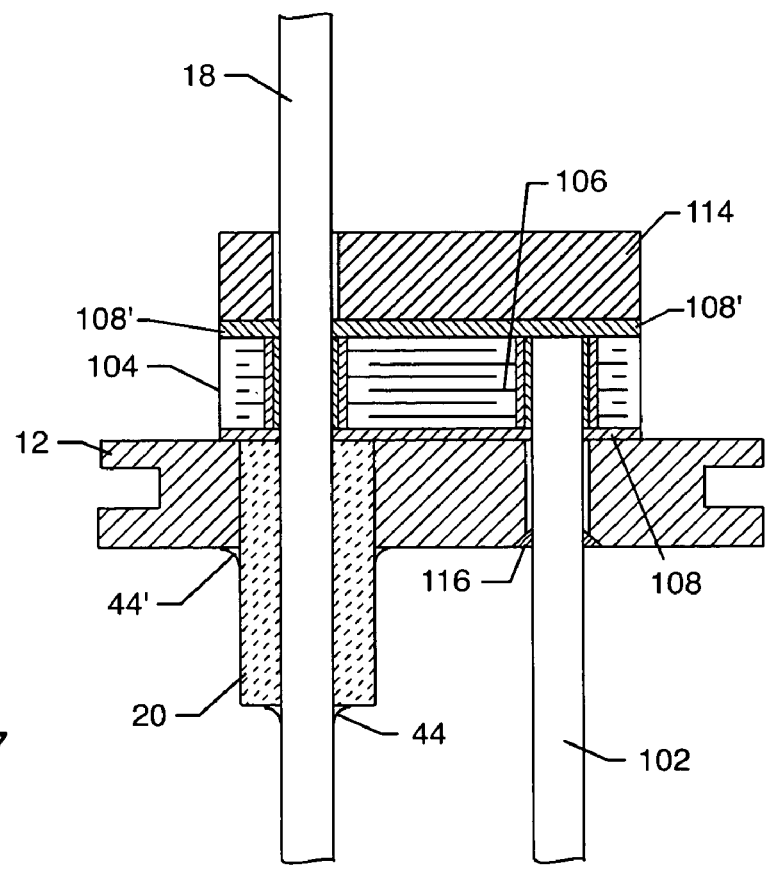
FIG. 57 is a cross-sectional view taken generally along line 57—57 of FIG. 56.

With reference to FIGS. 56 and 57, an internally grounded tri-polar capacitor assembly 100 embodying the present invention is illustrated. In this case, an internal ground lead 102 is not required on the inside of the implantable medical device. Accordingly, the internal ground lead 102 needs to penetrate into the inside of the implantable medical device for a distance no greater than the thickness of the ceramic capacitor 104. As shown in FIG. 57, the lead wire 102 grounds the ground electrode plate set 106. The internally grounded tri-polar feedthrough capacitor 104 is seated onto the hermetic ferrule 12 and onto an insulating washer 108. In this case the inductor slab 114 only has three holes. This provides inductance on the three active leadwires 18 that go to the interior of the implantable medical device. It should be noted that there is no point in doing additional filtering on a pin 102 that is already grounded. The grounded pin 102 is by definition shorted to the ferrule 12 which provides infinite attenuation. The grounded pin 102 is typically conductively coupled to the ferrule 12 by gold brazing 116 or the like. Further methods of attaching the ground pin 102 are resistance welding, laser welding, and the like.

Figure 60:
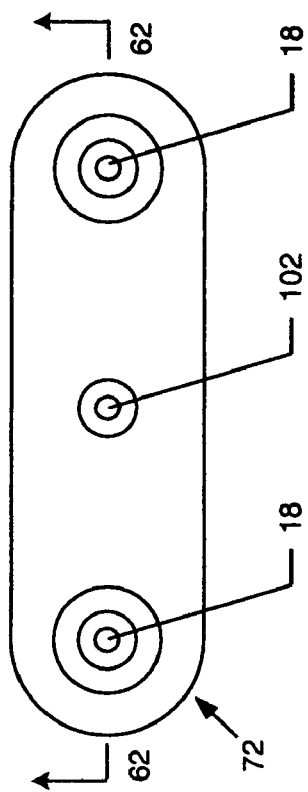
FIG. 60 is a schematic diagram of the EMI filter assembly of FIGS. 58 and 59.

It is also possible to use discrete ferrite beads as opposed to a single ferrite slab inductor. FIGS. 58–60 illustrate an inline multi-polar hermetic terminal assembly 118 suitable for human implant such as in a cochlear hearing device. This unit is ideally designed for discrete uni-polar ceramic capacitors 40. FIG. 59 is a cross-section of this device with multiple uni-polar capacitors 40 to which multiple uni-polar ferrite inductors 46 have been co-bonded in accordance with the present invention, such as by washer 50'. FIG. 60 is the schematic drawing of the device shown in FIGS. 58 and 59, illustrating two parallel L section filters. The schematic of FIG. 60 is shown conveniently as a bipolar or two section filter. In fact, in modern implantable pacemakers, a new therapy known as biventricular pacing has become very popular. In addition, cochlear implants typically incorporate fourteen to sixteen lead wires. Accordingly, additional lead wires 18 are required. It is now common to see hermetic terminal assemblies with anywhere from four to sixteen lead wires. In this particular embodiment there are two discreet uni-polar feedthrough capacitors 40 bonded between the pin 18 and the titanium ferrule 12. Also shown is a ferrite bead 46 of sandwich construction as previously described, added to each one of the active leads.

It will be obvious to those skilled in the art that the inline bipolar feedthrough capacitor as shown in FIGS. 58 and 59 can be elongated to add additional filtered lead wires 18. Dual in-line configurations are also convenient.

Figure 61:
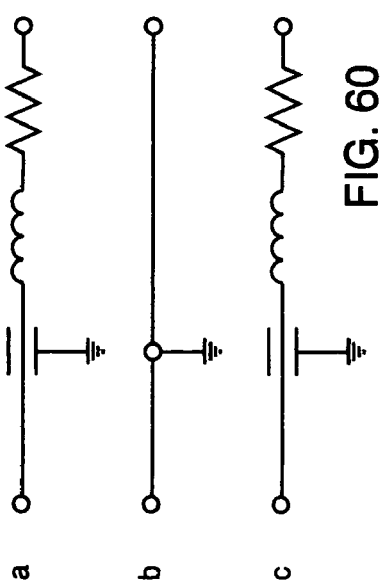
FIG. 61 is a top plan view of a multi-polar EMI filter with a grounded pin, similar to FIG. 58.
Figure 62:
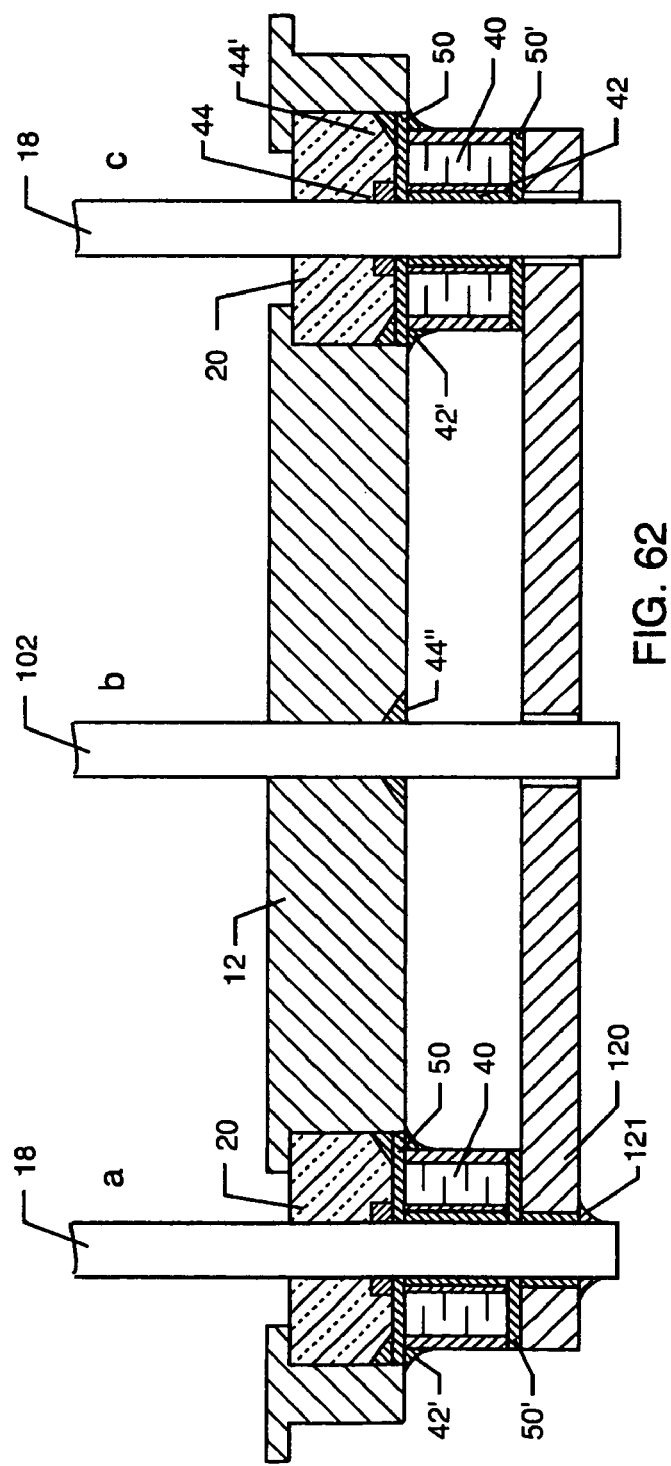
FIG. 62 is a cross-sectional view taken generally along line 62—62 of FIG. 61, illustrating the use of an inductor slab instead of individual inductor beads.
Figure 63:
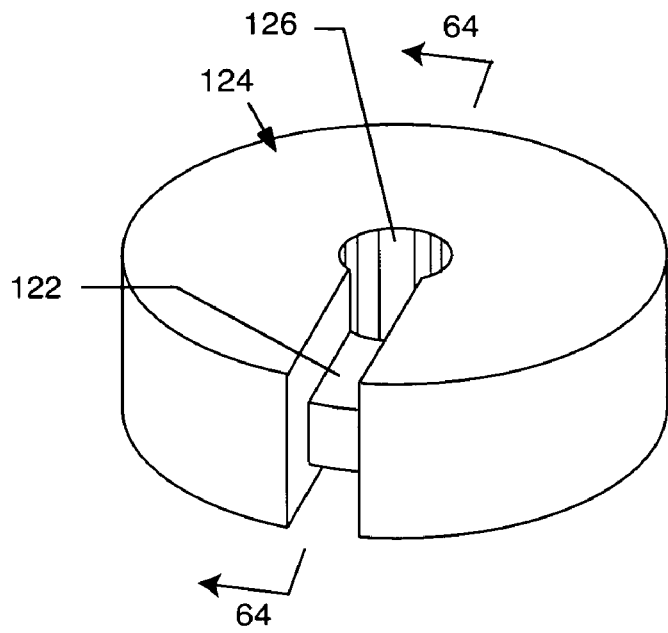
FIG. 63 is a perspective view of a novel inductor having a notch in accordance with a preferred embodiment of the present invention.

FIGS. 61 and 62 illustrate the same device shown in FIGS. 58 and 59, except that instead of discrete ferrite bead elements, a ferrite slab 120 has been bonded to the uni-polar capacitors 40. In this case, instead of using individual ferrite beads 46, a ferrite slab 120 is employed which slips over and bonds to all of the capacitors 40 at one time. Referring to FIG. 62, one can see that there is an epoxy preform 121 shown and disposed between a lead wire 18 and the inductor slab 120. This optional epoxy preform can be placed around each lead wire to improve the cosmetic appearance and also mechanically strengthen the assembly. Another reason to have an optional epoxy or polyimide preform 121 is to improve the high voltage characteristics of a device, such as an implantable cardioverter defibrillator.

As previously mentioned, the amount of inductance that one achieves is very important to achieve overall attenuation. This is different than the attenuation slope measured in dB per decade. As one increases the capacitance and the inductance, the starting point (3 db point) goes down in frequency and the overall attenuation increases dramatically. As an example, if one had a very low value of capacitance and a very low value of inductance, one might only have 5 dB at 100 MHz. Even though one had a two-element filter, which increases at 40 dB per decade, one would in this case be limited to only 45 dB at 1000 MHz (a decade higher than 100 MHz). However, if one was able to increase the capacitance value and increase the inductance value, one might have a starting attenuation at 100 MHz of 20 dB. This would mean that at 1000 MHz, one would have 60 dB of attenuation, which is very substantial indeed. Accordingly, there is a need for as much inductance as possible in the ferrite or ferrite slab element. As previously mentioned, it is not possible to wind multiple turns around a conventional ferrite slab or ferrite bead once it has been co-bonded or mounted to a ceramic capacitor and the hermetic terminal of a human implantable medical device.

Figure 67:
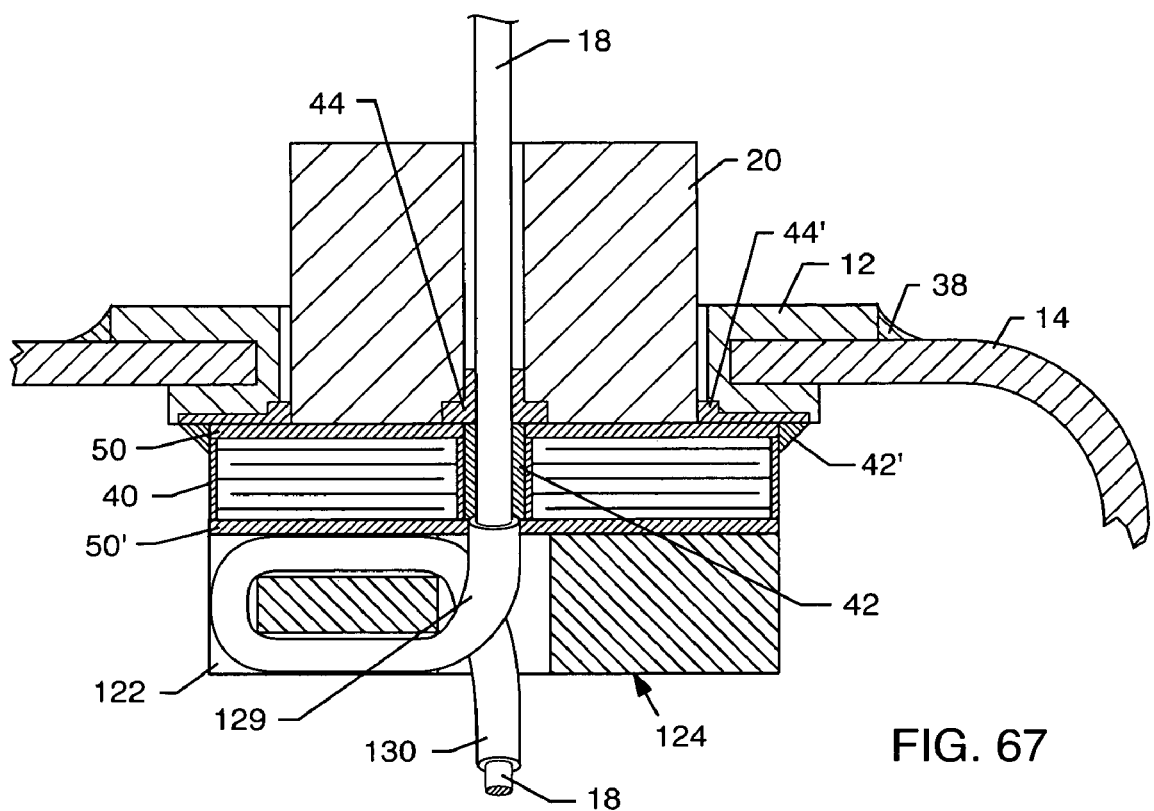
FIG. 67 is a sectional view similar to FIG. 17, but employing the novel ferrite bead of FIG. 63.
Figure 68:
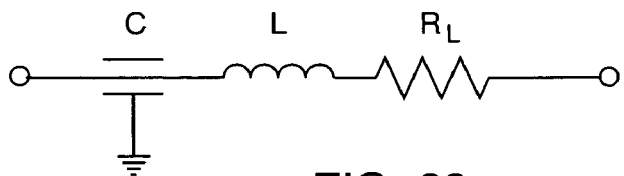
FIG. 68 illustrates the schematic diagram of the EMI filtered terminal assembly of FIG. 67.

FIGS. 63–66 illustrate a preferred embodiment of the present invention wherein a novel pressed indentation or notch 122 has been formed during the powder pressing or subsequent machining of the ferrite bead and then sintered into a solid, monolithic inductor structure 124. Ferrite beads are generally made of proprietary powders, which are put into multi-stage toggle presses. This pelletizing process (with binders) forms the ferrite element which is then sintered at very high temperatures making it into a hard monolithic structure. It is a simple matter of mold tooling to form the notch 122 illustrated in FIGS. 63 and 64. As can be seen in FIG. 67, this makes it possible to bond the ferrite slab 124 directly to the ceramic capacitor 40 placing it over a single lead wire 18. It is then relatively easy to pass the lead wire 18 back around through and up through the center hole 126 of the ferrite slab 124 thereby adding another turn. In this case, we have described a two-turn inductor which increases the inductance by a factor of four ($2^2$).

Figure 64:
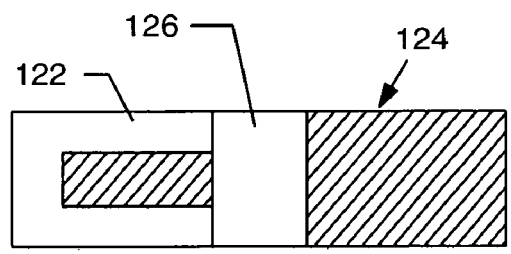
FIG. 64 is a cross-sectional view taken generally along the line 64—64 of FIG. 63.
Figure 65:
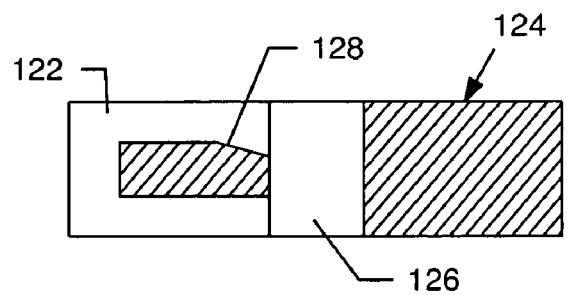
FIG. 65 is a view similar to FIG. 64, incorporating a ramp for facilitating feed of a multiple turn lead wire through the center hole of the ferrite inductor.
Figure 66:
FIG. 66 is an electrical schematic drawing of the ferrite bead of FIG. 63.

FIG. 65 illustrates an improved embodiment of the novel ferrite slab inductor 124 shown in FIG. 64 incorporating a ramp 128 upward thereby making it easier to feed the lead wire 18 back around and up through the center hole 126 of the ferrite inductor 124. It is very important that a notch 122 not be cut all the way through which would form an air gap in the circular toroid 124. It is very important for a toroidal inductor that it contains and form a very low reluctance path for magnetic fields. Field inductance in this case will still occur throughout the toroid wherein the magnetic field is constrained within the toroidal inductor 124. By eliminating the air gap, we can provide a very high amount of inductance in a very efficient manner.

A unique aspect of all implantable medical device hermetic terminals is that the lead 18 is pre-manufactured to form a hermetic seal. In certain hermetic terminals, the lead 18 is attached to the alumina insulator 20 by gold brazing 44. In turn, the alumina insulator 20 is gold brazed 44 to a titanium ferrule 12. In applications other than implantable medical device hermetic terminals, it is easy to manufacture multi-turn inductors because a loose lead wire is available for one or more turns around a toroidal inductor. However, in the case of an implantable medical device, a major problem arises in how to bond the ferrite directly to the capacitor and then to make a multiple turn. The novel molded notch feature, illustrated in FIG. 63, demonstrates a methodology in which the capacitor 40 can be placed down over the lead wire 18 which is straight and then the lead wire 18 can be looped back through and around the notch 122 and brought out through the top yielding a two turn toroidal inductor as shown in FIG. 67. As previously mentioned, the inductance is directly related to the square of the number of turns. The inductor 124 shown in FIG. 67 is known in the art as a two-turn inductor. By squaring the number two, this means that this would have four times the amount of inductance as simply passing a lead wire 18 directly through the center 126.

It should be pointed out that the lead wires that are typically used in implantable medical devices must be of suitable biocompatible materials. Typical lead wires are platinum, platinum-iridium, tantalum, niobium and the like. As these lead wires 18 form multiple turns through the center of a ferrite 124, as illustrated in FIG. 67, it is very important that the turns do not touch one another. If for example, in FIG. 67 where the lead wire 18 loops around and crosses past itself in area 129 physically touched together, then this shorted turn would once again become a single turn inductor. This would not affect the inherent operation of the pacemaker, however, it would result in reduced EMI filter attenuation.

Figure 69:
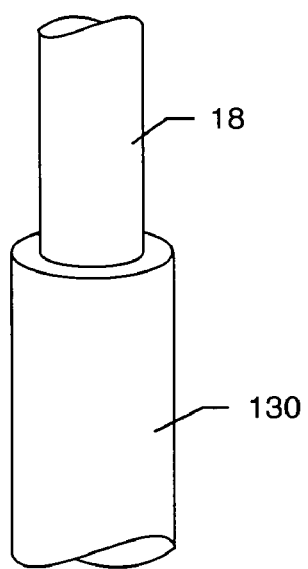
FIG. 69 is an enlarged fragmented perspective view of a portion of the terminal lead shown in FIG. 67, illustrating that a portion of an insulator is removed from the lead as it extends upwardly through the capacitor.

Accordingly, there is a need to insulate the turns where they pass each other through the center 129 of the ferrite inductor 124. The present invention describes a number of ways of doing this. One way would be to slip on an insulating sleeve 130 as shown in FIG. 67 and shown expanded in FIG. 69. Suitable insulating sleeves 130 can be made of Teflon, Kapton, or the like and are very thin. They also have excellent dielectric strength characteristics and can be easily slipped over the wire 18. Other methods would include conformal coating of the wire 18 with a thin insulating material. It should be noted that there is very little voltage difference between the adjacent turns of the wire 18 passing through a ferrite or iron core inductor 124. Therefore, not very much insulation or dielectric withstanding voltage requirement is necessary. Accordingly, a very thin coating of Paralyne, polyimide, epoxy or other insulating material is all that is really required. Another methodology would be to carefully place the turns through the center of ferrite inductor 124 and then subsequently add an encapsulant or sealant such that the un-insulated wire shorted.

Figure 70:
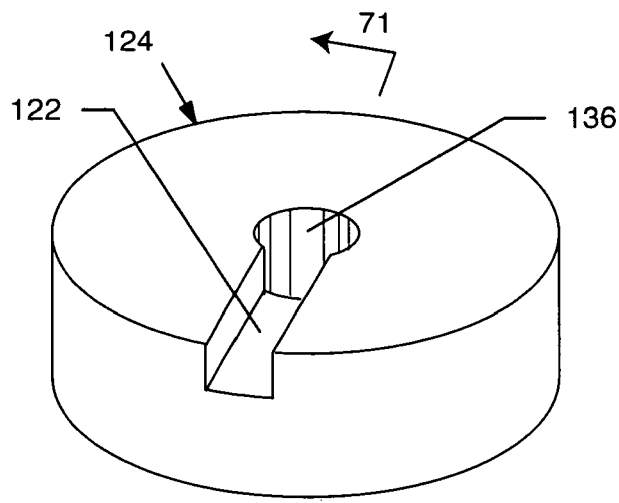
FIG. 70 is a perspective view of a uni-polar ferrite slab designed with a novel slot arrangement.
Figure 71:
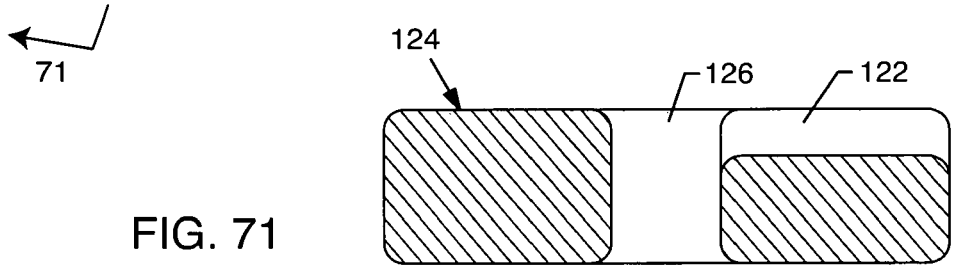
FIG. 71 is a cross-sectional view taken generally along the line 71—71 of FIG. 70.
Figure 72:
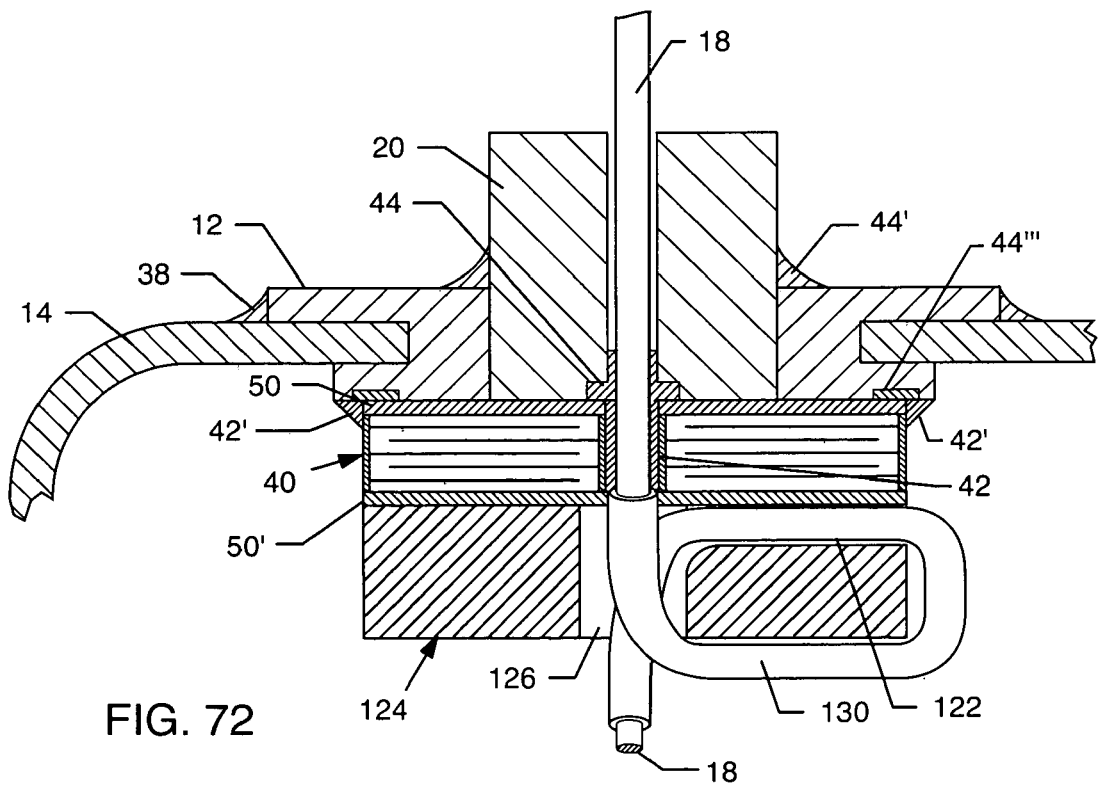
FIG. 72 is a cross-sectional view illustrating a uni-polar feedthrough capacitor utilizing the ferrite slab of FIG. 70.

With reference now to FIGS. 70–72, yet another inductor 124 is illustrated having a notch 122 formed therein which is different in configuration than that illustrated and described above. As illustrated in FIG. 72, the ferrite slab inductor 124 is co-bonded to the capacitor 40, such as by washer 50 similar to that illustrated in FIG. 67, but the lead wire 18 is brought through the center 126 of the inductor 124 and then wrapped back around through the convenience notch 122 and back through the center hole 126 of the inductor 124, therefore, forming a two-turn inductor.

As previously noted a two-turn inductor has four times the amount of inductance as a single turn inductor. The difference between this particular ferrite slab 124 and the one shown in FIG. 67, is the notch 122 is only on one side of the ferrite inductor 124. This has the effect of putting the leadwire 18 across the top of the inductor 124. In some applications, where there is sufficient room inside the pacemaker, this would be desirable. However, in the preferred embodiment shown in FIG. 67, one would not have this leadwire 18 coming across the top of the inductor 124. The choice is whether to use the configuration in FIG. 63, with a slot on top and bottom, as compared to the single slot 122 shown in FIGS. 70 and 71. There is little performance difference in terms of attenuation in these two approaches.

Figure 73:
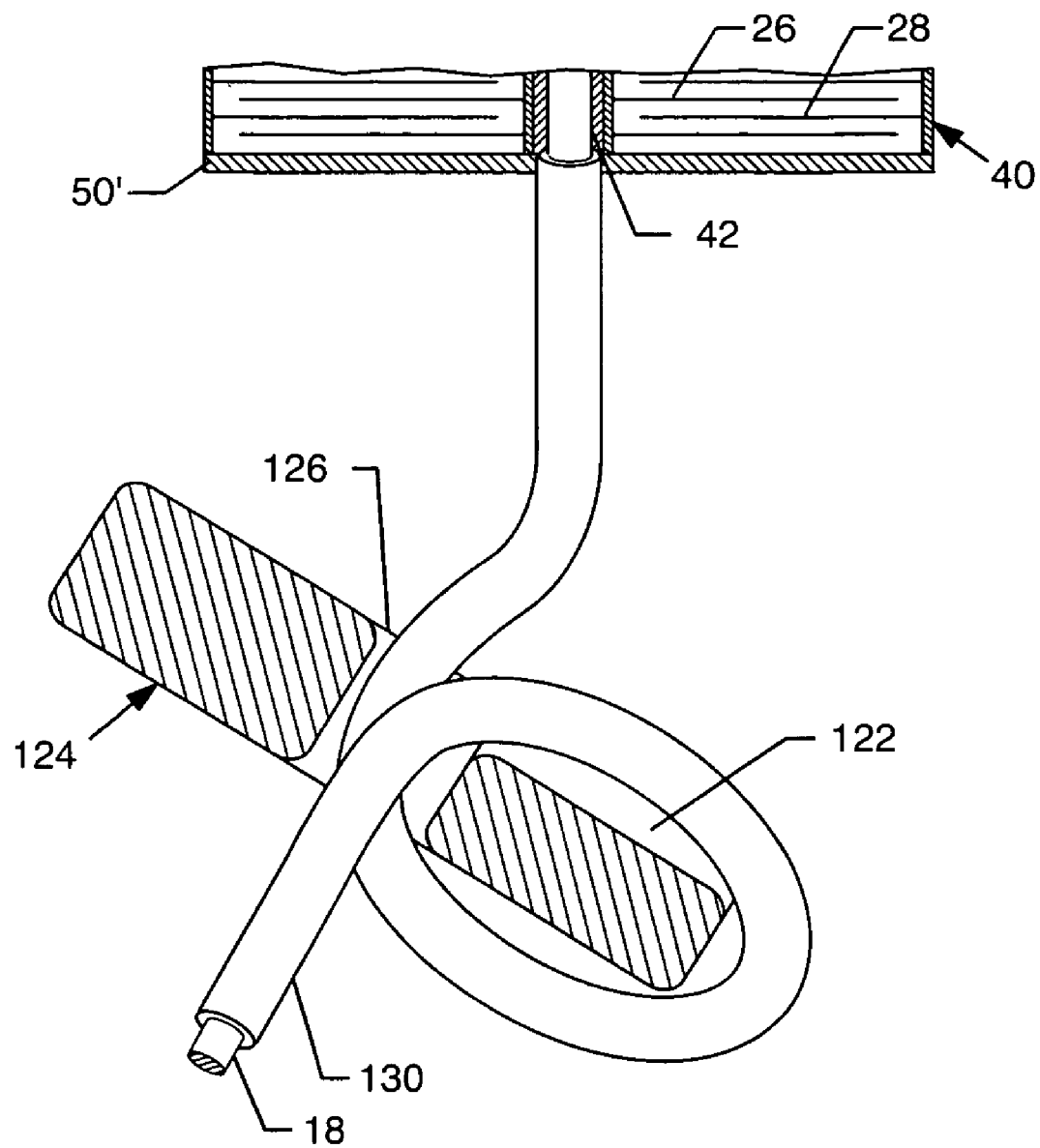
FIG. 73 is a fragmented perspective view of a novel two-turn uni-polar inductor embodying the present invention.

FIG. 73 illustrates an alternative method of manufacturing the two-turn L section EMI filter previously illustrated in FIG. 72. In FIG. 73, a long lead wire 18 is elongated through the feedthrough capacitor 40. An insulative tubing 130 is placed over the lead wire 18. It is desirable that insulative tubing 130 has a very low coefficient of friction. Such materials would be Teflon, Kapton or the like. A turn would be looped through the center and back around through the ferrite slab 124, as shown. It is desirable that ferrite slab 124 have rounded corners to facilitate slipping the ferrite slab down along the tubing to seat it on top of the ceramic capacitor by way of insulating bonding material 50'. Once the loose loop is formed, one can simply grasp the end of the lead wire 18 and push downward on the ferrite slab 124, so that it slips along until it seats against the top of the capacitor 40 and its bonding washer 50'. The lead wire 18 can then be snugged up so that it fits within the notch space 122. It is desirable that the insulating tubing 130 be captured and cured into the inside diameter hole of the polyimide insulating washer 50'. A non-conductive polymer is preferred.

Figure 74:
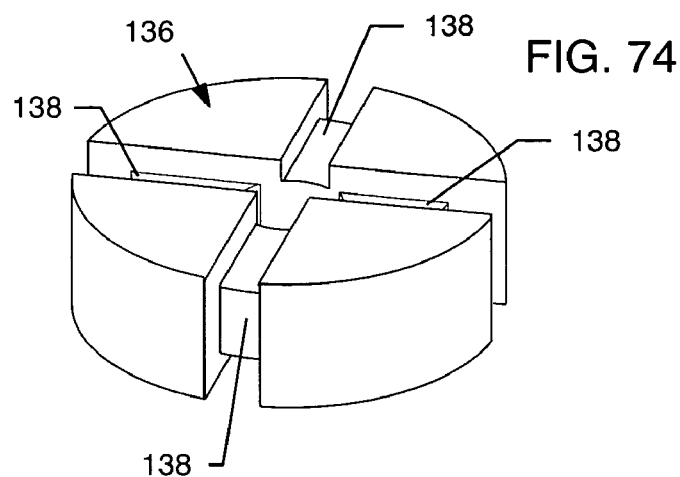
FIG. 74 is a perspective view of a uni-polar ferrite slab with four slots.
Figure 75:
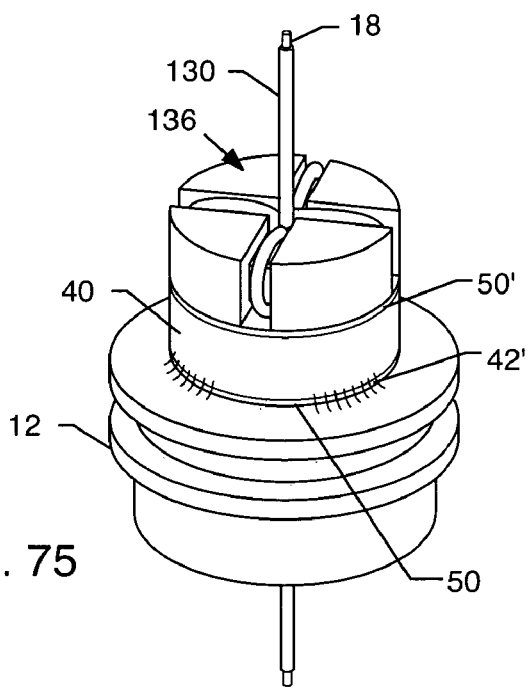
FIG. 75 is a perspective view illustrating the novel four-turn uni-polar ferrite of FIG. 74 mounted to a hermetic terminal and assembled.

It is also possible to add additional turns. FIG. 74 illustrates a novel uni-polar ferrite slab inductor 136 with four novel slots 138. Accordingly, in this design, one could place four additional turns for a total of five turns through the inductor slab 136. If we square the number of five this means that we would have twenty five times the inductance of a straight lead wire ferrite. FIG. 75 illustrates the novel five-turn inductor 136 of FIG. 74 mounted to the hermetic terminal 12 of an implantable medical device.

Figure 76:
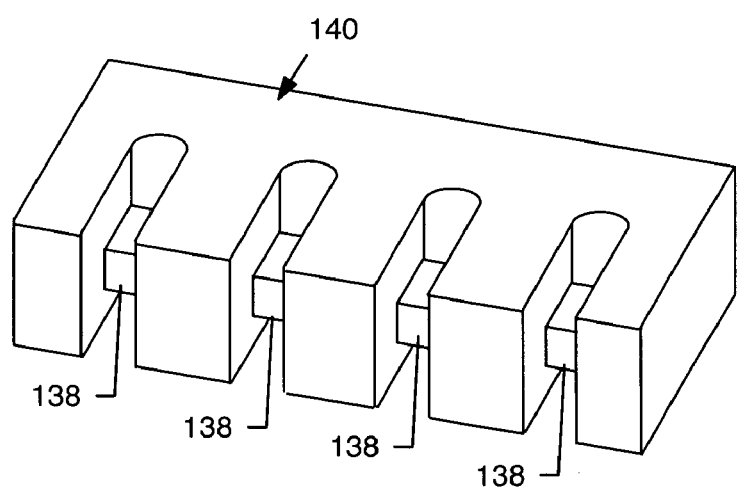
FIG. 76 is a perspective view of an inline quad-polar ferrite bead having four slots in accordance with the present invention.

FIG. 76 illustrates a rectangular quad-polar ferrite slab 140 incorporating the features of the present invention. This allows each of the four individual EMI filters to have a two turn toroid, which will greatly increase the inductance by a factor of four (2 turns squared). FIG. 77 illustrates the mounting of the novel quad-polar ferrite slab inductor 140 to a quad-polar ceramic feedthrough capacitor filter 144 employing a novel gold bond pad 146. In this case, the inline quad-polar feedthrough capacitor 144 has metallized ground stripes 148 on each side which are attached to a gold brazed bond pad area 146, as described in pending U.S. patent application Ser. No. 10/377,086, filed Feb. 27, 2003.

FIG. 78 is the schematic diagram of the quad-polar L section capacitor that is illustrated in FIG. 76.

With reference now to FIG. 79, another quad-polar ferrite slab inductor 150 is illustrated having notches 152 adapted to permit a terminal pin or leadwire 18 to extend therethrough. However, in this case, each notch 152 includes dividers 154 and 154' which create multiple slots within the notch 152 such that the leadwire or terminal pin 18 can be extended through with multiple turns through each notch 152. Thus, these novel slots 152 allow a second turn to be brought around and through the bonded ferrite slab inductor 150 without shorting the adjacent turns.

Figure 80:
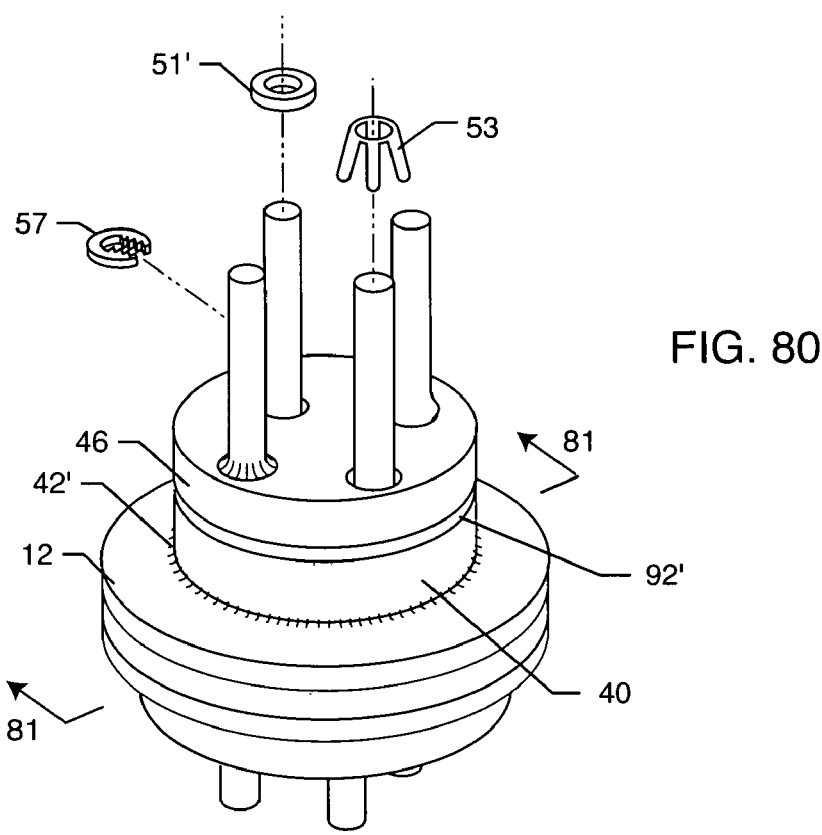
FIG. 80 is a perspective view of a quad-polar feedthrough filter terminal assembly wherein the inductor slab is loosely seated on top of the capacitor without any bonding material.
Figure 82:
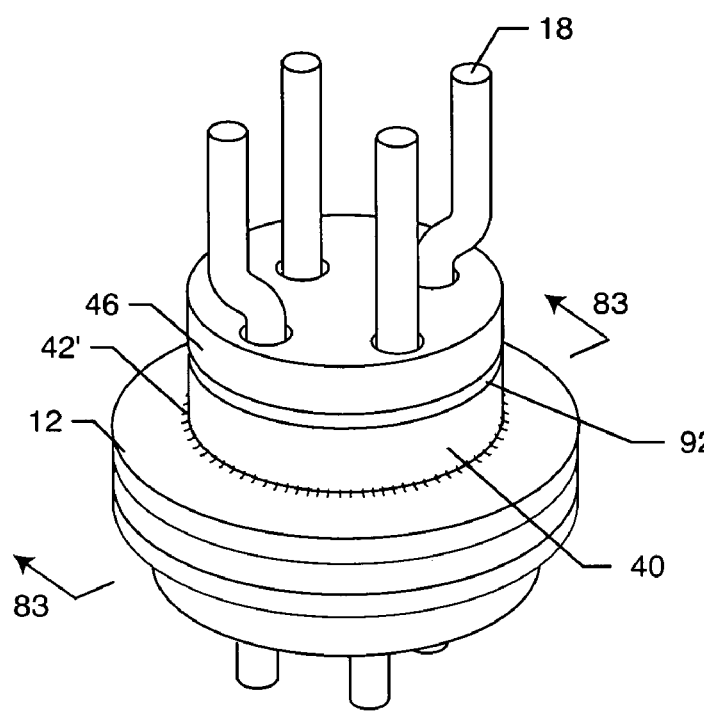
FIG. 82 is a perspective view of a quad-polar feedthrough filter terminal assembly similar to that illustrated in FIGS. 80 and 81, illustrating another embodiment thereof.

The structure of FIGS. 80 and 82 are very similar to those previously described in FIGS. 54 and 55. The capacitor 40 incorporates a leak detection vent hole 90 as previously described.

Figure 81:
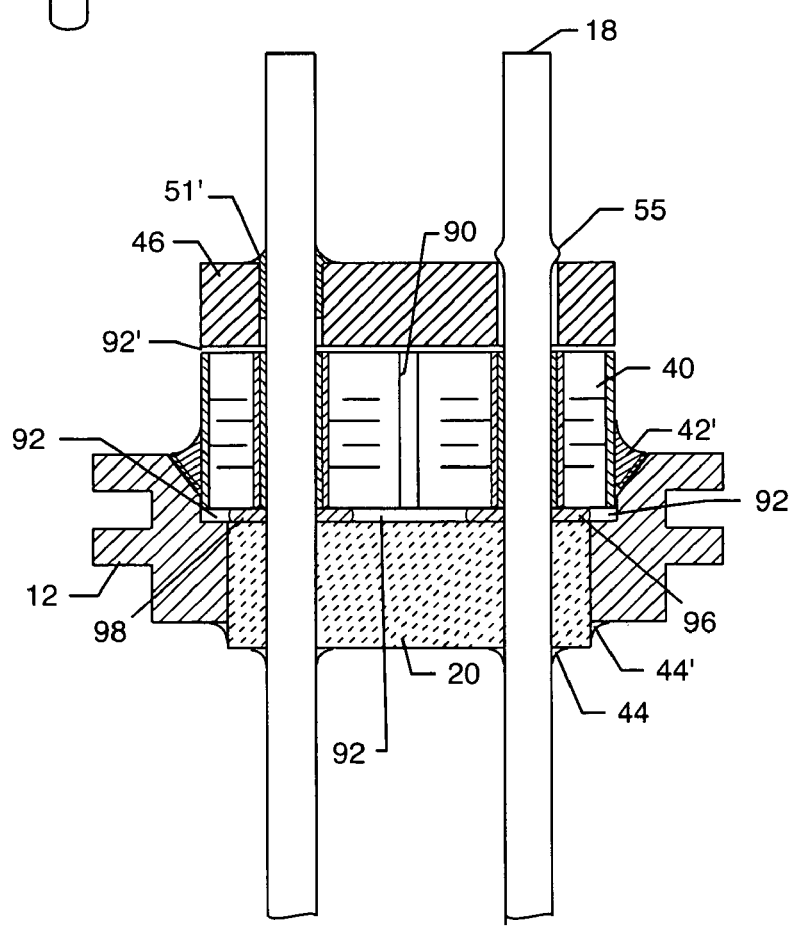
FIG. 81 is a sectional view taken generally along the line 81—81 of FIG. 80.

Referring now to FIG. 80, the quad polar inductor slab 46 is loosely seated on top of capacitor 40 without any bonding material (described in previous drawings as 50'). That is, inductor 46 sits loosely on top of capacitor 40. This is better illustrated in the cross-section shown in FIG. 81. There is an air gap 92' which is formed between the quad polar feedthrough capacitor 40 and inductor slab 46. As one can see, capacitor 40 is relatively thick. This design can be used in cases where there is plenty of room in terms of height inside of the active implantable medical device. Accordingly, it is not necessary that capacitor 40 be thin as described in previous embodiments of the present invention. The relatively thick feedthrough capacitor 40 that is shown in FIGS. 80 and 81 is not particularly volumetrically efficient as can be seen by the blank cover sheet area at the top and bottom of capacitor 40 that is free of electrodes. This is known as the cover sheet area as is normally built up to add the mechanical strength to the capacitor as previously described in FIG. 1.

Referring now back to FIG. 80, it is required that the inductor 46 be retained so that it not fall off or separate away from the ceramic capacitor 40 during shock and vibration loading. Accordingly, a number of different methods of holding the inductor in place are shown. One such method would be to place epoxy pre-forms 51' over each or a few of the four lead wires 18. A cross section of this heat cured epoxy pre-form is also shown in FIG. 81 as material 51'. Another methodology would be to insert a metallic push nut 53 onto one or more of the lead wires 18. Another methodology would be to take a swaging tool and form a crimp or swage in the lead wire 55 as shown. This swage 55 is also shown in the cross section in FIG. 82. Another methodology would be to insert a retaining clip 57 as shown in FIG. 80.

In a multi-polar feedthrough capacitor assembly, it is not necessary to put a retention device on all of the pins. For example, in a six lead or hexpolar device, it may only be necessary to install a retaining feature on two of the leads. This depends on calculations based on the particular shock and vibration requirement of the implantable medical device. It is typical that shock requirements be between 1000 and 1500 g. One would have to calculate the mass of the ferrite slab and then calculate the amount of force that would be applied during such shock loading (F=ma). One can then make a decision as to the number of retaining devices that are required.

Figure 83:
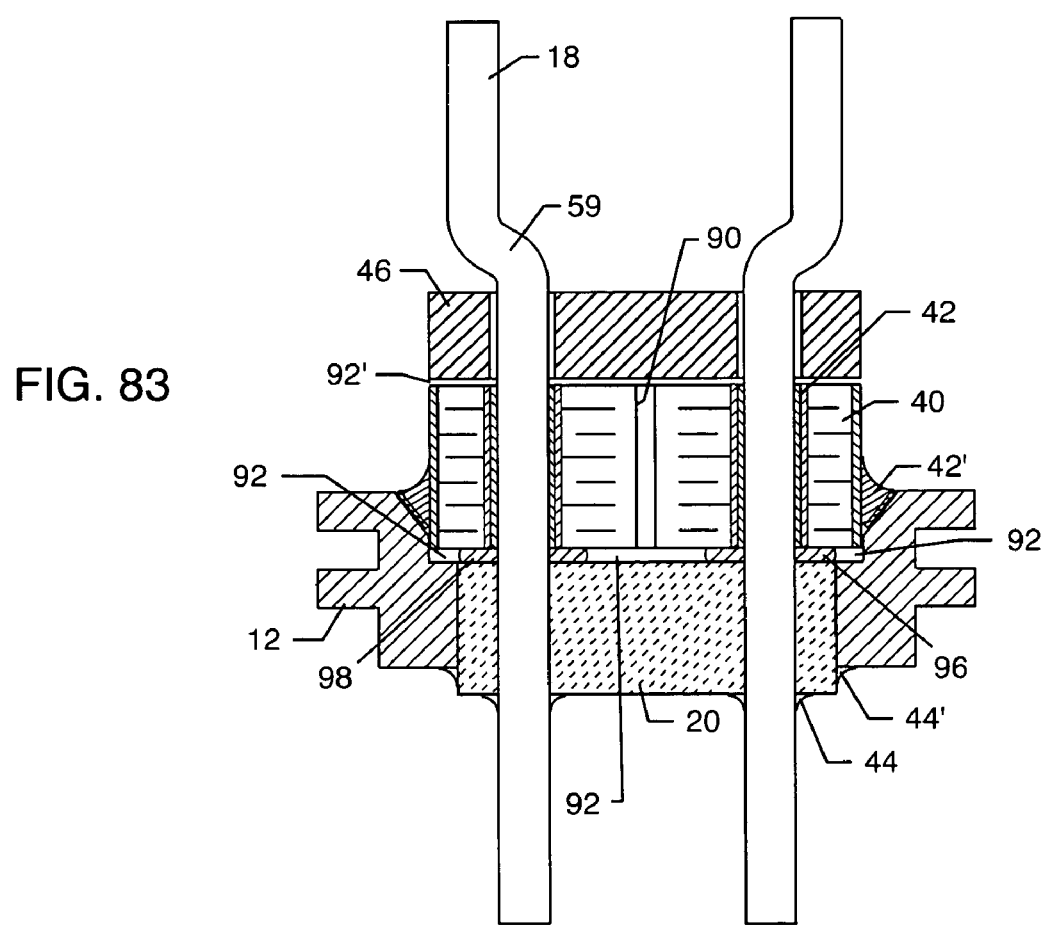
FIG. 83 is a sectional view taken generally along the line 83—83 of FIG. 82.

Referring to FIG. 81, one can see that leak detection vent hole 90 is conveniently placed through the center of the feedthrough capacitor 40. In this particular embodiment there is no need for a corresponding leak detection vent hole in inductor 46. This is because helium gas would readily escape through the air gap 92'. As shown, air gap 92' appears to have significant thickness. However in actual practice, inductor 46 would be pressed down firmly against capacitor 40. However, without a sealing material, helium gas can still escape readily through very small spaces. In fact this is why helium is used in leak detection applications since it is a very small molecule and will escape through even the slightest pinhole. FIGS. 82 and 83 describe another embodiment of the quad polar capacitor assembly previously described in FIGS. 80 and 81. In this case, the inductor 46 is retained by forming or bending one or more of the lead wires 18. It is a very common practice in medical implantable devices that the lead wires be formed or bent in a variety of shapes and configurations so that they line up with appropriate connection points to the internal electronic circuitry of the AIMD. Referring to FIG. 83 one can see that the bend 59 in lead wire 18 firmly holds inductor 46 in place.

Referring once again to FIG. 80, the inductor slab 46 could also be retained by the addition of a wire bond pad. Wire bond pads are the subject of co-pending U.S. patent application Ser. No. 60/548,770.

Figure 84:
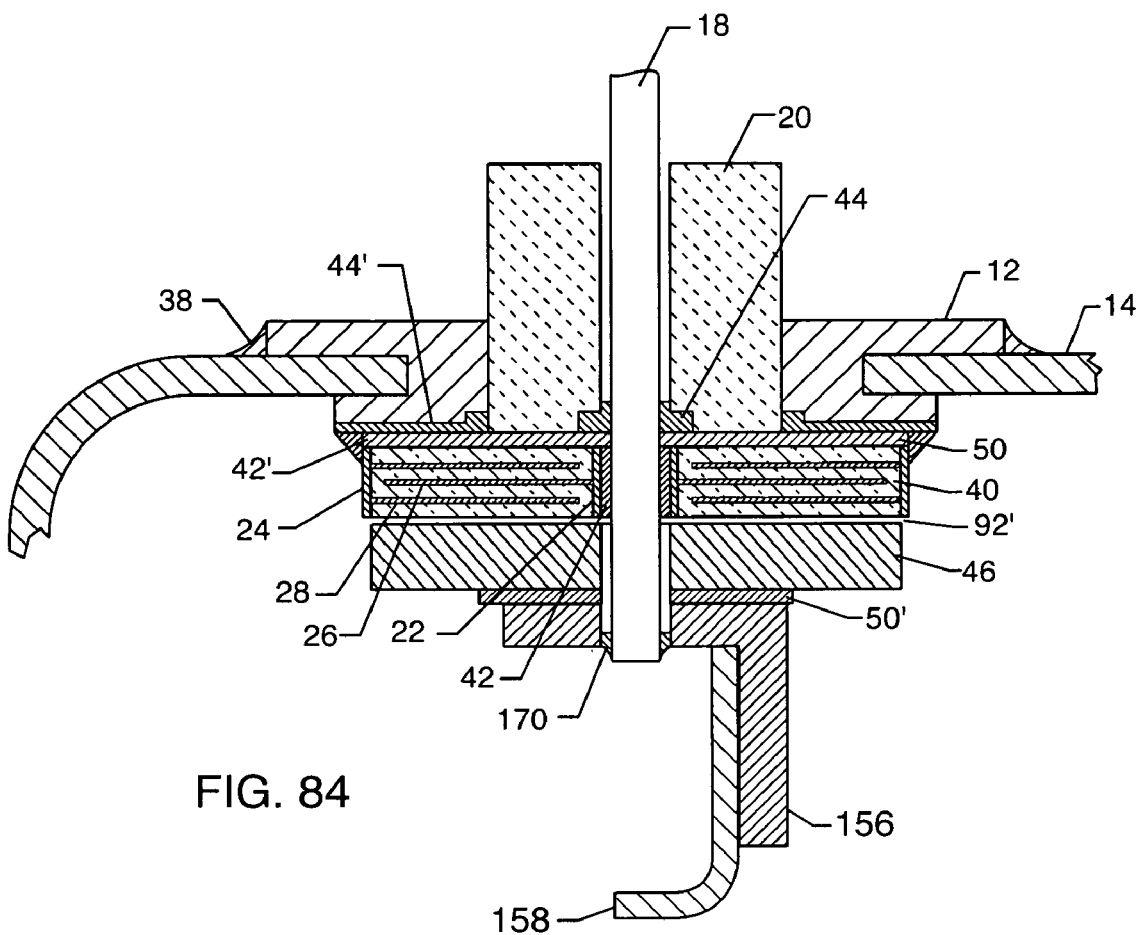
FIG. 84 is a sectional view similar to that illustrated in FIG. 17, illustrating an L-shaped wire bond pad attached using bonding insulating material to the inductor slab.
Figure 85:
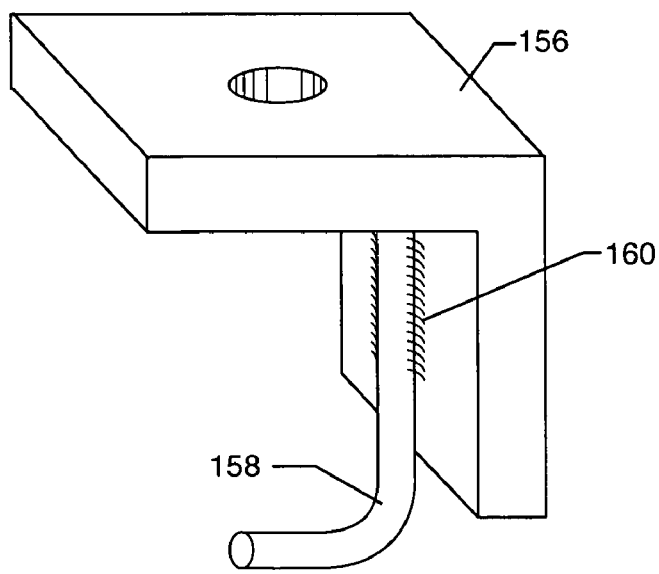
FIG. 85 is a perspective view of the L-shaped wire bond pad of FIG. 84.

FIG. 84 illustrates an L-shaped wire bond pad 156 shown attached using bonding insulating material 50' to inductor slab 46. There is an air gap 92' between inductor 46 and capacitor 40. A perspective view of the L-shaped wire bond pad 156 is shown in FIG. 85. This gold plated wire bond pad 156 is designed for convenient attachment of lead wire 158 either by thermal sonic or ultrasonic wire bonding techniques 160 that are well known in the art.

Figure 86:
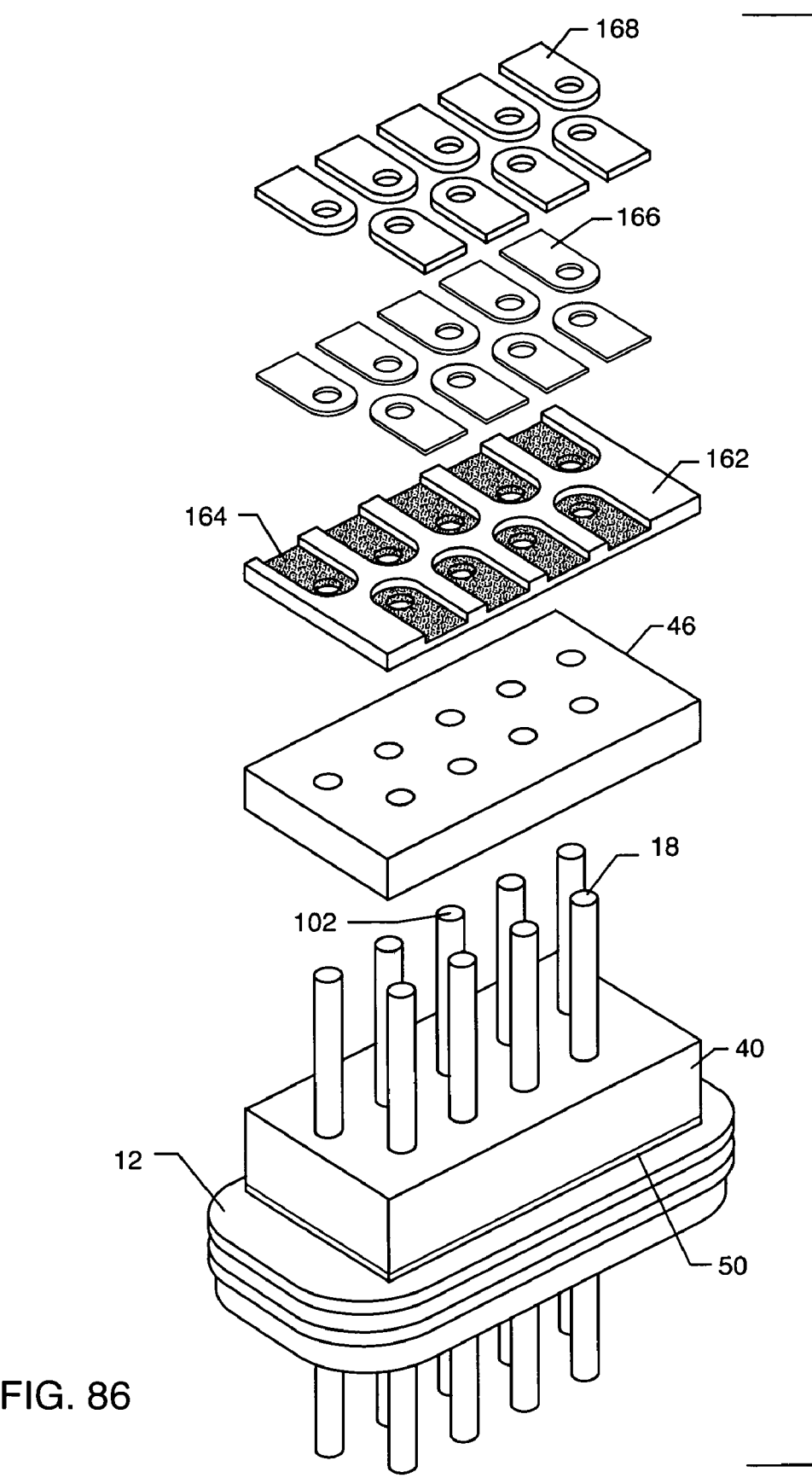
FIG. 86 is an exploded perspective view of an octapolar (plus a grounded lead) feedthrough filter terminal assembly embodying the present invention.

FIG. 86 is an exploded view of an octapolar feedthrough capacitor plus ground lead of the present invention. Shown is a wire bond substrate 162 which is also used to retain the ferrite slab 46. The capacitor 40 is shown seated by way of insulating washer 50 to the ferrule 12 of the hermetic terminal of the implantable medical device. Lead wire 102 is grounded to the ferrule 12 using a weld or gold braze. The inductor slab 46 is slipped down over lead wires 102 and 18 and loosely fitted in place on top of capacitor 40. In this particular case there is no need for a non-conductive polyimide washer or adhesive to bond capacitor 40 and inductor slab 46. This is because capacitor 40 is sufficiently thick to withstand the mechanical and thermal forces of the assembly. In turn, alumina substrate 162 incorporating metallized areas 164 is then slipped down over the lead wires 18 and 102 and seated loosely on top of the ferrite inductor slab 46.

Gold brazed preforms 166 are then slipped over each wire and seated on top of the metallized area 164 of the alumina substrate 162. Nine Kovar wire bond pads 168 are then inserted over the lead wires. These wire bond pads 168 are typically of Kovar or Alloy 42 and the like. The wire bond pads 168 are typically plated with Nickel and then over coated with an ultra pure gold suitable for wire bonding.

Figure 87:
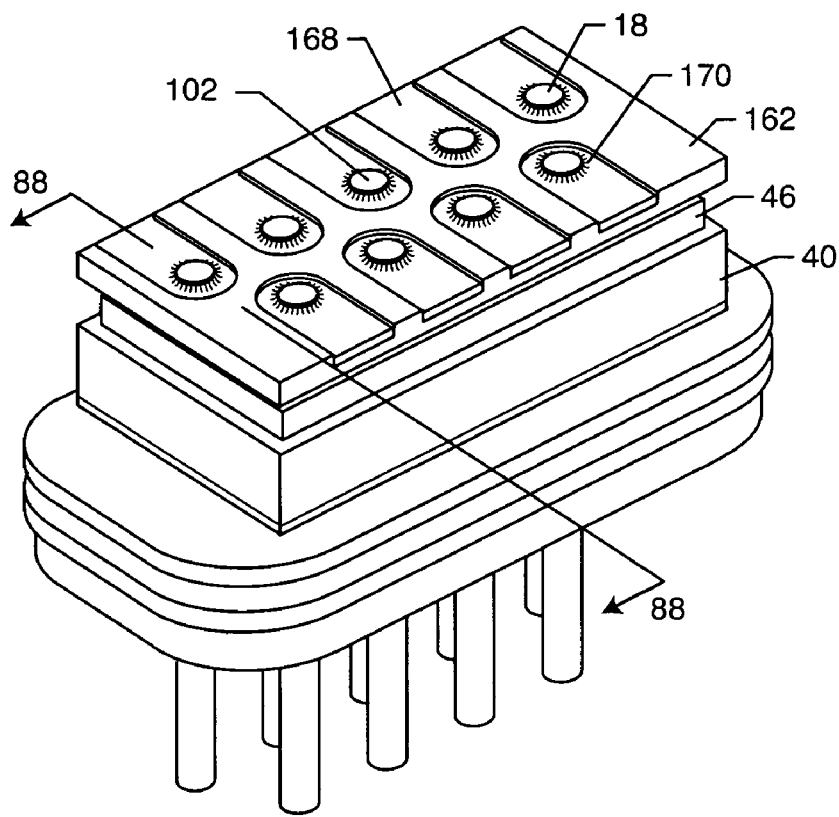
FIG. 87 is a perspective view of the feedthrough terminal assembly of FIG. 86.

FIG. 87 is a perspective view of the completed assembly as shown in FIG. 86. The inductor slab 46 is shown loosely sandwiched between capacitor 40 and wire bond substrate 162. The entire assembly is held in place by nine laser weld connections 170 which attach each of the lead wires to the wire bond pads 168. As described in pending U.S. patent application Ser. No. 60/548,770, laser weld connection 170 makes a highly reliable electrical connection in series with the input and output circuits of an implantable device such as a cardiac pacemaker. Many alternative embodiments of substrates are described in the above-listed pending application. It will be apparent to one skilled in the art that any of these wire bonds substrates could be also used to retain an inductor slab.

Figure 88:
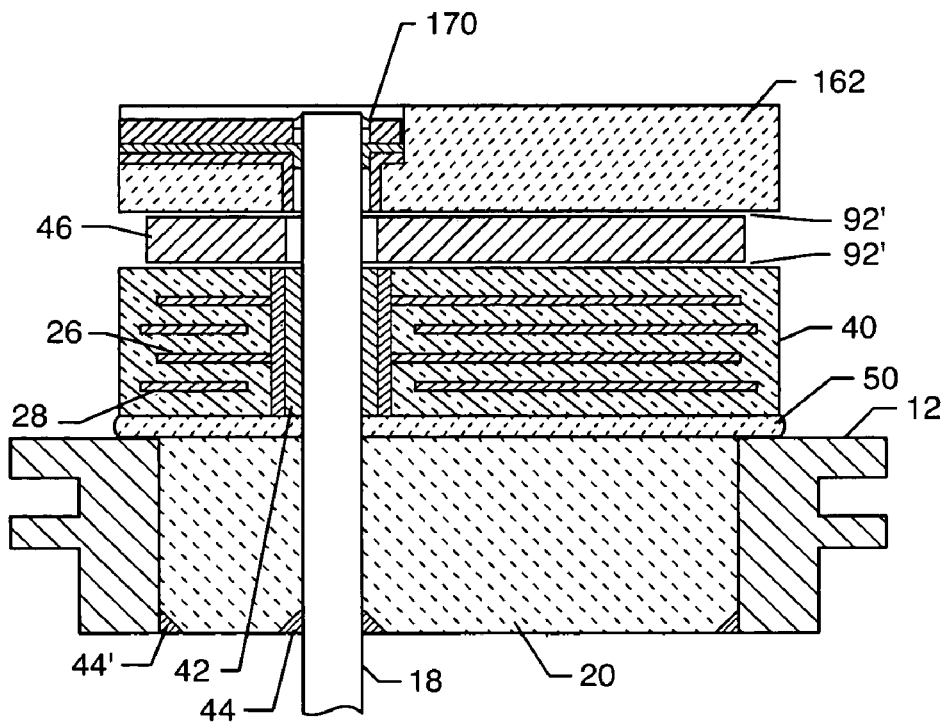
FIG. 88 is an enlarged cross-sectional view taken generally along the line 88—88 of FIG. 87.

FIG. 88 is a cross section of the octapolar feedthrough capacitor as shown in FIG. 87. The inductor 46 is shown loosely held between the capacitor 40 and the wire bond substrate 162. A small space or air gap 92' is formed on both the top and bottom surfaces of the inductor slab 46. The air gap 92' in this case has been exaggerated. In actual practice a weighting fixture would be used to press firmly down on top of the wire bond substrate 162 while laser weld connections 170 are being made. In this way, the alumina substrate 162 would firmly push down against the ferrite slab 46 and the capacitor 40. Accordingly the air gaps 92' would be very small. No additional mechanical connections using thermal setting conductive adhesives are required in the assembly. This is because sufficient mechanical strength to withstand mechanical shock and vibration forces is formed by the laser weld connections 170.

From the foregoing it will be appreciated that EMI filter feedthrough terminal assemblies constructed in accordance with the present invention generally comprise at least one conductive terminal pin, a conductive substrate such as a ferrule through which the terminal pin passes a non-conductive relation, a feedthrough capacitor associated with the ferrule and through which the at least one conductive terminal pin extends, and an inductor adjacent to the capacitor. The feedthrough capacitor is mounted to a hermetic seal subassembly, such as in a manner described in U.S. Pat. Nos. 4,424,551 and 5,333,095. The ferrule is conductively connected to a housing or casing of the human implantable device, as is well-known in the art. The feedthrough capacitor has first and second sets of electrode plates, also known as the active electrode plate set and the ground electrode plate set. The terminal pin extends through the passageway of the capacitor in conductive relation with the active set of electrode plates. The ground set of electrode plates of the capacitor are in conductive relation with the ferrule, which is in turn in conductive relation with the housing of the AIMD.

The conductive terminal pin also extends through the inductor. It is not necessary that the terminal pin be in conductive relation with the inductor. In fact, in an implantable medical device, energy consumption or battery depletion is an important consideration. Therefore, it is desirable that the inductor be well insulated so that leakage current does not shorten the pacemaker battery life. As such, the inductor is preferably electrically insulated from both the capacitor and the terminal pin. The inductor includes a conformal coating such as Paralyne. Such high dielectric strength coatings have a low coefficient of friction, withstand extreme environments, and act as an electrical insulation.

A novel aspect of the present invention is that both the ceramic feedthrough capacitor and the inductor can be made much thinner than conventional practice because they are co-bonded into a monolithic laminate structure, but in non-conductive relation to one another. The inductor can be fixed to the capacitor with a non-conductive polyimide, (as described in FIG. 16), glass, ceramic bonding material, epoxy, or a thermal setting plastic supportive tape adhesive or the like. The monolithic structure of the capacitor and conductor greatly increases the mechanical strength of the structure without greatly increasing the overall volume (height) of the EMI filter.

The inductor typically comprises a high permeability ferrite material and is typically either in the form of a slab or toroid. The inductor may also comprise a molypermalloy material, a powdered iron, a manganese zinc ferrite material, a nickel zinc ferrite material, or a cobalt zinc ferrite material. Such materials are biocompatible as the various materials therein are highly bound.

A unique property of these ferrite materials is that they not only provide inductance but they also have a variable resistance component versus frequency. All ferrite materials involve a trade-off like this. Certain ferrite materials have very high inductance at low frequency. Such ferrite materials typically have a high initial permeability. Accordingly, at high frequency, the inductance tends to decrease. However, in those same ferrite bead materials the resistive loss component tends to increase at high frequency, thereby compensating for the drop in inductance. The important parameter is the overall impedance Z of the ferrite bead. The impedance parameter includes both the inductive reactance and resistive properties of the slab or bead. In general, the total impedance is equal to the square root of the inductive reactance squared, plus the resistance squared.

In certain embodiments, the capacitor and inductor are housed entirely or partially within the ferrule. The inductor is conductively isolated from the ferrule.

The assembly may include a second feedthrough capacitor associated with the inductor. Such capacitor would have the structure as described in relation to the first capacitor and similar to the first capacitor can be externally grounded, internally grounded, or be both internally and externally grounded. In such instances, the first and second feedthrough capacitors are typically disposed on opposite surfaces of the inductor in non-conductive relation thereto.

In other embodiments, the EMI feedthrough filter terminal assembly includes two or more inductors. The terminal pins extend through the additional inductor(s). A second inductor can be disposed above an insulator of the terminal assembly, which is disposed between the terminal pin and the ferrule. Alternatively, the first and second inductors are fixed in non-conductive relation to opposite surfaces of the capacitor. A particularly preferred embodiment stacks the plurality of inductors, such as by laminating them one to another using an adhesive washer or the like.

In a particularly preferred embodiment of the present invention, the terminal pin passes through the inductor so as to create multiple turns to increase inductance. Increasing the number of turns on a ferrite cord dramatically increases the inductance. This is because the inductance varies as the square of the number of the turns. For example, if one increases the number of turns from one to two, the inductance increases by a factor of four. The one or more turns of the terminal pin are electrically isolated from one another. The portion of the terminal pin defining the one or more turns can be encased within a non-conductive sleeve. Alternatively, the one or more turns of the terminal pin are encased in a non-conductive material.

To facilitate the passing of multiple turns through the inductor, a notch is formed in the inductor which is adapted to permit the terminal pin to be passed therethrough and form the one or more turns with respect to the inductor. A ramp may be incorporated in the notch for facilitating the passing of the terminal pin. The inductor may include multiple notches to accommodate multiple turns of a single terminal pin or to accommodate multiple terminal pins. In one embodiment, each notch includes multiple slots formed therein to permit an additional turn of the terminal pin therethrough.

The capacitor and the inductor may include aligned apertures which co-operate with an air gap between the ceramic capacitor and the insulative hermetic seal. This allows a leak detection gas to quickly pass through to readily detect defective hermetic seal connections.

Moreover, as described above, the feedthrough capacitor assembly incorporating an inductor can be utilized in many other different types of designs for feedthrough terminal assemblies advantageously.

Although several embodiments of the present invention have been described in detail for purposes of illustration, various modifications of each may be made without departing from the spirit and scope of the invention. Accordingly, the invention is not to be limited, except as by the appended claims.

What is claimed is:

1. A feedthrough terminal assembly for an active implantable medical device, comprising:
   a conductive ferrule conductively coupled to a housing of the active implantable medical device;
   a feedthrough capacitor having first and second sets of electrode plates, the second set of electrode plates being conductively coupled to the ferrule;
   an inductor having a surface bonded to an adjacent surface of the capacitor with a non-conductive material; and
   a conductive terminal pin extending through the capacitor and the inductor, the terminal pin extending through the inductor in non-conductive relation and conductively coupled to the first set of electrode plates.

2. The assembly of claim 1, wherein the active implantable medical device comprises a cardiac pacemaker, an implantable defibrillator, a cochlear implant, a neurostimulator, a drug pump, a ventricular assist device, an implantable sensing system, a gastric pacemaker or a prosthetic device.

3. The assembly of claim 1, wherein the capacitor and the inductor are housed within the ferrule.

4. The assembly of claim 3, including an insulative cap disposed over the inductor opposite the capacitor.

5. The assembly of claim 1, wherein the capacitor is disposed on a body fluid side of the feedthrough terminal assembly.

6. The assembly of claim 1, wherein the feedthrough capacitor comprises first and second feedthrough capacitors associated with the inductor in non-conductive relation.

7. The assembly of claim 6, wherein the first and second feedthrough capacitors are disposed adjacent to opposing surfaces of the inductor.

8. The assembly of claim 7, wherein the capacitors are bonded to the inductor.

9. The assembly of claim 7, wherein each capacitor is internally grounded.

10. The assembly of claim 6, wherein the first and second capacitors each include a first set of electrode plates conductively coupled to the terminal pin, and a second set of electrode plates conductively coupled to the ferrule.

11. The assembly of claim 10, wherein the first capacitor comprises an externally grounded capacitor, and the second capacitor comprises an internally grounded capacitor, the feedthrough terminal assembly further including a conductive material extending through both the first and second feedthrough capacitors to conductively couple the second set of electrode plates of the second capacitor with the second set of electrode plates of the first capacitor.

12. The assembly of claim 11, wherein the first and second feedthrough capacitors are disposed adjacent to opposing surfaces of the inductor.

13. The assembly of claim 11, wherein the conductive material comprises a thermal setting conductive adhesive, a solder, or a solder paste.

14. The assembly of claim 11, wherein the conductive material comprises a conductive pin.

15. The assembly of claim 14, wherein the conductive pin comprises a nail head pin.

16. The assembly of claim 14, wherein the conductive pin comprises a pin attached to an underlying hermetic insulator.

17. The assembly of claim 1, including an hermetic insulator disposed between the terminal pin and the ferrule, wherein the capacitor is disposed adjacent to the hermetic insulator.

18. The assembly of claim 17, wherein the inductor and the capacitor each include an aperture through which a leak detection gas can be detected.

19. The assembly of claim 1, wherein the terminal pin is wound about the inductor to form multiple turns.

20. The assembly of claim 19, wherein adjacent portions of the wound terminal pin are electrically insulated from one another.

21. The assembly of claim 20, wherein the adjacent portions of the wound terminal pin are encased in a non-conductive material.

22. The assembly of claim 21, wherein the adjacent portions of the wound terminal pin are encased within a non-conductive sleeve.

23. The assembly of claim 19, wherein the inductor includes a notch for receiving the wound terminal pin.

24. The assembly of claim 23, including a ramp formed in the notch.

25. The assembly of claim 23, wherein the inductor includes multiple notches therein.

26. The assembly of claim 25, wherein each notch accommodates a separate terminal pin therein.

27. The assembly of claim 23, wherein the notch includes multiple slots for receiving corresponding multiple turns of the terminal pin.

28. The assembly of claim 23, wherein the notch comprises contoured corners for accommodating the terminal pin.

29. The assembly of claim 1, including a plurality of distinct feedthrough capacitors each having a respective terminal pin extending therethrough, wherein the inductor is non-conductively associated with each of the plurality of feedthrough capacitors.

30. The assembly of claim 1, including means for maintaining the inductor in close association with the capacitor without forming a direct physical attachment therebetween.

31. The assembly of claim 30, wherein the maintaining means comprises a lock associated with the terminal pin.

32. The assembly of claim 31, wherein the lock comprises a mechanical lock.

33. The assembly of claim 31, wherein the lock comprises a deformation in the terminal pin.

34. The assembly of claim 31, wherein the lock comprises a cured polymer.

35. The assembly of claim 30, wherein the maintaining means comprises a wire bond pad attached to the terminal pin.

36. The assembly of claim 35, including a non-conductive substrate disposed between the wire bond pad and the inductor.

37. The assembly of claim 1, wherein the non-conductive material comprises a washer.

38. The assembly of claim 37, wherein the washer comprises a thin film, adhesive-backed washer.

39. The assembly of claim 1, wherein the non-conductive material comprises polyimide.

40. A feedthrough terminal assembly for an active implantable medical device, comprising:
   a conductive ferrule conductively coupled to a housing of the active implantable medical device;
   a feedthrough capacitor having first and second sets of electrode plates, the second set of electrode plates being conductively coupled to the ferrule;
   an inductor closely associated with the capacitor in non-conductive relation; and
   a conductive terminal pin extending through the capacitor and the inductor, the terminal pin extending through the inductor in non-conductive relation and conductively coupled to the first set of electrode plates;
   wherein the inductor comprises a high permeability ferrite material.

41. The assembly of claim 40, wherein the inductor comprises a material selected from cobalt zinc ferrite, nickel zinc ferrite, manganese zinc ferrite, powdered iron, or molypermalloy.

42. A feedthrough terminal assembly for an active implantable medical device, comprising:
   a conductive ferrule conductively coupled to a housing of the active implantable medical device;
   a feedthrough capacitor having first and second sets of electrode plates, the second set of electrode plates being conductively coupled to the ferrule;
   an inductor closely associated with the capacitor in non-conductive relation;
   a conductive terminal pin extending through the capacitor and the inductor, the terminal pin extending through the inductor in non-conductive relation and conductively coupled to the first set of electrode plates; and
   a conformal coating over the inductor.

43. The assembly of claim 42, wherein the conformal coating comprises Paralyne.

44. The assembly of claim 43, wherein the conformal coating comprises Paralyne C, D, E, or N.

45. A feedthrough terminal assembly for an active implantable medical device, comprising:
   a conductive ferrule conductively coupled to a housing of the active implantable medical device;
   a feedthrough capacitor having first and second sets of electrode plates, the second set of electrode plates being conductively coupled to the ferrule;
   an inductor closely associated with the capacitor in non-conductive relation;

a conductive terminal pin extending through the capacitor and the inductor, the terminal pin extending through the inductor in non-conductive relation and conductively coupled to the first set of electrode plates; and an insulator disposed between the inductor and the terminal pin.

46. The assembly of claim 45, wherein the insulator comprises a non-conductive polymer.

47. The assembly of claim 46, wherein the non-conductive polymer comprises an epoxy, a thermal-setting non-conductive adhesive, a non-conductive polyimide, or a silicone material.

48. A feedthrough terminal assembly for an active implantable medical device, comprising:

a conductive ferrule conductively coupled to a housing of the active implantable medical device;

a feedthrough capacitor having first and second sets of electrode plates, the second set of electrode plates being conductively coupled to the ferrule;

an inductor closely associated with the capacitor in non-conductive relation;

a conductive terminal pin extending through the capacitor and the inductor, the terminal pin extending through the inductor in non-conductive relation and conductively coupled to the first set of electrode plates; and a second inductor through which the terminal pin extends in non-conductive relation.

49. The assembly of claim 48, wherein the inductors are disposed adjacent to one another.

50. The assembly of claim 49, comprising at least one additional inductor stacked onto another one of the inductors.

51. The assembly of claim 49, wherein the inductors are each comprised of materials having different physical or electrical properties.

52. The assembly of claim 49, wherein the inductors are each comprised of materials having the same physical or electrical properties.

53. The assembly of claim 48, wherein the inductors are disposed on opposite sides of the capacitor.

54. The assembly of claim 53, wherein at least one of the inductors is disposed on a body fluid side of the feedthrough terminal assembly.

55. The assembly of claim 53, wherein the second inductor is disposed adjacent to the ferrule.

56. The assembly of claim 53, wherein the inductors are disposed adjacent to opposing surfaces of the capacitor.

57. The assembly of claim 56, wherein the inductors are bonded to the capacitor.

58. The assembly of claim 56, wherein the capacitor and the inductors are disposed within and conductively isolated from the ferrule.

59. A feedthrough terminal assembly for an active implantable medical device, comprising:

a conductive ferrule conductively coupled to a housing of the active implantable medical device;

a feedthrough capacitor having first and second sets of electrode plates, the second set of electrode plates being conductively coupled to the ferrule;

an inductor closely associated with the capacitor in non-conductive relation; and a conductive terminal pin extending through the capacitor and the inductor, the terminal pin extending through the inductor in non-conductive relation and conductively coupled to the first set of electrode plates;

wherein the capacitor's second set of electrode plates are externally grounded to the ferrule.

60. A feedthrough terminal assembly for an active implantable medical device, comprising:

a conductive ferrule conductively coupled to a housing of the active implantable medical device;

a feedthrough capacitor having first and second sets of electrode plates, the second set of electrode plates being conductively coupled to the ferrule;

an inductor closely associated with the capacitor in non-conductive relation; and a conductive terminal pin extending through the capacitor and the inductor, the terminal pin extending through the inductor in non-conductive relation and conductively coupled to the first set of electrode plates;

wherein the capacitor's second set of electrode plates are internally grounded to the ferrule.

61. A feedthrough terminal assembly for an active implantable medical device, comprising:

a conductive ferrule conductively coupled to a housing of the active implantable medical device;

a feedthrough capacitor having first and second sets of electrode plates, the second set of electrode plates being conductively coupled to the ferrule;

a first inductor bonded to the capacitor in non-conductive relation;

a second inductor bonded to the capacitor in non-conductive relation, the second inductor being disposed opposite the first conductor relative to the capacitor; and a conductive terminal pin extending through the capacitor and the inductors, the terminal pin extending through the inductors in non-conductive relation and conductively coupled to the first set of electrode plates.

62. The assembly of claim 61, wherein the active implantable medical device comprises a cardiac pacemaker, an implantable defibrillator, a cochlear implant, a neurostimulator, a drug pump, a ventricular assist device, an implantable sensing system, a gastric pacemaker or a prosthetic device.

63. The assembly of claim 61, wherein the inductors comprise a high permeability ferrite material.

64. The assembly of claim 63, wherein the inductors comprise a material selected from cobalt zinc ferrite, nickel zinc ferrite, manganese zinc ferrite, powdered iron, or molypermalloy.

65. The assembly of claim 61, including a conformal coating over the inductors.

66. The assembly of claim 65, wherein the conformal coating comprises Paralyne.

67. The assembly of claim 61, including insulators disposed between the inductors and the terminal pin.

68. The assembly of claim 67, wherein the insulators comprise a non-conductive polymer.

69. The assembly of claim 61, including a third inductor through which the terminal pin extends in non-conductive relation.

70. The assembly of claim 69, wherein the first and third inductors are disposed adjacent to one another.

71. The assembly of claim 70, comprising at least one additional inductor stacked onto the third inductor.

72. The assembly of claim 61, wherein the inductors are each comprised of materials having different physical or electrical properties.

73. The assembly of claim 61, wherein the inductors are each comprised of materials having the same physical or electrical properties.

74. The assembly of claim 61, wherein the capacitor and the inductors are housed within the ferrule.

75. The assembly of claim 74, including an insulative cap disposed over one of the inductors opposite the capacitor.

76. The assembly of claim 61, wherein at least one of the inductors is disposed on a body fluid side of the feedthrough terminal assembly.

77. The assembly of claim 61, wherein the second inductor is disposed adjacent to the ferrule.

78. The assembly of claim 61, wherein the inductors are disposed adjacent to opposing surfaces of the capacitor.

79. The assembly of claim 78, wherein the capacitor and the inductors are disposed within and conductively isolated from the ferrule.

80. The assembly of claim 61, wherein the capacitor is disposed on a body fluid side of the feedthrough terminal assembly.

81. The assembly of claim 61, including an hermetic insulator disposed between the terminal pin and the ferrule, wherein the capacitor is disposed adjacent to the hermetic insulator.

82. The assembly of claim 61, wherein the capacitor's second set of electrode plates are externally grounded to the ferrule.

83. The assembly of claim 61, wherein the capacitor's second set of electrode plates are internally grounded to the ferrule.

84. The assembly of claim 61, wherein the terminal pin is wound about at least one of the inductors to form multiple turns.

85. The assembly of claim 84, wherein adjacent portions of the wound terminal pin are electrically insulated from one another.

86. The assembly of claim 85, wherein the adjacent portions of the wound terminal pin are encased in a non-conductive material.

87. The assembly of claim 86, wherein the adjacent portions of the wound terminal pin are encased within a non-conductive sleeve.

88. The assembly of claim 84, wherein at least one of the inductors includes a notch for receiving the wound terminal pin.

89. The assembly of claim 88, including a ramp formed in the notch.

90. The assembly of claim 88, wherein the inductor includes multiple notches therein.

91. The assembly of claim 90, wherein each notch accommodates a separate terminal pin therein.

92. The assembly of claim 88, wherein the notch includes multiple slots for receiving corresponding multiple turns of the terminal pin.

93. The assembly of claim 88, wherein the notch comprises contoured corners for accommodating the terminal pin.

94. The assembly of claim 61, including means for maintaining at least one of the inductors in close association with the capacitor without forming a direct physical attachment therebetween.

95. The assembly of claim 94, wherein the maintaining means comprises a lock associated with the terminal pin.

96. The assembly of claim 95, wherein the lock comprises a mechanical lock.

97. The assembly of claim 95, wherein the lock comprises a deformation in the terminal pin.

98. The assembly of claim 95, wherein the lock comprises a cured polymer.

100. The assembly of claim 94, wherein the maintaining means comprises a wire bond pad attached to the terminal pin.

100. The assembly of claim 61, wherein the inductor is bonded to the capacitor with a non-conductive washer.

101. A feedthrough terminal assembly for an active implantable medical device, comprising:
 a conductive ferrule conductively coupled to a housing of the active implantable medical device;
 a first feedthrough capacitor having first and second sets of electrode plates, the second set of electrode plates being conductively coupled to the ferrule;
 a second feedthough capacitor having first and second sets of electrode plates, the second set of electrode plates being conductively coupled to the ferrule;
 an inductor disposed between and bonded to the capacitors in non-conductive relation; and
 a conductive terminal pin extending throught the capacitors and the inductor, the terminal pin extending through the inductor in non-conductive relation and conductively coupled to the first sets of electrode plates of both capacitors.

102. The assembly of claim 101, wherein the active implantable medical device comprises a cardiac pacemaker, an implantable defibrillator, a cochlear implant, a neurostimulator, a drug pump, a ventricular assist device, an implantable sensing system, a gastric pacemaker or a prosthetic device.

103. The assembly of claim 101, wherein the inductor is bonded to the capacitors utilizing a non-conductive polyimide, glass, Paralyne, a ceramic bonding material, epoxy, silicone, or a thermal plastic supportive tape adhesive.

104. The assembly of claim 101, wherein the inductor comprises a high permeability ferrite material.

105. The assembly of claim 104, wherein the inductor comprises a material selected from cobalt zinc ferrite, nickel zinc ferrite, manganese zinc ferrite, powdered iron, or molypermalloy.

106. The assembly of claim 101, including a conformal coating over the inductor.

107. The assembly of claim 106, wherein the conformal coating comprises Paralyne C, D, E, or N.

108. The assembly of claim 101, including an insulator disposed between the inductor and the terminal pin.

109. The assembly of claim 108, wherein the insulator comprises a non-conductive polymer.

110. The assembly of claim 109, wherein the non-conductive polymer comprises an epoxy, a thermal-setting non-conductive adhesive, a non-conductive polyimide, or a silicone material.

111. The assembly of claim 101, wherein at least one of the capacitors and the inductor are housed within the ferrule.

112. The assembly of claim 101, wherein at least one of the capacitors is disposed on a body fluid side of the feedthrough terminal assembly.

113. The assembly of claim 101, wherein the first and second feedthrough capacitors are disposed adjacent to opposing surfaces of the inductor.

114. The assembly of claim 113, wherein the capacitors are bonded to the inductor.

115. The assembly of claim 113, wherein each capacitor is internally grounded.

116. The assembly of claim 101, wherein the first and second capacitors each include a first set of electrode plates conductively coupled to the terminal pin, and a second set of electrode plates conductively coupled to the ferrule.

117. The assembly of claim 116, wherein the first capacitor comprises an externally grounded capacitor, and the second capacitor comprises an internally grounded capacitor, the feedthrough terminal assembly further including a conductive material extending through both the first and second feedthrough capacitors to conductively couple the second set of electrode plates of the second capacitor with the second set of electrode plates of the first capacitor.

118. The assembly of claim 117, wherein the first and second feedthrough capacitors are disposed adjacent to opposing surfaces of the inductor.

119. The assembly of claim 117, wherein the conductive material comprises a thermal setting conductive adhesive, a solder, or a solder paste.

120. The assembly of claim 117, wherein the conductive material comprises a conductive pin.

121. The assembly of claim 120, wherein the conductive pin comprises a nail head pin.

122. The assembly of claim 120, wherein the conductive pin comprises a pin attached to an underlying hermetic insulator.

123. The assembly of claim 101, including an hermetic insulator disposed between the terminal pin and the ferrule, wherein at least one of the capacitors is disposed adjacent to the hermetic insulator.

124. The assembly of claim 123, wherein at least one of the inductors and the capacitors each include an aperture through which a leak detection gas can be detected.

125. The assembly of claim 101, wherein at least one of the capacitors' second set of electrode plates are externally grounded to the ferrule.

126. The assembly of claim 101, wherein at least one of the capacitors' second set of electrode plates are internally grounded to the ferrule.

127. The assembly of claim 101, wherein the terminal pin is wound about the inductor to form multiple turns.

128. The assembly of claim 127, wherein adjacent portions of the wound terminal pin are electrically insulated from one another.

129. The assembly of claim 128, wherein the adjacent portions of the wound terminal pin are encased in a non-conductive material.

130. The assembly of claim 129, wherein the adjacent portions of the wound terminal pin are encased within a non-conductive sleeve.

131. The assembly of claim 127, wherein the inductor includes a notch for receiving the wound terminal pin.

132. The assembly of claim 130, including a ramp formed in the notch.

133. The assembly of claim 130, wherein the inductor includes multiple notches therein.

134. The assembly of claim 133, wherein each notch accommodates a separate terminal pin therein.

135. The assembly of claim 131, wherein the notch includes multiple slots for receiving corresponding multiple turns of the terminal pin.

136. The assembly of claim 131, wherein the notch comprises contoured corners for accommodating the terminal pin.

137. The assembly of claim 101, including means for maintaining the inductor in close association with at least one of the capacitors without forming a direct physical attachment therebetween.

138. The assembly of claim 137, wherein the maintaining means comprises a lock associated with the terminal pin.

139. The assembly of claim 138, wherein the lock comprises a mechanical lock.

140. The assembly of claim 138, wherein the lock comprises a deformation in the terminal pin.

141. The assembly of claim 138, wherein the lock comprises a cured polymer.

142. The assembly of claim 137, wherein the maintaining means comprises a wire bond pad attached to the terminal pin.

143. The assembly of claim 101, wherein the capacitors are bonded to the inductor with non-conductive washers.

144. A feedthrough terminal assembly for an active implantable medical device, comprising;
 a conductive ferrule conductively coupled to a housing of the active implantable medical device;
 an externally grounded feedthrough capacitor having first and second sets of electrode plates, the second set of electrode plates being conductively coupled to the ferrule;
 an internally grounded feedthrough capacitor having first and second sets of electrode plates, the second set of electrode plates of the internally grounded capacitor being conductively coupled to the second set of electrode plates of the first capacitor;
 an inductor disposed between and closely associated with the capacitors in non-conductive relation; and
 a conductive terminal pin extending through the capacitors and the inductor, the terminal pin extending through the inductor in non-conductive relation and conductively coupled to the first sets of electrode plates of both capacitors.

145. The assembly of claim 144, wherein the active implantable medical device comprises a cardiac pacemaker, an implantable defibrillator, a cochlear implant, a neurostimulator, a drug pump, a ventricular assist device, an implantable sensing system, a gastric pacemaker or a prosthetic device.

146. The assembly of claim 144, wherein the inductor comprises a high permeability ferrite material.

147. The assembly of claim 146, wherein the inductor comprises a material selected from cobalt zinc ferrite, nickel zinc ferrite, manganese zinc ferrite, powdered iron, or molypermalloy.

148. The assembly of claim 144, including a conformal coating over the inductor.

149. The assembly of claim 148, wherein the conformal coating comprises Paralyne.

150. The assembly of claim 149, wherein the conformal coating comprises Paralyne C, D, E, or N.

151. The assembly of claim 144, including a conductive material extending through both the first and second feedthrough capacitors to conductively couple the second set of electrode plates of the second capacitor with the second set of electrode plates of the first capacitor.

152. The assembly of claim 151, wherein the capacitors are disposed adjacent to opposing surfaces of the inductor.

153. The assembly of claim 151, wherein the conductive material comprises a thermal setting conductive adhesive, a solder, or a solder paste.

154. The assembly of claim 151, wherein the conductive material comprises a conductive pin.

155. The assembly of claim 154, wherein the conductive pin comprises a nail head pin.

156. The assembly of claim 154, wherein the conductive pin comprises a pin attached to an underlying hermetic insulator.

157. The assembly of claim 144, wherein the terminal pin is wound about the inductor to form multiple turns.

158. The assembly of claim 157, wherein adjacent portions of the wound terminal pin are electrically insulated from one another.

159. The assembly of claim 158, wherein the adjacent portions of the wound terminal pin are encased in a non-conductive material.

160. The assembly of claim 159, wherein the adjacent portions of the wound terminal pin are encased within a non-conductive sleeve.

161. The assembly of claim 157, wherein the inductor includes a notch for receiving the wound terminal pin.

162. The assembly of claim 161, including a ramp formed in the notch.

163. The assembly of claim 161, wherein the inductor includes multiple notches therein.

164. The assembly of claim 163, wherein each notch accommodates a separate terminal pin therein.

165. The assembly of claim 161, wherein the notch includes multiple slots for receiving corresponding multiple turns of the terminal pin.

166. The assembly of claim 161, wherein the notch comprises contoured corners for accommodating the terminal pin.

167. The assembly of claim 144, including means for maintaining the inductor in close association with at least one of the capacitors without forming a direct physical attachment therebetween.

168. The assembly of claim 167, wherein the maintaining means comprises a lock associated with the terminal pin.

169. The assembly of claim 168, wherein the lock comprises a mechanical lock.

170. The assembly of claim 168, wherein the lock comprises a deformation in the terminal pin.

171. The assembly of claim 168, wherein the lock comprises a cured polymer.

172. The assembly of claim 167, wherein the maintaining means comprises a wire bond pad attached to the terminal pin.

173. A feedthrough terminal assembly for an active implantable medical device, comprising:
a conductive ferrule conductively coupled to a housing of the active implantable medical device;
a feedthrough capacitor having first and second sets of electrode plates, the second set of electrode plates being conductively coupled to the ferrule, wherein the capacitor's second set of electrodes are externally grounded to the ferrule;
an inductor associated with the capacitor in non-conductive relation; means for maintaining the inductor in close association with the capacitor without forming a direct physical attachment therebetween; and
a conductive terminal pin extending through the capacitor and the inductor, the terminal pin extending through the inductor in non-conductive relation and conductively coupled to the first set of electrode plates.

174. The assembly of claim 173, wherein the maintaining means comprises a lock associated with the terminal pin.

175. The assembly of claim 174, wherein the lock comprises a mechanical lock.

176. The assembly of claim 174, wherein the lock comprises a deformation in the terminal pin.

177. The assembly of claim 174, wherein the lock comprises a cured polymer.

178. The assembly of claim 173, wherein the maintaining means comprises a wire bond pad attached to the terminal pin.

179. The assembly of claim 178, including a non-conductive substrate disposed between the wire bond pad and the inductor.

180. The assembly of claim 173, wherein the active implantable medical device comprises a cardiac pacemaker, an implantable defibrillator, a cochlear implant, a neurostimulator, a drug pump, a ventricular assist device, an implantable sensing system, a gastric pacemaker or a prosthetic device.

181. The assembly of claim 173, wherein the inductor is bonded to the capacitor utilizing a non-conductive polyimide, glass, Paralyne, a ceramic bonding material, epoxy, silicone, or a thermal plastic supportive tape adhesive.

182. The assembly of claim 173, wherein the inductor comprises a material selected from cobalt zinc ferrite, nickel zinc ferrite, manganese zinc ferrite, powdered iron, or molypermalloy.

183. The assembly of claim 173, including a conformal coating over the inductor comprising Paralyne.

184. The assembly of claim 173, including an insulator disposed between the inductor and the terminal pin, wherein the insulator comprises a non-conductive polymer.

185. The assembly of claim 184, wherein the non-conductive polymer comprises an epoxy, a thermal-setting non-conductive adhesive, a non-conductive polyimide, or a silicone material.

186. The assembly of claim 173, including a second inductor through which the terminal pin extends in non-conductive relation.

187. The assembly of claim 186, wherein the inductors are disposed adjacent to one another.

188. The assembly of claim 187, comprising at least one additional inductor stacked onto another one of the inductors.

189. The assembly of claim 187, wherein the inductors are each comprised of materials having different physical or electrical properties.

190. The assembly of claim 187, wherein the inductors are each comprised of materials having the same physical or electrical properties.

191. The assembly of claim 186, wherein the inductors are disposed on opposite sides of the capacitor.

192. The assembly of claim 191, wherein at least one of the inductors is disposed on a body fluid side of the feedthrough terminal assembly.

193. The assembly of claim 191, wherein the second inductor is disposed adjacent to the ferrule.

194. The assembly of claim 191, wherein the inductors are disposed adjacent to opposing surfaces of the capacitor.

195. The assembly of claim 194, wherein the inductors are bonded to the capacitor.

196. The assembly of claim 194, wherein the capacitor and the inductors are disposed within and conductively isolated from the ferrule.

197. The assembly of claim 173, wherein the capacitor and the inductor are housed within the ferrule.

198. The assembly of claim 197, including an insulative cap disposed over the inductor opposite the capacitor.

199. The assembly of claim 173, wherein the capacitor is disposed on a body fluid side of the feedthrough terminal assembly.

200. The assembly of claim 173, wherein the feedthrough capacitor comprises first and second feedthrough capacitors associated with the inductor in non-conductive relation.

201. The assembly of claim 200, wherein the first and second feedthrough capacitors are disposed adjacent to opposing surfaces of the inductor.

202. The assembly of claim 201, wherein the capacitors are bonded to the inductor.

203. The assembly of claim 201, wherein each capacitor is internally grounded.

204. The assembly of claim 200, wherein the first and second capacitors each include a first set of electrode plates conductively coupled to the terminal pin, and a second set of electrode plates conductively coupled to the ferrule.

205. The assembly of claim 204, wherein the first capacitor comprises an externally grounded capacitor, and the second capacitor comprises an internally grounded capacitor, the feedthrough terminal assembly further including a conductive material extending through both the first and second feedthrough capacitors to conductively couple the second set of electrode plates of the second capacitor with the second set of electrode plates of the first capacitor.

206. The assembly of claim 205, wherein the first and second feedthrough capacitors are disposed adjacent to opposing surfaces of the inductor.

207. The assembly of claim 205, wherein the conductive material comprises a thermal setting conductive adhesive, a solder, or a solder paste.

208. The assembly of claim 205, wherein the conductive material comprises a conductive pin.

209. The assembly of claim 208, wherein the conductive pin comprises a nail head pin.

210. The assembly of claim 208, wherein the conductive pin comprises a pin attached to an underlying hermetic insulator.

211. The assembly of claim 173, including an hermetic insulator disposed between the terminal pin and the ferrule, wherein the capacitor is disposed adjacent to the hermetic insulator.

212. The assembly of claim 211, wherein the inductor and the capacitor each include an aperture through which a leak detection gas can be detected.

213. A feedthrough terminal assembly for an active implantable medical device, comprising:
a conductive ferrule conductively coupled to a housing of the active implantable medical device;
a feedthrough capacitor having first and second sets of electrode plates, the second set of electrode plates being conductively coupled to the ferrule;
an inductor associated with the capacitor in non-conductive relation;
means for maintaining the inductor in close association with the capacitor without forming a direct physical attachment therebetween; and
a conductive terminal pin extending through the capacitor and the inductor, the terminal pin extending through the inductor in non-conductive relation and conductively coupled to the first set of electrode plates;
wherein the capacitor's second set of electrode plates are internally grounded to the ferrule.

214. The assembly of claim 213, wherein the maintaining means comprises a lock associated with the terminal pin.

215. The assembly of claim 214, wherein the lock comprises a mechanical lock.

216. The assembly of claim 214, wherein the lock comprises a deformation in the terminal pin.

217. The assembly of claim 214, wherein the lock comprises a cured polymer.

218. The assembly of claim 213, wherein the maintaining means comprises a wire bond pad attached to the terminal pin.

219. The assembly of claim 218, including a non-conductive substrate disposed between the wire bond pad and the inductor.

220. The assembly of claim 213, wherein the active implantable medical device comprises a cardiac pacemaker, an implantable defibrillator, a cochlear implant, a neurostimulator, a drug pump, a ventricular assist device, an implantable sensing system, a gastric pacemaker or a prosthetic device.

221. The assembly of claim 213, wherein the inductor is bonded to the capacitor utilizing a non-conductive polyimide, glass, Paralyne, a ceramic bonding material, epoxy, silicone, or a thermal plastic supportive tape adhesive.

222. The assembly of claim 213, wherein the inductor comprises a material selected from cobalt zinc ferrite, nickel zinc ferrite, manganese zinc ferrite, powdered iron, or molypermalloy.

223. The assembly of claim 213, including a conformal coating over the inductor comprising Paralyne.

224. The assembly of claim 213, including an insulator disposed between the inductor and the terminal pin, wherein the insulator comprises a non-conductive polymer.

225. The assembly of claim 224, wherein the non-conductive polymer comprises an epoxy, a thermal-setting non-conductive adhesive, a non-conductive polyimide, or a silicone material.

226. The assembly of claim 213 including a second inductor through which the terminal pin extends in non-conductive relation.

227. The assembly of claim 226, wherein the inductors are disposed adjacent to one another.

228. The assembly of claim 227, comprising at least one additional inductor stacked onto another one of the inductors.

229. The assembly of claim 226, wherein the inductors are each comprised of materials having different physical or electrical properties.

230. The assembly of claim 226, wherein the inductors are each comprised of materials having the same physical or electrical properties.

231. The assembly of claim 226, wherein the inductors are disposed on opposite sides of the capacitor.

232. The assembly of claim 231, wherein at least one of the inductors is disposed on a body fluid side of the feedthrough terminal assembly.

233. The assembly of claim 231, wherein the second inductor is disposed adjacent to the ferrule.

234. The assembly of claim 231, wherein the inductors are disposed adjacent to opposing surfaces of the capacitor.

235. The assembly of claim 234, wherein the inductors are bonded to the capacitor.

236. The assembly of claim 234, wherein the capacitor and the inductors are disposed within and conductively isolated from the ferrule.

237. The assembly of claim 213, wherein the capacitor and the inductor are housed within the ferrule.

238. The assembly of claim 237, including an insulative cap disposed over the inductor opposite the capacitor.

239. The assembly of claim 213, wherein the capacitor is disposed on a body fluid side of the feedthrough terminal assembly.

240. The assembly of claim 213, wherein the feedthrough capacitor comprises first and second feedthrough capacitors associated with the inductor in non-conductive relation.

241. The assembly of claim 240, wherein the first and second feedthrough capacitors are disposed adjacent to opposing surfaces of the inductor.

242. The assembly of claim 241, wherein the capacitors are bonded to the inductor.

243. The assembly of claim 241, wherein each capacitor is internally grounded.

244. The assembly of claim 241, wherein the first and second capacitors each include a first set of electrode plates conductively coupled to the terminal pin, and a second set of electrode plates conductively coupled to the ferrule.

245. The assembly of claim 244, wherein the first capacitor comprises an externally grounded capacitor, and the second capacitor comprises an internally grounded capacitor, the feedthrough terminal assembly further including a conductive material extending through both the first and second feedthrough capacitors to conductively couple the second set of electrode plates of the second capacitor with the second set of electrode plates of the first capacitor.

246. The assembly of claim 245, wherein the first and second feedthrough capacitors are disposed adjacent to opposing surfaces of the inductor.

247. The assembly of claim 245, wherein the conductive material comprises a thermal setting conductive adhesive, a solder, or a solder paste.

248. The assembly of claim 245, wherein the conductive material comprises a conductive pin.

249. The assembly of claim 248, wherein the conductive pin comprises a nail head pin.

250. The assembly of claim 248, wherein the conductive pin comprises a pin attached to an underlying hermetic insulator.

251. The assembly of claim 213, including an hermetic insulator disposed between the terminal pin and the ferrule, wherein the capacitor is disposed adjacent to the hermetic insulator.

252. The assembly of claim 251, wherein the inductor and the capacitor each include an aperture through which a leak detection gas can be detected.

\* \* \* \* \*

UNITED STATES PATENT AND TRADEMARK OFFICE
CERTIFICATE OF CORRECTION

PATENT NO. : 6,999,818 B2 Page 1 of 1
APPLICATION NO. : 10/825900
DATED : February 14, 2006
INVENTOR(S) : Robert A. Stevenson et al.

It is certified that error appears in the above-identified patent and that said Letters Patent is hereby corrected as shown below:

Column 37, Line 65
Change Claim 100 (in the first instance) as follows:

~~100.~~ 99. The assembly of claim 94, wherein the maintaining means comprises a wire bond pad attached to the terminal pin.

Signed and Sealed this

Fifth Day of September, 2006

JON W. DUDAS
*Director of the United States Patent and Trademark Office*